US008150629B2

(12) United States Patent
Geerts et al.

(10) Patent No.: US 8,150,629 B2
(45) Date of Patent: Apr. 3, 2012

(54) METHOD AND APPARATUS FOR COMPUTER MODELING OF THE INTERACTION BETWEEN AND AMONG CORTICAL AND SUBCORTICAL AREAS IN THE HUMAN BRAIN FOR THE PURPOSE OF PREDICTING THE EFFECT OF DRUGS IN PSYCHIATRIC AND COGNITIVE DISEASES

(75) Inventors: Hugo Geerts, Berwyn, PA (US); Athan Spiros, Portland, OR (US)

(73) Assignee: In Silico Biosciences, Lexington, MA (US)

( * ) Notice: Subject to any disclaimer, the term of this patent is extended or adjusted under 35 U.S.C. 154(b) by 0 days.

(21) Appl. No.: 11/595,313

(22) Filed: Nov. 10, 2006

(65) Prior Publication Data

US 2007/0106479 A1 May 10, 2007

Related U.S. Application Data

(60) Provisional application No. 60/735,618, filed on Nov. 10, 2005.

(51) Int. Cl.
*G06G 7/48* (2006.01)
*G06F 19/00* (2011.01)
(52) U.S. Cl. ............................................ 702/19; 703/11
(58) Field of Classification Search ........................ None
See application file for complete search history.

(56) References Cited

U.S. PATENT DOCUMENTS

| 5,299,121 A | 3/1994 | Brill et al. |
| 5,808,918 A | 9/1998 | Fink et al. |
| 6,051,029 A | 4/2000 | Paterson et al. |
| 6,069,629 A | 5/2000 | Paterson et al. |
| 6,078,739 A | 6/2000 | Paterson et al. |
| 6,159,948 A | 12/2000 | Robertson et al. |
| 6,188,988 B1 | 2/2001 | Barry et al. |
| 6,490,573 B1 | 12/2002 | Njemanze |
| 6,539,347 B1 | 3/2003 | Paterson et al. |

(Continued)

OTHER PUBLICATIONS

Bertolino et al., Interaction of COMT Val108/158 Met Genotype and Olanzapine Treatment on Prefrontal Cortical Function in Patients with Schizophrenia, Am J Psychiatry, 2004, 161, 1798-1805.*

(Continued)

*Primary Examiner* — Marjorie Moran
*Assistant Examiner* — Larry D Riggs, II
(74) *Attorney, Agent, or Firm* — Berliner & Associates

(57) ABSTRACT

Computer modeling of interactions between and among cortico and subcortical areas of the human brain, for example in a normal and a pathological state resembling schizophrenia which pathological state has inputs representing the effects of a drug(s), for the purpose of using the outputs to predict the effect of drugs in psychiatric and cognitive diseases on one or more clinical scales. Diseases that can be modeled include psychiatric disorders, such as schizophrenia, bipolar disorder, major depression, ADHD, autism, obsessive-compulsive disorder, substance abuse and cognitive deficits therein and neurological disorders such as Alzheimer's disease, Mild Cognitive impairment, Parkinson's disease, stroke, vascular dementia, Huntington's disease, epilepsy and Down syndrome. The computer model preferably uses the biological state of interactions between and among cortico and subcortical areas of the human brain, to define the biological processes related to the biological state of the generic synapse model, the striatum, Locus Coeruleus, Dorsal raphe, hippocampus, amygdala and cortex, as well as certain mathematical relationships related to interactions among biological variables associated with the biological processes.

18 Claims, 15 Drawing Sheets

Medium spiny neuron model for PANSS Total

U.S. PATENT DOCUMENTS

| | | | |
|---|---|---|---|
| 6,542,858 | B1 | 4/2003 | Grass et al. |
| 6,594,524 | B2 | 7/2003 | Esteller et al. |
| 6,647,358 | B2 | 11/2003 | Grass et al. |
| 6,658,396 | B1 | 12/2003 | Tang |
| 6,709,866 | B2 | 3/2004 | Robertson et al. |
| 6,717,031 | B2 | 4/2004 | Games et al. |
| 6,804,661 | B2 | 10/2004 | Cook |
| 6,862,561 | B2 | 3/2005 | Defranoux et al. |
| 6,871,171 | B1 | 3/2005 | Agur et al. |
| 6,949,354 | B2 | 9/2005 | Villa et al. |
| 6,983,237 | B2 | 1/2006 | Paterson et al. |
| 7,133,814 | B2 | 11/2006 | Agur et al. |
| 7,165,017 | B2 | 1/2007 | Paterson et al. |
| 7,215,994 | B2 | 5/2007 | Huiku |
| 2002/0091654 | A1 | 7/2002 | Alroy |
| 2003/0046114 | A1 | 3/2003 | Davies et al. |
| 2003/0088237 | A1 | 5/2003 | Agur et al. |
| 2003/0097220 | A1 | 5/2003 | Agur et al. |
| 2003/0124552 | A1 | 7/2003 | Lindemann et al. |
| 2003/0211459 | A1 | 11/2003 | Breiter et al. |
| 2004/0009459 | A1 | 1/2004 | Anderson et al. |
| 2004/0068199 | A1 | 4/2004 | Echauz et al. |
| 2004/0107084 | A1 | 6/2004 | Arakelyan et al. |
| 2005/0003341 | A1 | 1/2005 | Polansky |
| 2005/0043774 | A1 | 2/2005 | Devlin et al. |
| 2005/0118171 | A1 | 6/2005 | Hurez et al. |
| 2005/0130192 | A1 | 6/2005 | Paterson |
| 2005/0131663 | A1 | 6/2005 | Bangs et al. |
| 2005/0148496 | A1 | 7/2005 | Defranoux et al. |
| 2005/0158321 | A1 | 7/2005 | Hurez et al. |
| 2005/0159357 | A1 | 7/2005 | Hurez et al. |
| 2005/0208151 | A1 | 9/2005 | Hurez et al. |
| 2005/0216243 | A1 | 9/2005 | Graham et al. |
| 2005/0261803 | A1 | 11/2005 | Seth et al. |
| 2005/0272984 | A1 | 12/2005 | Huiku |
| 2006/0004296 | A1 | 1/2006 | Huiku et al. |
| 2006/0018833 | A1 | 1/2006 | Murphy et al. |
| 2006/0031059 | A1 | 2/2006 | Paterson et al. |
| 2006/0089824 | A1 | 4/2006 | Siekmeier et al. |
| 2006/0117397 | A1 | 6/2006 | Rutkowski et al. |
| 2006/0167637 | A1 | 7/2006 | Agur et al. |
| 2006/0195308 | A1 | 8/2006 | Kadambi et al. |
| 2006/0217614 | A1 | 9/2006 | Takala et al. |
| 2007/0010723 | A1 | 1/2007 | Uutela et al. |
| 2007/0015763 | A1 | 1/2007 | Romano |
| 2007/0026365 | A1 | 2/2007 | Friedrich et al. |
| 2007/0026458 | A1 | 2/2007 | Polidori et al. |
| 2007/0044162 | A1 | 2/2007 | Riess et al. |
| 2007/0054331 | A1 | 3/2007 | Kirnasovsky et al. |
| 2007/0079390 | A1 | 4/2007 | Rajakumar et al. |
| 2007/0092865 | A1 | 4/2007 | Lynch et al. |
| 2007/0094481 | A1 | 4/2007 | Snook et al. |
| 2008/0027651 | A1 | 1/2008 | Siekmeier |

OTHER PUBLICATIONS

Brown et al., How laminar frontal cortex and basal ganglia circuits interact to control planned and reactive saccades, Neural Networks, 2004, 17, 471-510.*

Gurevich et al., Mesolimbic Domapmine D3 Receptors and use of antipsychotics in patients with Schizophrenia, Arch Gen Psychiatry, 1997, 54, 225-232.*

Kimko et al., Prediction of the outcome of a phase 3 clinical trial of an antischizophrenic agent (quetiapine fumarate) by simulation with a population pharmacokinetic and pharmacodynamic model, Clinical Pharmacology & Therapeutics, 2000, 68(5), 568-577.*

Weber et al., Circadian patterns of neurotransmitter related gene expression in motor regions of the rat brain, Neuroscience Letters, 2004, 358, 17-20.*

Eugenia V. Gurevich, et al, "*Mesolimbic Dopamine $D_3$ Receptors and Use of Antipsychotics in Patients with Schizophrenia*" Arch Gen Psychiatry/ vol. 54, Mar. 1997 (p. 225-232).

Abi-Dargham A, Rodenhiser J, Printz D, Zea-Ponce Y, Gil R, Kegeles LS, Weiss R, Cooper TB, Mann JJ, Van Heertum RL, Gorman JM, Laruelle M. Increased baseline occupancy of D2 receptors by dopamine in schizophrenia. Proc Natl Acad Sci U S A. 2000;97(14):8104-9.

Bertolino A, Caforio G, Blasi G, De Candia M, Latorre V, Petruzzella V, Altamura M, Nappi G, Papa S, Callicott JH, Mattay VS, Bellomo A, Scarabino T, Weinberger DR, Nardini M. *Am J Psychiatry*. Oct. 2004;161(10):1798-805 Interaction of COMT (Val(108/158)Met) genotype and olanzapine treatment on prefrontal cortical function in patients with schizophrenia. Am J Psychiatry. 2004;161(10):1798-805.

Brown P, Oliviero A, Mazzone P, Insola A, Tonali P, Di Lazzaro V. Dopamine dependency of oscillations between subthalamic nucleus and pallidum in Parkinson's disease. *J Neurosci*. 2001;21(3):1033-8.

Brunel N, Wang XJ. (2001) Effects of neuromodulation in a cortical network model of object working memory dominated by recurrent inhibition. J Comput Neurosci. 11:63-85.

Cragg SJ, Nicholson C, Kume-Kick J, Tao L, Rice ME. (2001). Dopamine-mediated volume transmission in midbrain is regulated by distinct extracellular geometry and uptake. J Neurophysiol. Apr;85(4):1761-71.

Freedman S, Patel S, Marwood R, Emms F, Seabrook G, Knowles M, McAllister G. Expression and pharmacological characterization of the human D3 dopamine receptor. J Pharmacol Exp Ther. Jan. 1994;268(1):417-26.

Hasselmo ME, Wyble BP. (1997) Free recall and recognition in a network model of the hippocampus: simulating effects of scopolamine on human memory function. Behav Brain Res. 89:1-34.

Im W., Chio C, Alberts G, Dinh D. Positive allosteric modulator of the human 5-HT2C receptor. Mol Pharmacol. 2003; 64:78-84.

Kovacs I, Yamamura H, Waite S, Varga EV, Roeske W. Pharmacological comparison of the cloned human and rat M2 muscarinic receptor genes expressed in the murine fibroblast (B82) cell line. J Pharmacol Exp Ther. Feb. 1998;284(2):500-7.

Kroese et al. H1-histamine receptor affinity predicts short-term weight gain for typical and atypical antipsychotic drugs. Neuropsychopharmacology. Mar. 2003;28(3):519-26.

Menschik ED, Finkel LH. Cholinergic neuromodulation and Alzheimer's disease: from single cells to network simulations. Prog Brain Res. 1999;121:19-45.

Montague PR, Hyman SE, Cohen JD. Computational roles for dopamine in behavioural control. Nature. Oct. 14, 2004a;431(7010):760-7.

Muramatsu I, Taniguchi T, Okada K. Tamsulosin. (1998). alpha1-adrenoceptor subtype-selectivity and comparison with terazosin. Jpn J Pharmacol.;78(3):331-5.

Naselsky DP, Ashton D, Ruffolo RR Jr, Hieble JP. (2001). Rabbit alpha2-adrenoceptors: both platelets and adipocytes have alpha2A-pharmacology. J Pharmacol Exp Ther. ;298(1):219-25.

Smith AJ, Becker S, Kapur S. A computational model of the functional role of the ventral-striatal D2 receptor in the expression of previously acquired behaviors. Neural Comput. Feb. 2005;17(2):361-95.

Tauscher J, Jones C, Remington G, Zipursky RB, Kapur S Significant dissociation of brain and plasma kinetics with antipsychotics. Mol Psychiatry. 2002;7(3):317-21.

Tort 2006, Progress in Neuro-psychopharmacology & Biol Psych 30, 541-548.

Vauquelin et al. Slow antagonist dissociation and long-lasting in vivo receptor protection, Trends in Pharmacological Sciences, 27, 355-358 (2006).

Wang XJ, Tegner J, Constantinidis C, Goldman-Rakic PS (2004) Division of labor among distinct subtypes of inhibitory neurons in a cortical microcircuit of working memory. Proc Natl Acad Sci U S A. 01(5):1368-73.

Wang XJ. (2006) Toward a prefrontal microcircuit model for cognitive deficits in schizophrenia. Pharmacopsychiatry. 39 :S80-7.

Weber M, Lauterburg T, Tobler I, Burgunder JM. Circadian patterns of neurotransmitter related gene expression in motor regions of the rat brain. Neurosci Lett. 2004;358(1):17-20.

Weinberger DR, Egan MF, Bertolino A, Callicott Jh, Mattay VS, Lipska BK, Berman KF, Goldberg TE. Prefrontal neurons and the genetics of schizophrenia. Biol Psychiatry. Dec. 1, 2001;50(11):825-44.

Yoshitake T, Yoshitake S, Yamaguchi M, Ogren SO, Kehr J. (2003). Activation of 5-HT(1A) autoreceptors enhances the inhibitory effect of galanin on hippocampal 5-HT release in vivo. Neuropharmacology.;44(2):206-13.

Aradi, Computational neuropharmacology: dynamical approaches in drug discover, Trends in Pharmacological Sciences, 27, 240-243, 2006.

Bamford NS, Zhang H, Schmitz Y, et al., Heterosynaptic dopamine neurotransmission selects sets of corticostriatal terminals. Neuron. 2004;42(4):653-63.

Beierlein M, Gibson JR, Connors BW: Two dynamically distinct inhibitory networks in layer 4 of the neocortex, J Neurophysiol 2003, 90:2987-3000.

Bel N, Artigas F. In vivo effects of the simultaneous blockade of serotonin and norepinephrine transporters on serotonergic function. Microdialysis studies. J Pharmacol Exp Ther Sep. 1996; 278(3):1064-72.

Beyer CE, Boikess S, Luo B, Dawson LA. (2002). Comparison of the effects of antidepressants on norepinephrine and serotonin concentrations in the rat frontal cortex: an in-vivo microdialysis study. J Psychopharmacol. ;16(4):297-304.

Braga MF, Aroniadou-Anderjaska V, Manion ST, Hough CJ, Li H. Stress impairs alpha(1A) adrenoceptor-mediated noradrenergic facilitation of GABAergic transmission in the basolateral amygdala. Neuropsychopharmacology. Jan. 2004;29(1):45-58.

Brown A, Schwindt P, Crill W. Voltage-dependence and activation kinetics of pharmacologically defined components of the high threshold calcium current in rat neocortical neurons. J. Neurophysiol 1993; 70: 1530-154.

Bruns D, Riedel D, Klingauf J, Jahn R. (2000). Quantal release of serotonin. Neuron. ;28(1):205-20.

Budygin EA, John CE, Mateo Y, Jones SR. Lack of cocaine effect on dopamine clearance in the core and shell of the nucleus accumbens of dopamine transporter knock-out mice. J Neurosci. 2002;22(10):RC222.

Carr DB, Cooper DC, Ulrich SL, Spruston N, Surmeier DJ. Serotonin receptor activation inhibits sodium current and dendritic excitability in prefrontal cortex via a protein kinase C-dependent mechanism. *J Neurosci.* (2002) 22:6846-55.

Cepeda C, Hurst RS, Altemus KL, Flores-Hernandez J, Calvert CR, Jokel ES, Grandy DK, Low MJ, Rubinstein M, Ariano MA, Levine MS. Facilitated glutamatergic transmission in the striatum of D2 dopamine receptor-deficient mice. J Neurophysiol. 2001;85(2):659-70.

Chevalier G, Deniau JM (1990). Disinhibition as a basic process in the expression of the striatal function. Trends Neurosci 13:277-280.

Cooper DC. The significance of action potential bursting in the brain reward circuit. Neurochem Int. 2002;41(5):333-40.

Di Matteo V, Cacchio M, Di Giulio C, Di Giovanni G, Esposito E. (2002) Biochemical evidence that the atypical antipsychotic drugs clozapine and risperidone block 5-HT(2C) receptors in vivo. Pharmacol Biochem Behav. 71(4):607-13.

Dong J, De Montigny C, Blier R (1999). Assessment of the serotonin reuptake blocking property of YM992: electrophysiological studies in the rat hippocampus and Dorsal Raphe. Synapse; 34(4):277-89.

Durstewitz D, Seamans JK, Sejnowski TJ. J Neurophysiol. Dopamine-mediated stabilization of delay-period activity in a network model of prefrontal cortex. 2000;83(3):1733-50.

Gioanni Y, Rougeot C, Clarke PB, Lepouse C, Thierry AM, Vidal C. Nicotinic receptors in the rat prefrontal cortex: increase in glutamate release and facilitation of mediodorsal thalamo-cortical transmission. Eur J Neurosci 1999;11(1):18-30.

Goldman-Rakie PS. (1999) The physiological approach: functional architecture of working memory and disordered cognition in schizophrenia. Biol Psychiatry. 46:650-61.

Goto Y, O'Donnell P. Timing-dependent limbic-motor synaptic integration in the nucleus accumbens. Proc Natl Acad Sci U S A. Oct. 1, 2002;99(20):13189-93.

Grace AA. Gating of information flow within the limbic system and the pathophysiology of schizophrenia. Brain Res Brain Res Rev. 2000;31(2-3):330-41.

Gruber AJ, Solla S, Surmeier J, Houk J. Modulation of striatal units by expected reward : a spiny neuron model displaying dopamine-induced bistability. J. Neurophysiol 2003; 90: 1095-1114.

Gulledge AT, Stuart GJ Cholinergic inhibition of neocortical pyramidal neurons. J Neurosci. 2005;25(44):10308-20.

Haddjeri N, de Montigny C, Blier P. (1997). Modulation of the firing activity of noradrenergic neurones in the rat locus coeruleus by the 5-hydroxtryptamine system. Br J Pharmacol; 120(5):865-75.

Hsu K, Yang C, Huang C, Gean P. Carbachol induces inward current in neostriatal neurons through M1-like muscarinic receptors, Neuroscience. Aug. 1996;73(3):751-60.

Hyde TM, Egan MF, Brown RJ, Weinberger DR, Kleinman JE. Diurnal variation in tardive dyskinesia. Psychiatry Res. 1995;56(1):53-7.

Ince E, Ciliax B, Levey A. Differential expression of D1 and D2 dopamine and m4 muscarinic acetylcholine receptor proteins in identified striatonigral neurons Synapse. Dec. 1997;27(4):357-66.

Gurevich EV, Bordelon Y, Shapiro RM, Arnold SE, Gur RE, Joyce JN. Mesolimbic dopamine D3 receptors and use of antipsychotics in patients with schizophrenia. A postmortem study. *Arch Gen Psychiatry.*, 1997;54(3):255-32.

Jackson MB, Redman SJ. Calcium dynamics, buffering, and buffer saturation in the boutons of dentate granule-cell axons in the hilus, J Neurosci. Mar. 1, 2003;23(5):1612-21.

Kimko et al. Prediction of the outcome of a Phase III trial of an antipsyhcotic agent (quietipaine fumarate) by simulation with a population pharmacokinetic and pharmacodynamic model, Clin. Pharmacol. Ther 68, 568, 2000.

Koh PO, Bergson C, Undie AS, Goldman-Rakic PS, Lidow MS. Up-regulation of the D1 dopamine receptor-interacting protein, calcyon, in patients with schizophrenia. Arch Gen Psychiatry. 2003;60(3):311-9.

Koos T, Tepper JM. Dual cholinergic control of fast-spiking interneurons in the neostriatum. *J Neurosci.*, 2002;22(2):529-35.

Laakso A, Bergman J, Haaparanta M, Vilkman H, Solin O, Syvalahti E, Hietala J. Decreased striatal dopamine transporter binding in vivo in chronic schizophrenia. Schizophr Res. 2001;52(1-2):115-20.

Law-Tho D, Hirsch JC, Crepe F. Dopamine modulation of synaptic transmission in rat prefrontal cortex: an in vitro electrophysiological study. Neurosci Res. 1994 ;21(2):151-60.

Macoveanu J, T. N. Klingber, J. Tegner. A Biophysical model of multiple-item working memory: a computational and neuroimaging study. Neuroscience 141; 1611-1618 (2006).

Miles PR, Mundorf ML, Wightman RM. Release and uptake of catecholamines in the bed nucleus of the stria terminalis measured in the mouse brain slice. Synapse. 2002;44(3):188-97.

Miner LA, Backstrom JR, Sanders-Bush E, Sesack SR. (2003) Ultrastructural localization of serotonin2A receptors in the middle layers of the rat prelimbic prefrontal cortex. Neuroscience. 116:107-17.

Montague PR, McClure SM, Baldwin PR, Phillips PE, Budygin EA, Stuber GD, Kilpatrick MR, Wightman RM. Dynamic gain control of dopamine delivery in freely moving animals. J Neurosci. 2004b;24(7):1754-9.

Parnas H, Slutsky I, Rashkovan G, Silman I, Wess J, Parnas I. Depolarization initiates phasic acetylcholine release by relief of a tonic block imposed by presynaptic M2 muscarinic receptors. J Neurophysiol. 2005;93(6):3257-69.

Povlock SL, Schenk JO. A multisubstrate kinetic mechanism of dopamine transport in the nucleus accumbens and its inhibition by cocaine, J Neurochem.1997;69(3):1093-105.

Prange O, Murphy TH. (1999). Analysis of multiquantal transmitter release from single cultured cortical neuron terminals. J Neurophysiol. ;81(4):1810-7.

Prasad S, Semwal P, Deshpande S, Bhatia T, Nimqaonkar VL, Thelma BK. Molecular genetics of schizophrenia: past, present and future. *J Biosci.* 2002;27(1 Suppl 1):35-52.

Puig MV, Santana N, Celada P, Mengod G, Artigas F. In vivo excitation of GABA interneurons in the medial prefrontal cortex through 5-HT3 receptors. Cereb Cortex. 2004;14(12):1365-75.

Richelson E, Souder T. (2000). Binding of antipsychotic drugs to human brain receptors focus on newer generation compounds. Life Sci.;68(1):29-39.

Scarr E., Keriakous D, Crossland N, Dean B. No change in cortical muscarinic M2, M3 receptors or [35S]GTPgammaS binding in schizophrenia, Life Sci. Feb. 9, 2006;78(11):1231-7.

Seeman P, Kapur S. Anesthetics inhibit high-affinity states of dopamine D2 and other G-linked receptors. Synapse. 2003;50(1):35-40.

Silvestri S, Seeman MV, Neorete JC, Houle S, Shammi CM, Remington GJ, Kapur S, Zipursky RB, Wilson AA, Christensen BK, Seeman P. Increased dopamine D2 receptor binding after long-term treatment with antipsychotics in humans: a clinical PET study. *Psychopharmacology (Berl)*. 2000;152(2):174-80.

Strong SP, de Ruyter van Steveninck RR, Bialek W, Koberle R. On the application of information theory to neural spike trains. Pac Symp Biocomput. 1998;:621-32.

Sunahara RK, Guan HC, O'Dowd BF, Seeman P, Laurier LG, Ng G, George SR, Torchia J, Van Tol HH, Niznik HB. Cloning of the gene for a human dopamine D5 receptor with higher affinity for dopamine than D1. Nature. 1991;350(6319):614-9.

Suvannapura A, Levens NR. (1988). Norepinephrine uptake by rat jejunum: modulation by angiotensin II. Am J Physiol. ;254(2 Pt 1):G135-41.

Szabo ST, Blier P. (2002). Effects of serotonin (5-hydroxytryptamine, 5-HT) reuptake inhibition plus 5-HT(2A) receptor antagonism on the firing activity of norepinephrine neurons. J Pharmacol Exp Ther.;302(3):983-91.

Tanaka S. (2006) Dopaminergic control of working memory and its relevance to schizophrenia: a circuit dynamics perspective. Neuroscience. 39:153-71.

Tauscher J, Kufferle B, Asenbaum S, Tauscher-Wisniewski S, Kasper S. Striatal dopamine-2 receptor occupancy as measured with [123I]iodobenzamide and SPECT predicted the occurrence of EPS in patients treated with atypical antipsychotics and haloperidol. Psychopharmacology (Berl). Jun. 2002;162(1):42-9.

Terman, D, Rubin JE, Yew AC, Wilson CJ. 2002. Activity patterns in a model for the subthalamopallidal network of the basal ganglia. J. Neurosci 22:2963-76.

Wayment, H.K., Schenk, JO, Sorg BA. Characterization of extracellular dopamine clearance in the medial prefrontal cortex: role of monoamine uptake and monoamine oxidase inhibition. Neurosci. 2001;21(1):35-44.

Winterer G, Coppola R, Goldberg TE, Egan MF, Jones DW, Sanchez CE, Weinberger DR. Prefrontal broadband noise, working memory, and genetic risk for schizophrenia. Am J Psychiatry. 2004;161(3):490-500.

Yang CR, Seamans JK. Dopamine D1 receptor actions in layers V-VI rat prefrontal cortex neurons in vitro: modulation of dendritic-somatic signal integration. J Neurosci. 1996;16(5):1922-35.

Yelamanchili S, Pendyala G, Brunk I, Dama M, Albrecht U, Ahnert-Hilger G. Differential sorting of the vesicular glutamnate transporter 1 into a defined vesicular pool is regulated by light signaling involving the clock gene period2, Journ of Biol Chem. 2006; 281, 15671-15678.

Zapata A, Shippenberg TS. D2 receptor ligands modulate extracellular dopamine clearance in the nucleus accumbens. J of Neurochemistry, 2002, 81:1035-1042.

Zhou F., Hablitz J. Dopamine modulation of membrane and synaptic properties of interneurons in rat cerebral cortex. J. Neurophysiol. 1999; 81:967-976.

ISA/US International Search Report for PCT/US 08/43887 (Jul. 10, 2007).

* cited by examiner

METHOD AND APPARATUS FOR COMPUTER MODELING OF THE INTERACTION BETWEEN AND AMONG CORTICAL AND SUBCORTICAL AREAS IN THE HUMAN BRAIN FOR THE PURPOSE OF PREDICTING THE EFFECT OF DRUGS IN PSYCHIATRIC AND COGNITIVE DISEASES

CROSS-REFERENCE TO RELATED APPLICATION

This application claims the benefit of U.S. Provisional Application No. 60/735,618 filed Nov. 10, 2005, which is incorporated herein by reference.

FIELD OF INVENTION

This invention generally relates to methods and apparatus for computer modeling of interactions between and among cortico and subcortical areas of the human brain, for example in a normal and a pathological state resembling schizophrenia, which pathological state has inputs representing the effects of a drug(s), for the purpose of using the outputs to predict the effect of drugs in psychiatric and cognitive diseases.

BACKGROUND

In a recent White Paper on Drug Development, the FDA has identified computer modeling as one of the new enabling technologies for improving drug development processes. Computational neuropharmacology, as described herein, is different from database management, data mining and pattern recognition, in that it attempts to predict outcomes based on mathematical models starting from well-defined physico-chemical principles, rather than applying statistical inference techniques.

Database mining is very useful, especially when applied to the integration of pharmacological with clinical information, but by itself it is usually not sufficient to identify drug targets with a sufficient probability of affecting a disease.

As an example, correlating binding affinity data on various human receptor subtypes for a number of neuroleptics with their clinical side-effects has enabled the identification of a number of key receptors involved in weight gain [56]. However, this particular approach uses only binding affinity data and does not take into account the actual dosage used in the clinical setting. Also, the interaction of neuroleptics at the receptor subtypes is also modulated by the affinity of the endogeneous neurotransmitter for the same receptor subtype, the presynaptic firing pattern, possible negative feedback via presynapic autoreceptors and the presence of pharmacologically active metabolites. Thus a mathematical approach encompassing all these interactions in a quantitative way is clearly necessary and has not been presented.

Another major issue is estimating the functional concentration of antipsychotic drugs in the brain. Fortunately, PET imaging using specific radioactive tracers can be used to determine the competition with added antipsychotic drugs at specified receptor subtupes, such as the dopamine D2R. A number of studies have made possible the prediction of brain D2R occupancy levels, measured by radio-active tracer displacement, in function of the plasma level [97], results that have been actually confirmed by experimentally in the human brain [94]. However, this approach as presented does not enable one to determine the actual concentration of the neuroleptic and its metabolite in nM in the human brain, which can be used at other synapses beyond dopaminergic synapses. In addition, it is not possible to determine the level of postynaptic activity, especially in the case of partial agonists.

Simulation has been applied to the problem of slow antagonist dissociation and long-lasting in vivo receptor protection; see Vauquelin et al. [99] which addresses the time-dependent evolution of receptor occupancy, dependent upon both affinity and half-life of the drug. Such approaches while interesting, do not address the level of receptor activation or determination of actual brain drug concentration in clinically relevant conditions.

At least one attempt to simulate the outcome of clinical trials with the antipsychotic quetiapine has been published; see Kimko et al. [51]. In this study, the relation between plasma drug concentration and BPRS scale as a measure of clinical efficacy was modeled as a linear, U-shaped, inhibitory Emax and sigmoidal Emax function, using standard statistical analyses. There was no attempt to include actual physiological interactions or pathology parameters. In view of the large discrepancy between drug plasma levels and actually measured functional brain receptor occupancies [94], it was of no surprise that the model deviated quite considerably from the actual data.

Another commonly used rule for determining the clinical efficacy or side-effect liability of neuroleptics is the degree of D2R occupancy, measured with tracer displacement. This is given by $$D2R\text{-}occ = D2R\text{-}occ\,\text{max}*\text{Dose}/(\text{Dose}+K_i)$$

Where Dose is the dose of the neuroleptic and $K_i$ is a parameter determined from PET imaging studies with radio-active tracers, usually $^{11}$C-racopride.

This method at best yields modest correlatiuons and is clearly not adapted to predict the clinical outcome of novel therapeutic agents with partial agonist effects at the D2R, such as aripiprazole.

The computational neurosciences approach is based upon mathematical models describing actual biophysical processes. In most cases, the readout of these models is neuronal action potentials, which obviously is related to behavior. This area of research has yielded an enormous array of novel insights in the way neuronal circuits code information and perform certain cognitive operations. However, prior to this invention these models have not been integrated together in practical way which would represent a disease state and predict the clinical effect of drugs thereon.

With regard to the problem of schizophrenia, the major brain regions involved are the cortex, the striatum and the hippocampus. There is evidence of a dysfunctional signal-to-noise ratio observed with EEG techniques in patients and siblings [105]. According to the hypothesis developed by Grace [39], the ventral striatum integrates inputs from cortical, amygdale and hippocampal regions. In order to develop an adequate mathematical model of the deficient information processing in the pathology of schizophrenia, there is a need for a detailed model of each of these brain regions, followed by an integration of the different inputs into the ventral striatal computation unit.

There are computational models in the neural areas of interest that have a basic science focus that are linked to schizophrenia. When human outcomes are of interest, the results are more generally linked to behavior rather than disease or particularly schizophrenia (e.g., Montague et al. [70] and Smith et al. [86]). For example, there have been computational models of the striatum and medium spiny projection neurons (e.g. Wolf et al., 2005), of dopamine signaling (e.g., Schultz et al. [83]), of cortical circuitry (e.g., Chen

[21]), and of information processing in the frontal cortex and basal ganglia (e.g., Amos, 2000). None of those computational approaches, however, integrate a biologically-based simulation to human clinical data and derive therapeutic drug targets. The previous modeling did not correlate and compare the output of the simulations with clinical trial results to predict clinical outcomes for untested drugs or determine targets for novel therapeutic drugs.

A range of models have been developed directed at cortical and hippocampal processes relevant to schizophrenia (for review, 32). Recent modeling efforts have largely focused on understanding three fundamental cognitive processes: working memory, the decision process, and attention.

Based on the pioneering work of Pat Goldman-Rakic [37] and others, much research has focused on deficits in working memory function in prefrontal cortex (PFC) and its contribution to loss of executive control and disorganized thinking in schizophrenia. The major modeling efforts in this direction attempt to account for the ability of cortical networks to maintain a stable pattern of activity—e.g., a stable firing pattern—across a population of neurons, in the face of distracting stimuli. Durstewitz and colleagues [30] showed that a simple cortical architecture, based on interconnected pyramidal cells and interneurons, could maintain stable firing (so-called attractor behavior) with firing rates corresponding to experimental data from PFC, and that dopamine, acting through D1 receptors worked to stabilize the activity when distracting activity patterns were applied to "knock" the "goal" out of working memory. A succession of models has taken this attractor model further, notably X J Wang and Miller et al. [100, 67] have incorporated more accurate neuronal models with additional biophysical properties, and have shown more sophisticated attractor behavior. Additional interneuronal types have also been incorporated into the cortical network, based upon a different functional role for dendrite-targeting calbindin positive interneurons versus soma targeting palvalbumin positive interneurons, versus the calretinin positive interneurons that target other interneurons (100).

Thus, a substantial body of computational modeling has been developed to account for recent experimental findings on working memory, decision making, attention and other cognitive processes. The biophysical models of neurons used in these models vary from extremely simplified (integrate-and-fire models), to somewhat sophisticated multicompartmental models incorporating 6 or 7 intrinisic currents and several synaptic receptor currents (usually AMPA, NMDA, and $GABA_A$).

A final set of relevant work in the literature deals with the action of neuromodulators on brain circuit function. In a number of models 14, 27, 92, 31) however, the effect of dopamine is not explicitly calculated on model parameters—it is just assumed, loosely based on experimental literature, that dopamine increases NMDA conductance by a fixed percentage. Similarly, in Hasselmo's models of the effect of acetylcholine on functional connectivity in various hippocampal pathways [44], the effect of the neuromodulator is introduced only at a single effective concentration, and only through its effect on a model parameter, such as synaptic weight.

The dynamics of the neuronal circuits in the prefrontal cortex are important for addressing the issue of cognitive deficits in schizophrenia, an area which has recently been recognized by the NIMH and the FDA as a major unmet medical need. In fact, a very low fraction of 'stable' schizophrenia patients are able to return to their level of professional activity.

It is clear that for accurately describing the effects of antipsychotics and therapies used in psychiatric diseases on the neuronal dynamics in the prefrontal cortex, a new model is required integrating the pharmacological effects of other neurotransmitter systems, such as acetylcholine, serotonin and norepinephrine are needed.

With the advent of pharmacogenomics and functional data on patient genotypes, it is mandatory to have a model which can incorporate these functional genotypes in a rational way.

In the striatum, the most important cell type is a medium spiny neuron (MSN) GABA cell, a computational model of which has been published (40). This model has a dopaminergic D1 mediated input and a glutamate afferent input and was intended to demonstrate a dopamine-indiuced bifurcation and the link to expected reward. However, as all neuroleptics effective in schizophrenia antagonize the dopamine D2R, this model—which lacks D2 receptor—is clearly not sufficient to describe the effect of dopamine receptor modulation on the relation between incoming glutamatergic signals and outgoing GABAergic signals. In addition, both 5-HT2C [28] and D(3) receptor ligands (110) have been documented to modulate the dynamics of dopamine release in the striatum. At least these two pharmacological influences need to be incorporated in the model, as many neuroleptics also affect these receptor subtypes. In addition, novel insights in the pathophysiology of schizophrenia point to the idea of signal and noise (105). Also the gating of hippocampus and amygdala which is seen as major inputs into the N. accumbens [39] is not implemented in this model. Recent experimental data indeed have provided information on the electrophysiological interaction between prefrontal cortex, hippocampus and N. accumbens [38].

There is a need for the integration of information on the interaction and pathways of the different neurotransmitter circuits with their different receptor subtypes in the human brain. Information is available from preclinical microdialysis and voltammetry studies on neurotransmitter levels and electrophysiological studies in well-defined brain regions in the monkey and rat brain. Human information relates imaging data (PET, MRI), functional genomic and postmortem data in appropriate patient populations. The specific affinity of each drug for different receptor subtypes defines its interaction with various neurotransmitter systems.

In particular, interactions between serotonin and norepinephrine are very important in the setting of schizophrenia. Indeed, many antipsychotics currently in use have pharmacological effects at serotonerge and noradrenerge receptor subtypes. In addition, a number of drugs used to treat depression have serotonergic and/or noradrenergic modulation as their primary mode of action. However, good models which can accurately describe the interaction between these two types of neurotransmitters are lacking, despite a wealth of information on the reciprocal interaction between Locus Coeuruleus, the source of noradrenergic neurons and the Dorsal Raphe Nucleus, the source of serotonergic neurons. Therefore a good mathematical model which can take all these interactions into account is necessary.

Computational neuroscience models have described the calculation of biomarkers such as fMRI [60] and EEG [64]. However, other parameters of interest in the field of drug development have not yet been published. There is a need for ways to adapt computational neuropharmacology approaches to (1) identify the 'ideal profile' of drugs, (2) estimate the effect of comedications, (3) perform power calculations based not only on pharmacokinetic variability, but on pharmacodynamic variability as well, (4) estimate the clinical effects of specific functional genotypes, and (5) estimate the influence of chronopharmacodynamics (i.e. the time of the day when drugs are given).

SUMMARY OF INVENTION

This invention fulfills a need for an integrated approach for predicting the effect of potential drugs in schizophrenia. However, it should be understood that the method and systems described herein are applicable to other psychiatric and cognitive diseases as well. In one embodiment, integration of a model of the striatum, model of the pre-fontal cortex, model of the hippocampus, and a receptor competition model is disclosed, in combination with an output from these models, and correlation of this output for many different drugs with a large database of prior clinical trials as a validation means.

Embodiments of the present invention relate to computer modeling of interactions among and between cortical and subcortical brain areas. For example, one embodiment of the present invention relates to a normal and a pathological state resembling schizophrenia, which pathological state has inputs representing the effects of a drug(s), for the purpose of using the outputs to predict the effect of drugs in psychiatric and cognitive diseases.

Another embodiment of the invention is a computer model of a human generic receptor competition model comprising a computer-readable memory storing codes and a processor coupled to the computer-readable memory, the processor configured to execute the codes. The memory comprises code to define biological processes related to the biological state of the receptor model and code to define mathematical relationships related to interactions among biological variables associated with the biological processes.

Another embodiment of the invention is a computer model of the biological state of a generic receptor competition model, comprising code to define the biological processes related to the biological state of the particular network, and code to define the mathematical relationships related to interactions among biological variables associated with the biological processes. At least two of the biological processes are associated with the mathematical relationships. A combination of the code to define the biological processes and the code to define the mathematical relationships define a simulation of the biological state of the cortico-striatal pathway.

In yet another embodiment of the invention one uses computer executable software code comprised of code to define biological processes related to a biological state of generic receptor competition model including code to define mathematical relations associated with the biological processes.

In one embodiment, the invention is a method for developing a computer model of interactions between and among cortical and sub-cortical brain regions. The method comprises the steps of identifying data relating to a biological state of the striatum and cortex; identifying biological processes related to the data, these identified biological processes defining at least one portion of the biological state of the striatum, hippocampus and cortex; and combining the biological processes to form a simulation of the biological state of the interactions between and among cortical and sub-cortical brain regions. The biological state of the interactions between and among cortical and sub-cortical brain regions can be, for example, the state of a normal or a diseased interaction. The diseases that can be modeled include psychiatric disorders, such as schizophrenia, bipolar disorder, major depression, ADHD, autism, obsessive-compulsive disorder, substance abuse and cognitive deficits therein and neurological disorders such as Alzheimer's disease, Mild Cognitive impairment, Parkinson's disease, stroke, vascular dementia, Huntington's disease, epilepsy and Down syndrome.

Another embodiment of the invention is a computer model of the biological state of interactions between and among cortical and sub-cortical brain regions, comprising code to define the biological processes related to the biological state of the striatum and cortex, and code to define the mathematical relationships related to interactions among biological variables associated with the biological processes. At least two of the biological processes are associated with the mathematical relationships. A combination of the code to define the biological processes and the code to define the mathematical relationships define a simulation of the biological state of the cortico-striatal pathway.

In yet another embodiment of the invention one uses computer executable software code comprised of code to define biological processes related to a biological state of interactions between and among cortical and sub-cortical brain regions including code to define mathematical relations associated with the biological processes.

Another embodiment of the invention is a computer model of a interactions between and among cortical and sub-cortical human brain regions, comprising a computer-readable memory storing codes and a processor coupled to the computer-readable memory, the processor configured to execute the codes. The memory comprises code to define biological processes related to the biological state of the interactions between and among cortical and sub-cortical brain regions, and code to define mathematical relationships related to interactions among biological variables associated with the biological processes.

Another embodiment of the invention is a computer model of the biological state of a neuronal network, which can be cortical or hippocampal, comprising code to define the biological processes related to the biological state of the particular network, and code to define the mathematical relationships related to interactions among biological variables associated with the biological processes. At least two of the biological processes are associated with the mathematical relationships. A combination of the code to define the biological processes and the code to define the mathematical relationships define a simulation of the biological state of the interactions between and among cortical and sub-cortical brain regions.

In yet another embodiment of the invention one uses computer executable software code comprised of code to define biological processes related to a biological state of the cortical network including code to define mathematical relations associated with the biological processes.

Another embodiment of the invention is a computer model of a human Dorsal Raphe-Locxus Coeruleus pathway, comprising a computer-readable memory storing codes and a processor coupled to the computer-readable memory, the processor configured to execute the codes. The memory comprises code to define biological processes related to the biological state of the cortical network and code to define mathematical relationships related to interactions among biological variables associated with the biological processes.

Another embodiment of the invention is a computer model of the biological state of a Dorsal Raphe-Locus Coeruleus, comprising code to define the biological processes related to the biological state of the particular network, and code to define the mathematical relationships related to interactions among biological variables associated with the biological processes. At least two of the biological processes are associated with the mathematical relationships. A combination of the code to define the biological processes and the code to define the mathematical relationships define a simulation of the biological state of the interactions between and among cortical and sub-cortical brain regions In yet another embodiment of the invention one uses computer executable software code comprised of code to define biological processes related to a biological state of the Dorsal Raphe-Locus Coeruleus including code to define mathematical relations associated with the biological processes.

The computer model allows the estimation of the effect of an untested pharmacological agent on a well-defined clinical scale used in assessing psychiatric diseases together with a confidence interval, based upon the correlation between the computer model outcome of existing neuroleptics at their appropriate doses and the reported clinical effects on scales used in psychiatric disorders.

The computer model also allows for the effect of particular genotypes to be predicted, and if functional effects of these genotypes at the physiological levels are known such predictions can be used in improving the set up of clinical trials by supporting the decision of genotyping.

The computer model also allows for predicting the effect of specific dosage timing, when information over the circadian rhythms of receptor subtypes involved in the pharmacology of the drug are known; such prediction can improve the clinical outcome in trials by better synchronizing the pharmacokinetics of the compound with the endogenous rhythms of the brain.

The computer model allows also the identification of important receptor subtype targets for which the outcome is very sensitive; these receptor subtypes can form the pharmacological basis of a drug profile, and can lead to the identification and development of a novel drug with better anticipated clinical effects on various clinical scales, used in psychiatric diseases.

DETAILED DESCRIPTION

Figure 1:
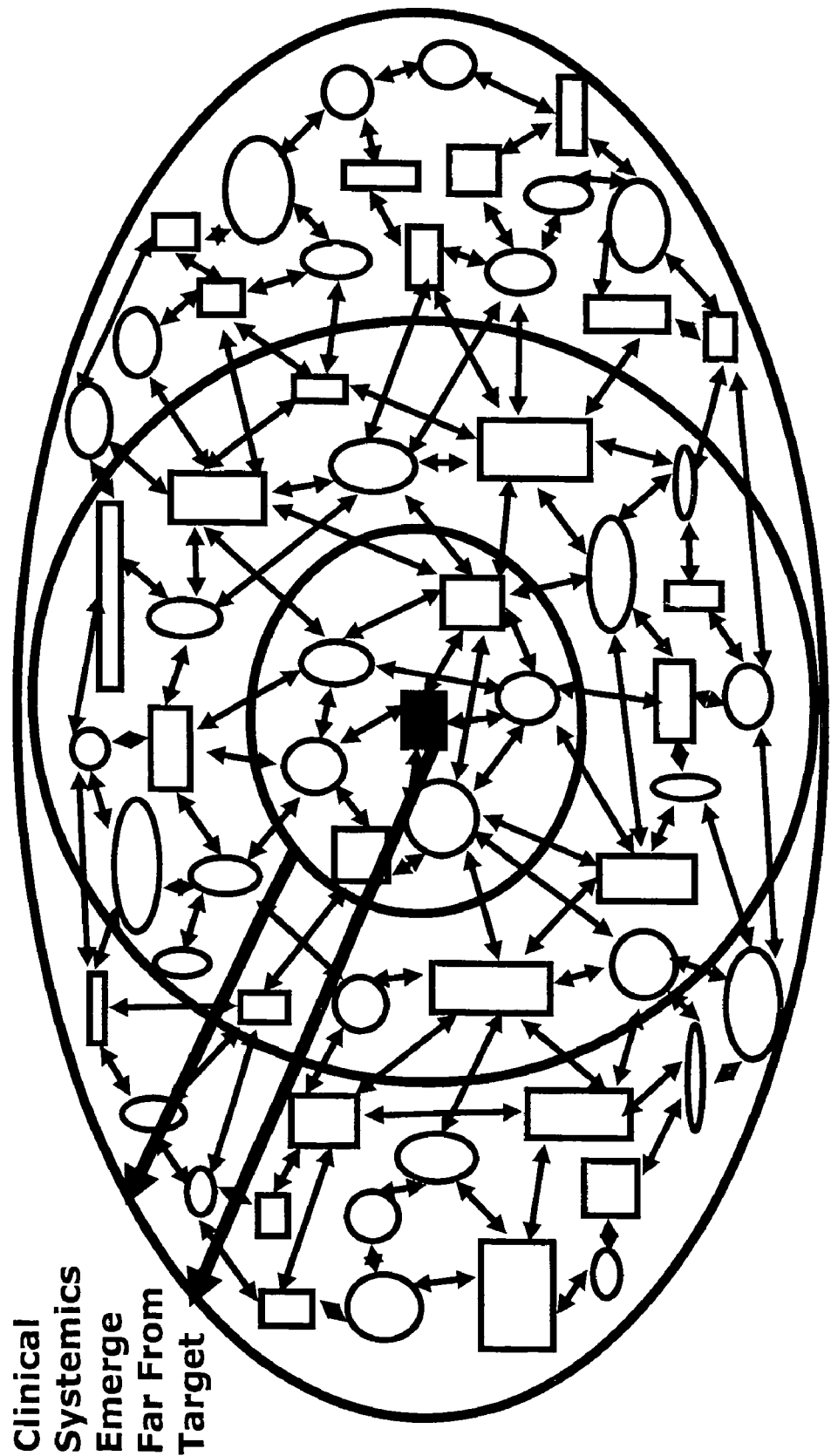
FIG. 1. Shows a schematic illustrating the inability of conventional methods to identify good drug targets.

The term "biological process" is used herein to mean an interaction or series of interactions between biological variables. Biological processes can include, for example, presynaptic autoreceptor regulation of neurotransmitter release; regulation of neurotransmitters bound to receptors; breakdown of the neurotransmitter; specific presynaptic firing patterns; appropriate facilitation and depression of presynaptic vesicle release. The term "biological process" can also include a process comprising of one or more therapeutic agents, for example the process of binding a therapeutic agent to a cellular receptor. Each biological variable of the biological process can be influenced, for example, by at least one other biological variable in the biological process by some biological mechanism, which need not be specified or even understood.

The term "biological variables" refers to the extra-cellular or intra-cellular constituents that make up a biological process. For example, the biological variables can include neurotransmitters, receptors, binding affinities, transportation rates, metabolites, DNA, RNA, proteins, enzymes, hormones, cells, organs, tissues, portions of cells, tissues, or organs, subcellular organelles, chemically reactive molecules like H.sup.+, superoxides, ATP, citric acid, protein albumin, as well as combinations or aggregate representations of these types of biological variables. In addition, biological variables can include therapeutic agents such anti-psychotic and neuroleptic drugs.

The term "biological state" is used herein to mean the result of the occurrence of a series of biological processes. As the biological processes change relative to each other, the biological state also undergoes changes. One measurement of a biological state, is the level of activity of biologic variables, parameters, and/or processes at a specified time and under specified experimental or environmental conditions.

The term biological attribute is used herein to mean biological characteristics of a biological state, including a disease state. For example, biological attributes of a particular disease state include clinical signs and diagnostic criteria associated with the disease. The biological attributes of a biological state, including a disease state, can be measurements of biological variables, parameters, and/or processes. For example, for the disease state of schizophrenia, the biological attributes can include measurements of DR2 or dopamine levels.

The term "reference activity pattern" is used herein to mean a set of biological attributes that are measured in a normal or diseased biological system. For example, the measurements may be performed on blood samples, on biopsy samples, or cell cultures derived from a normal or diseased human or animal or imaging scans of the brain. Examples of diseased biological systems include cellular or animal models of schizophrenia, including a human schizophrenia patient.

The term "simulation" is used herein to mean the numerical or analytical integration of a mathematical model. For example, simulation can mean the numerical integration of the mathematical model of the biological state defined by a mathematical equation.

A biological state can include, for example, the state of an individual cell, an organ, a tissue, and/or a multi-cellular organism. A biological state can also include the activation state of a neural circuit, the firing pattern of specific neurons or the neurotransmitter level in a specific brain region. These conditions can be imposed experimentally, or may be conditions present in a patient type. For example, a biological state of the striatum can include an elevated free dopamine level for a schziophrenic patient at a certain age and disease duration. In another example, the biological states of the prefrontal cortex can include the state in which a patient with a certain disease undergoes a specific treatment.

The term cognitively normal is used herein to mean a process of receiving, processing, storing, and using information that occurs in a non-diseased brain.

The term "disease state" is used herein to mean a biological state where one or more biological processes are related to the cause or the clinical signs of the disease. For example, a disease state can be the state of a diseased cell, a diseased organ, a diseased tissue, or a diseased multi-cellular organism. Such diseases can include, for example, schizophrenia, bipolar disorder, major depression, ADHD, autism obsessive-compulsive disorder, substance abuse, Alzheimer's disease, Mild Cognitive impairment, Parkinson's disease, stroke, vascular dementia, Huntington's disease, epilepsy and Down syndrome. A diseased state could also include, for example, a diseased protein or a diseased process, such as defects in receptor signaling, neuronal firing, and cell signaling, which may occur in several different organs.

The term cerebro-active drugs is used herein to mean any drug affecting the brain such as, but not limited to, neuroleptics.

The terms antipsychotics/neuroleptics are used herein to mean drugs used for the treatment of psychosis, such as schizophrenia. These drugs include, but are not limited to, clozapine, risperidone, aripiprazole, olanzapine, Zyprexa, quetiapine, and ziprasidone.

The term "computer-readable medium" is used herein to include any medium which is capable of storing or encoding a sequence of instructions for performing the methods described herein and can include, but not limited to, optical and/or magnetic storage devices and/or disks, and carrier wave signals.

The term circadian profiles is used herein to mean profiles of brain wave activity, hormone production, cell regeneration and other biological activities linked to a roughly-24-hour cycle in physiological processes.

The computer system as used here is any conventional system including a processor, a main memory and a static memory, which are coupled by bus. The computer system can further include a video display unit (e.g., a liquid crystal display (LCD) or cathode ray tube (CRT)) on which a user interface can be displayed). The computer system can also include an alpha-numeric input device (e.g., a keyboard), a cursor control device (e.g., a mouse), a disk drive unit, a signal generation device (e.g., a speaker) and a network interface device medium. The disk drive unit includes a computer-readable medium on which software can be stored. The software can also reside, completely or partially, within the main memory and/or within the processor. The software can also be transmitted or received via the network interface device.

FIG. 1 shows the general innovative concept of this invention. The clinical or systemic readout is a consequence of the interaction of numerous pathways and processes, the majority of which are unknown. The classical drug discovery paradigm focuses on one specific target (i.e. D2R in schizophrenia) and medicinal chemistry efforts are aimed to develop very specific modulatory agents, under the assumption that any additional pharmacology might lead to unwanted side-effects. The statistical distance between that specific target and the clinical outcome is substantial, leading to a modest correlation between the effectivity of the compound at the target and the clinical scale. In contrast, one embodiment of this invention describes a systems biology approach which takes into account the whole constellation, including both the known environment of process around the key target as well as a number of processes which are not yet full described, all of which would lead to a better correlation between the predicted outcome and the clinical reality. For instance, this invention relates to the modeling of a number of interactions with neighboring targets (i.e. D1, D3, 5HT1A, 5HT2A, etc in CNS diseases) around the specific target for which the functional relation is known to a certain extent.

Figure 2:
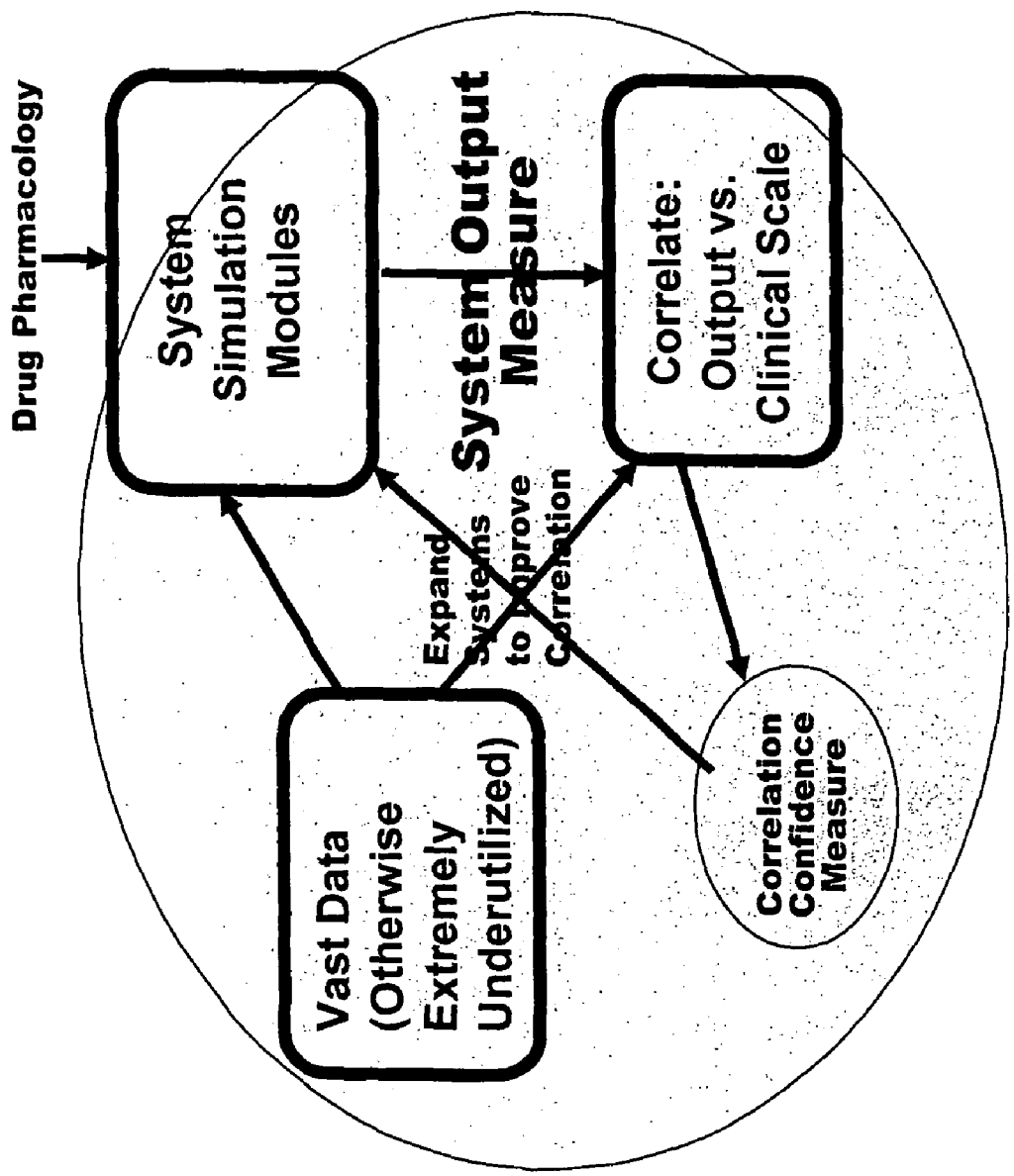
FIG. 2. Shows a schematic of the simulation platform which represents one embodiment of the invention.

FIG. 2 shows a simulation platform made of four conceptual dimensions. These dimensions are involved in the validation process which consists of a number of iterative steps, leading to increasingly better correlations with the clinical reality. The simulation platform described herein consists of (1) a database of knowledge on pharmacology, physiology and pathology; both preclinical and clinical databases which supports the actual development of the different simulation models; (2) a number of simulation models, which take the known pharmacology of the drug as input and outputs a system measure; (3) a statistical correlation module, which correlates the module output with actual clinical results of the same drugs at the same doses, resulting in (4) a correlation confidence measure.

The database, extracted from publicly available data on neurophysiology, neuron-anatomy and pharmacology in both preclinical models and clinical situations, provides the scientific basis for the development of the different simulation modules. The drug pharmacology (in terms of its affinity, plasma concentrations and functional effects) is used as input into the model to calculate a specific readout. This readout is then correlated with the actual clinical effect of the same drug-dose combination in the human patient. When this is done over all the available drug-dose combinations for which there is clinical information, a correlation coefficient can be calculated, which indicates how good the model predicts the actual clinical reality. This process is used in an iterative cycle which leads to better and better predictive models.

In one embodiment, the clinical database used for optimizing and validating the model consists of a detailed database of 26967 patients (taken from 87 published papers), 20 different neuroleptic drugs and 71 neuroleptic-dose combinations on the following clinical scales:

Positive and Negative Syndrome Scale (PANSS) total, positive change, negative size effect, negative change, disorganization size effect, psychopathology change, change in anxiety/depression, fraction of patients improved on PANSS Scale for Assessment of Negative Symptoms (SANS)

Brief Psychiatric Rating Scale (BPRS) total, size effect change in BPRS total, BPRS core items, BPRS positive, BPRS negative, BPRS activity, BPRS anergia, change in anxiety/depression, BPRS hostility, BPRS thought disturbance, fraction of BPRS responders Clinical Global Impressions-Severity of Illness Scale (CGI-S) improvement, CGI-Global improvement.

The database further contains preclinical information on rodent and primate models of neuro-anatomy, neurophysiology and neuropharmacology and on clinical information from imaging, postmortem and genotype origin.

This information is used to develop and validate the different mathematical models as disclosed herein. During the development of the model, preclinical validation is used in a bootstrap mode, i.e. the model predicts the outcome of preclinical studies which were not used for its development. The different models use pharmacology input from different agents at well-defined concentrations and calculate the outcome. This outcome is then used in a statistical correlation module, in which these results are compared to the actual clinical results obtained in patients with the same drug at that particular concentration. The model is successively validated using the correlation coefficient as benchmark.

Figure 3:
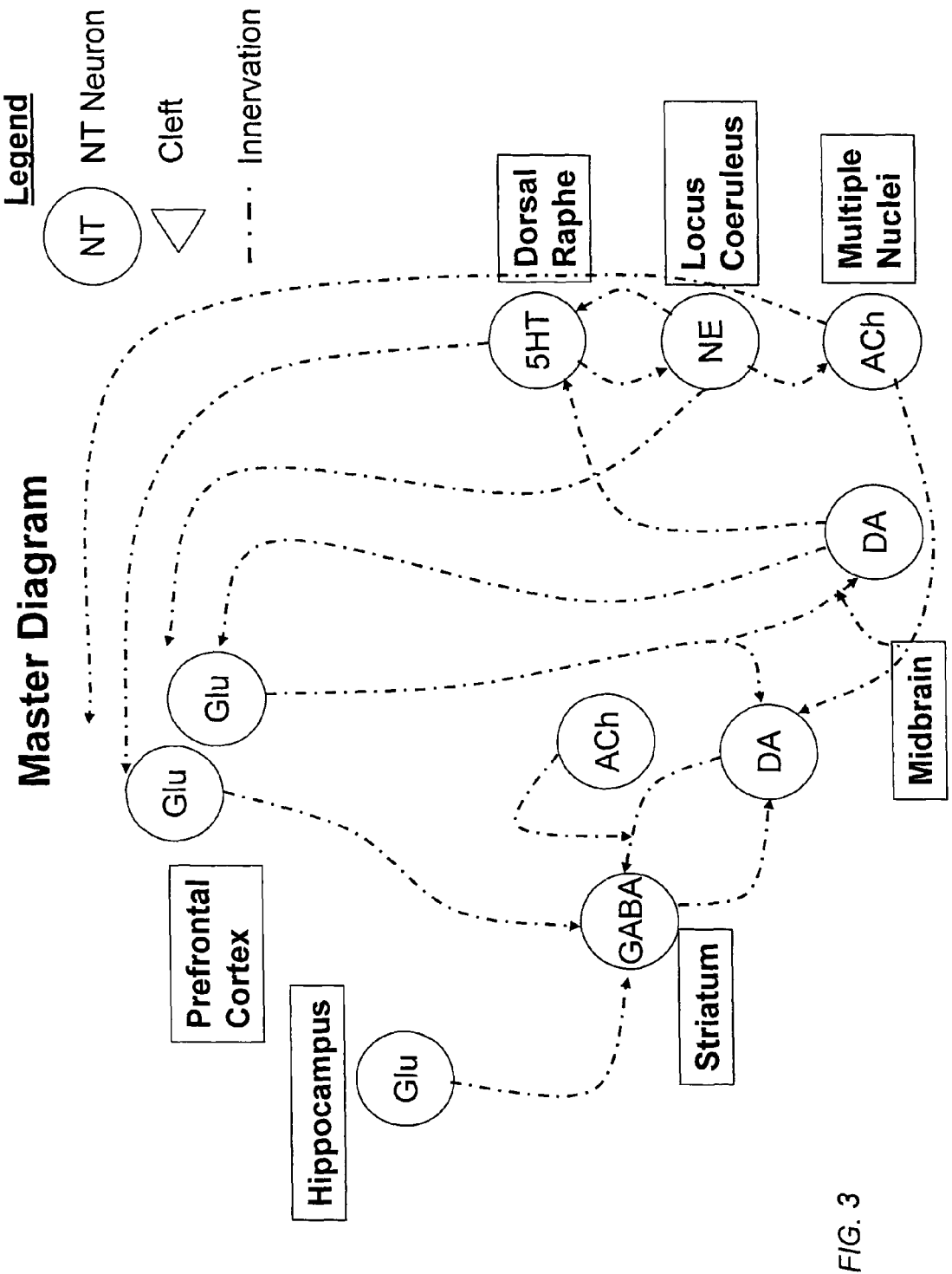
FIG. 3. Shows a schematic of the simulation modules which consists of a number of interconnected brain regions, known to play a role in psychiatric or cognitive diseases.

FIG. 3 shows the system simulation modules consisting of a number of interconnected brain regions, known to play a role in psychiatric or cognitive diseases. The dorsal striatum receives input from the dopaminergic neurons arising from the substantia nigra and afferent glutamate fibers arising from the Supplemental Motor Area in the cortex. The medium spiny striatal neurons project to the thalamo-cortical pathway of the motor circuit. The ventral striatum receives dopaminergic input from Ventral tegmentum Area and afferent glutamatergic fibers from prefrontal association cortices, hippocampus and amygdala. The medium spiny striatal neurons projects to the thalamic nuclei which form a closed cortico-striato-thalamic circuit. Prefrontal cortex is innervated by dopaminergic fibers arising from VTA, serotonergic fibers arising from Dorsal Raphe, noradrenerge fibers arising from Locus Coeruleus and cholinergic fibers originating from N. basalis of Meynert. There is a well-documented reciprocal feedback interaction between Dorsal Raphe and Locus Coeruleus.

This invention describes four mathematical models: (i) a generic receptor competition model, (ii) a model of the animal and human striatum, (iii) a model of 5HT-NE interaction and (iv) a model of the prefrontal cortex. The models are linked to each other using neuro-anatomical and neurophysiological connections.

A. Generic Receptor Competition Model

Figure 4:
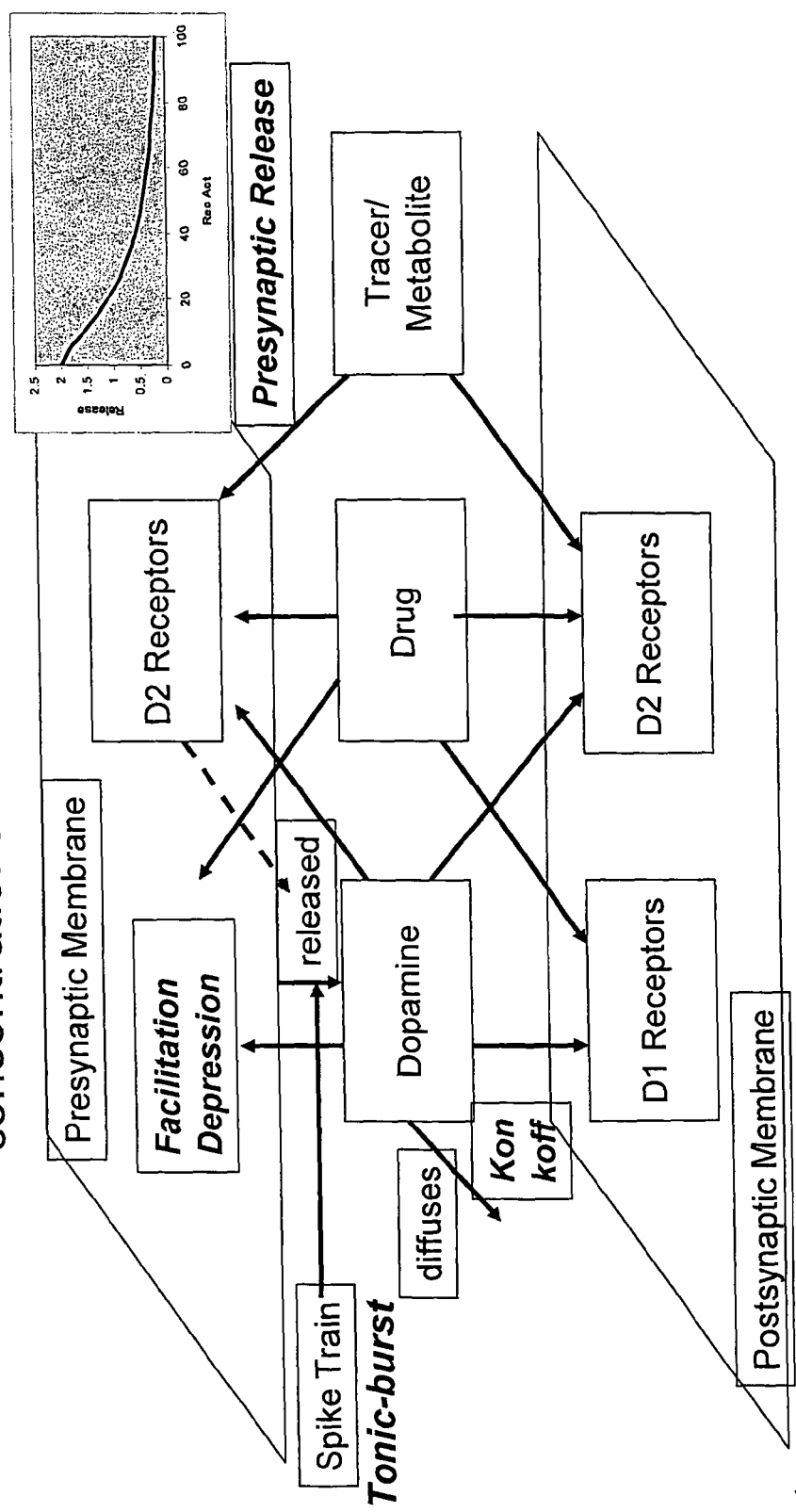
FIG. 4. Shows flow chart of the generic receptor competition model, here represented as a dopamine synapse.

FIG. 4 shows a generic receptor competition model that can be used for different types of neurotransmitter synapses, including, but not limited to, a dopamine synapse. The model is based upon a series of ordinary differential equations, which regulates the receptor activation state in different situations and accounts for: presynaptic autoreceptor regulation of neurotransmitter release; specific presynaptic firing patterns; appropriate facilitation and depression of presynaptic vesicle release; the presence of endogenous neurotransmitter and two agents competing for the same site with appropriate kon and koff values (agonist or antagonists). Unless otherwise noted, we assume kon is limited by diffusion, in 3D or 2D for a lipophilic compound; diffusion out of the synaptic cleft; re-uptake or degradation of the neurotransmitter; and the presence of low- and high affinity binding sites.

For illustrative purposes a dopaminergic synapse is shown, where dopamine interacts with the presynaptic D2-R in a negative feedback cycle and with postsynaptic D2-receptors, is degraded by the Catechol-O-methyl Transferase (COMT) enzyme and is taken up by the dopamine transporter (DAT). Neuroleptics and tracer molecules are interacting with both pre- and postsynaptic D2-receptors. The tracer possibility allows studying the interaction between for instance a parent compound and its metabolite if they both have an affinity for the D2-R (as is the case for risperidone and 9-OH risperidone). Similar models can be used for studying the dynamics at the level of the postsynaptic D1, D3, D4, D5-receptors. With the appropriate changes, specific serotonergic synapses are built with the fourteen known 5HT-3 receptor subtypes. Also, specific noradrenergic, glutamatergic and GABAergic and muscarinic synapses are constructed using the same themes. We will illustrate in some detail the dopaminergic synapse.

Dopaminergic Synapse

The number of presynaptic receptors is estimated to be 30 receptors/micron$^2$, while we assume a number of 300 postsynaptic receptors/micron$^2$. This is derived from the following arguments. $B_{max}$ of D2R in the rat striatum is about 125 fM/mg (Cai 2002), equivalent to about $8 \times 10^{16}$ molecules/l. Assuming a synaptic membrane area of 1 µm$^2$, and a volume of 1 µm$^3$, we arrive at about 100-200 molecules/synapse. Furthermore, 25-30% of these receptors are of the high affinity type [84].

Dopamine dynamics can be determined based on the binding affinities, $K_d$, for the different types of D2 receptors. We assume $K_d$=10 nM for high affinity receptors while $K_d$=5000 nM for low affinity receptors [84]. We assume that the binding rate is diffusion limited and that this depends upon the size and molecular weight of the molecules (see Table I). As a consequence, the unbinding rate is calculated by $k_{on} \times K_d$. For DA binding to the D1 receptor, $K_d$ values for both low and high affinity receptors are about 4 times higher ([89], [33]). Given the concentration of free high affinity receptors, [$D_h$], and free low affinity receptors, [$D_l$], the concentration of dopamine bound to these receptors, [$D_{hb}$] and [$D_{lb}$], respectively can be calculated using classical Ordinary Differential Equations (ODE).

The dopamine transporter pumps dopamine out of the cleft and follows Michaelis-Menten kinetics. The maximum uptake rate, $k_{max}$, of the transporter is 4.74 nM/ms (Schmitz, 2001). The dopamine concentration, $K_m$, at which the transporter works at half its maximum, is 890 nM (Schmitz, 2001). In order for the dopamine concentration to go to zero within one second after release, the number of transporters, N, in a single cleft within the striatum is 500.

The COMT enzyme breaks down dopamine at a maximum rate, $k_{max}$, of 200 nM/ms. The dopamine concentration, $K_m$, at which the enzyme is half effective is 440 microM (Yan, 2002). In order for the COMT to have an effect at these low rates, many enzymes, N, must be present. In this simulation we consider 7800 enzymes within the cleft. Breakdown of dopamine by the COMT enzyme is modeled via Michaelis-Menten kinetics so that dopamine within the cleft, [dop], follows a simple ODE. The very large value of Km makes the COMT enzyme very inefficient. The density of COMT enzymes is dependent upon the brain region, i.e. in the striatum it is much less important than the DAT, while the COMT effect in the Prefrontal Cortex tends to be more important, producing more regulation than the DATs, which are less dense in the PFC.

Drug binding dynamics can be determined based on their binding affinity, $K_d$, for the D2 receptors. Table I gives information on $K_d$, $k_{on}$, and $k_{off}$ rates for the different drugs [81]. The binding on rate is assumed to be diffusion controlled. The $k_{off}$ rate is then calculated as $k_{on} \times K_d$. The Stokes-Einstein equation determines that the diffusion constant is inversely related to the first power of the radius (the third root of the mass), therefore from a constant diffusion for all neuroleptics, we can determine the Kon rate based upon their molecular weight, which are in the 312-448 dalton range (dopamine MW is 189.4). Quetiapine is an exception with a molecular weight of 883 dalton.

TABLE 1

$K_{on}$ and $K_{off}$ rates for different compounds at the D2-R. Calculations are based upon diffusion controlled $k_{on}$ rates and $K_{off}$ rates calculated as $k_{on} \times K_i$.

| Compound | MW (Dalton) | $K_d$ (nM) | $K_{on}$ (nM/sec) | $K_{off}$ (sec$^{-1}$) |
|---|---|---|---|---|
| Risperidone | 410.9 | 3.0 | $1.10 \times 10^{-4}$ | 0.0003300 |
| Paliperidone | 426.1 | 4.1 | $1.09 \times 10^{-4}$ | 0.0004469 |
| Clozapine | 326.8 | 160 | $1.19 \times 10^{-4}$ | 0.0190400 |
| Olanzapine | 312.2 | 20 | $1.20 \times 10^{-4}$ | 0.0024000 |
| Aripiprazole | 448.4 | 1.64 | $1.07 \times 10^{-4}$ | 0.0001754 |
| Quetiapine | 883 | 360 | $0.85 \times 10^{-4}$ | 0.0289000 |
| Zyprasidone | 467.2 | 4 | $1.05 \times 10^{-4}$ | 0.000420 |
| Haloperidol | 530.1 | 1.21 | $1.01 \times 10^{-4}$ | 0.00012 |
| Raclopride | 347.2 | 90 | $1.16 \times 10^{-4}$ | 0.0104 |
| IBZM | 404.2 | 160 | $1.10 \times 10^{-4}$ | 0.0176 |
| Dopamine | 189 | 10 (high aff) | $1.42 \times 10^{-4}$ | 0.0014200 |

Given the concentration of free D2 receptors, $[D_f]$, one can determine the concentration of receptors bound by the drug, $[D_b]$.

Tracer binding dynamics can be determined based on their binding affinity, $K_d$, for the D2 receptors. For instance raclopride has an affinity of 95 nM and IBZM of 160 nM for the D2-R. Note that the affinity of the tracers is much lower than neuroleptics such as haloperidol, risperidone and olanzapine, however, they have a higher or equal affinity compared to compounds like clozapine and quetiapine. This can substantially influence the interpretation of the tracer PET data. Similar differential equations describe the time-dependence of the tracer binding dynamics.

Dopamine is released from the presynaptic membrane every time the dopaminergic nerve fires. In this model, we do not track ion movements which would take another level of complexity. Therefore, instead of using internal Ca$^{++}$ levels to determine release, we consider the facilitation and depletion of dopamine release based on the amount of time elapsed since the previous firing along the lines of Montague et al. [70]. The maximum facilitation enhancement, $w_f$, is 10% and decays exponentially at a rate, $k_f$, of ¼ sec$^{-1}$. The maximum depletion weight, $w_p$, is 3% and decays exponentially at a rate, $k_p$, of ⅕ sec$^{-1}$.

At time zero, the first firing occurs so that $t_1=0$. Later firings are determined based on the firing frequency f so that the time of the n$^{th}$ firing can be calculated. The amount of dopamine released is based upon the history of firing.

D2 receptor occupation at the presynaptic membrane affects the amount of dopamine released. Because the D2 receptor is a G-coupled protein, its effect is not immediate. Thus, when the time for release comes, we determine the effect based upon how many receptors were bound, B (both high and low affinity), 150 ms earlier. The typical number of bound receptors is $B_0$. We use a Hill equation to model the effect of the D2 receptor with a maximal effect of 25% at full D2-R block.

Free dopamine vanishes from the cleft primarily via diffusion. Because we do not consider any spatial properties, we model diffusion via an exponential decay with a half-life, H, of 150 ms as a default value. This parameter can be adjusted so as to correspond to the specific DA kinetics in various brain regions (see further).

The simulation is initiated by first finding the equilibrium given a constant amount of free dopamine at 1000 nM. The simulation is then run for a transitory time of 5 seconds at the tonic firing rate of 5 Hz. Finally, the simulation runs for an additional 2.5 seconds during which time average binding levels are determined. When the simulation finally runs, it begins with the first 7.5 seconds in memory which helps keep all the processes determining release primed.

The clearance of DA is mostly determined by the half-life as a free parameter. A number of papers have given estimates for this value. In mice [17], the rate of clearance ($V_{max}/K_m$) for N. accumbens core was determined to be 8 sec$^{-1}$ and 4 sec$^{-1}$ for N. accumbens shell. For DAT KO mice the clearance values are 0.03 and 0.04 sec$^{-1}$ respectively. Cocaine reduces clearance rate to about 0.35 sec$^{-1}$ in wild-type mice. Clearance of DA from medial PFC is about 8.3 times slower than from N. accumbens [102, 75], and at least two mechanisms have been identified (DAT/NET and MAO). DAT/NET accounts for about 40-70% of DA clearance [102]. In mouse dorsal striatum, uptake is 60% faster than in N. accumbens (110) giving a clearance rate of 12.8 sec$^{-1}$ or a DA half-life of 54 msec. The same article suggests that clearance is enhanced 33% by full D3-agonism and reduced by 50% by full D3 antagonism in the N. accumbens. Neuroleptics with high D3-antagonism will have an effect on DA clearance. In the mice caudate putamen, clearance is $V_{max}/K_m=2.65/0.21$ or half-life is 72 msec [65].

The processes of presynaptic habituation and facilitation are incorporated as follows (modified after [70]). When firings are close together, they facilitate the amount of release. However, when they are far apart, they depress the amount of release. If we denote the time of the n$^{th}$ firing by $t_n$, then the release amount is modified based on all previous firings as follows $$release_{new} = release \left( 1 + \sum_{i=1}^{n-1} w_f \exp[-k_f(t_n - t_i)] - w_d \exp[-k_d(t_n - t_i)] \right)$$

where $w_f$ is the facilitation weight (adjusted by "Relative increase due to firing facilitation"), $w_d$ is the depression weight (adjusted by "Relative decrease due to firing depression"), $k_f$ is the decay rate of facilitation (adjusted by the reciprocal of "Decay time of facilitation mechanism"), and $k_d$ is the decay rate of depression (adjusted by the reciprocal of "Decay time of depression mechanism"). In order to make this mechanism meaningful the following should be satisfied: $w_f > w_d$ and $k_f > k_d$. The parameters can be adjusted so that they satisfy experimental results [25].

Binding data for both D1-R and D2-R in the simulation are gathered from a dopaminergic cleft which fires at 4 Hz for 2 seconds, 40 Hz for half a second, 1 Hz for 5 seconds, 4 Hz for one second and at 80 Hz for ⅛ of a second.

Application to Other Types of Synapses

The following table illustrates the different parameters for other types of synapses

TABLE 2

List of different pre-and postsynaptic receptors for which the generic receptor competition model is implemented.

| Parameter | DA cleft | Cholinergic Cleft | Adrenergic Cleft | Serotonergic cleft |
|---|---|---|---|---|
| Pre-synaptic Receptor subtype | D2 | M2 | Alpha2A | 5HT1B |
| Post-synaptic Receptor subtype | D1, D2, D3, D4, D5 | M1, a7 nAChR, a4b2 nAChR | Alpha1A, alpha2A | 5HT1A, 5HT2A |
| Genotype | COMT | | COMT | |

Affinity of neurotransmitters for their relevant receptors

| Neurotransmitter | Receptor | Affinity (nM) | Ref |
|---|---|---|---|
| Ach | M1 | 3.4 | 63 |
| | M2 | 370 | 55 |
| | M3 | 4200 | 22 |
| | M4 | 5600 | 22 |
| | M5 | 800 | 22 |
| 5HT | 5HT2C | 27 nM | 48 |
| DA | D1 | 40 nM (high-aff) | 89 |
| | D2 | 10 nM (high-aff) | 84 |
| | D3 | 0.62 nM (high-aff) | 33 |

| Dopaminergic Cleft | | | | | | |
|---|---|---|---|---|---|---|
| Total Duration = 8300 ms | | | | | | |
| Frequency | 4 | 40 | 1 | 4 | 80 | |
| Number | 8 | 10 | 5 | 4 | 4 | |
| Parameters | Normal COMT Met/Met | Normal COMT Val/Met | Normal COMT Val/Val | SZ COMT Met/Met | SZ COMT Met/Val | SZ COMT Val/Val |
| Base Release (nM) | 500 | 500 | 500 | 400 | 400 | 400 |
| Half-life (ms) | 1300 | 900 | 500 | 1300 | 900 | 500 |
| Density of presyn D2 Receptors | 330 | 330 | 330 | 330 | 330 | 330 |
| Fraction of high affinity D2-R | 0.25 | 0.25 | 0.25 | 0.25 | 0.25 | 0.25 |
| Maximum relative change for release | 0.45 | 0.45 | 0.45 | 0.45 | 0.45 | 0.45 |
| Normal presyn binding | 4160 | 4160 | 4160 | 4160 | 4160 | 4160 |
| density of postsyn D1 Receptors | 300 | 300 | 300 | 300 | 300 | 300 |
| Fraction of high affinity D1-R | 0.25 | 0.25 | 0.25 | 0.2 | 0.2 | 0.2 |

| Serotonergic Clefts | | | | | |
|---|---|---|---|---|---|
| Total Duration = 9200 ms | | | | | |
| Frequency | 1.3 | 60 | 0.8 | 40 | 1 |
| Number | 1 | 3 | 5 | 2 | 2 |
| 5HT2A synapse Parameters | Normal | SZ | | | |
| Base Release (nM) | 1000 | 1000 | | | |
| Half-life (ms) | 500 | 500 | | | |
| Density of presynaptic 5HT1B-R | 30 | 30 | | | |
| Fraction of high affinity receptors | 0.25 | 0.25 | | | |
| Maximum relative change for release | 0.45 | 0.45 | | | |
| Normal presyn binding | 1170 | 1170 | | | |
| Density of postsynaptic 5HT2A-R | 300 | 255 | | | |
| Fraction of high affinity receptors | 0.25 | 0.25 | | | |

| Serotonergic Clefts | | |
|---|---|---|
| 5HT1A synapse Parameters | Normal | SZ |
| Base Release (nM) | 1000 | 1000 |
| Half-life (ms) | 500 | 500 |
| Density of presynaptic 5HT1B | 30 | 30 |
| Fraction of high affinity receptors | 0.25 | 0.25 |
| Maximum relative change for release | 0.45 | 0.45 |
| Normal presyn binding | 1170 | 1170 |
| Density of postsynaptic 5HT1A-R | 350 | 385 |
| Fraction of high affinity receptors | 0.25 | 0.25 |

| | Noradrenergic Cleft | | | | | |
|---|---|---|---|---|---|---|
| Total Duration = 9600 ms | | | | | | |
| Frequency | 2 | 60 | 1.5 | 40 | 1.67 | |
| Number | 1 | 3 | 9 | 2 | 5 | |
| Parameters | Normal COMT Met/Met | Normal COMT Val/Met | Normal COMT Val/Val | SZ COMT Met/Met | SZ COMT Met/Val | SZ COMT Val/Val |
| Base Release (nM) | 1000 | 1000 | 1000 | 1000 | 1000 | 1000 |
| Half-life (ms) | 910 | 630 | 350 | 910 | 630 | 350 |
| Presynaptic alpha2A density | 50 | 50 | 50 | 50 | 50 | 50 |
| Fraction of high affinity receptors | 0.25 | 0.25 | 0.25 | 0.25 | 0.25 | 0.25 |
| Maximum relative change for release | 0.45 | 0.45 | 0.45 | 0.45 | 0.45 | 0.45 |
| Normal presyn binding | 1030 | 1030 | 1030 | 1030 | 1030 | 1030 |
| Postsynaptic alpha2A density | 300 | 300 | 300 | 300 | 300 | 300 |
| Fraction of high affinity receptors | 0.25 | 0.25 | 0.25 | 0.25 | 0.25 | 0.25 |

Estimating Functional Brain Concentration of Pharmacological Agents

The generic receptor model can incorporate tracer data, available in human volunteers or patients, to determine effective functional brain concentrations of pharmacological agents. In this case, we would run the simulation first in the presence of the endogeneous neurotransmitter being targeted (for example dopamine) and the radio-active tracer (for example, $^{11}C$ raclopride), as a baseline occupancy. Next we would run the simulation in the presence of the endogenous neurotransmitter (i.e. dopamine), the drug (for example a neuroleptic binding to D2R) and the radio-active tracer. The concentration of the drug would be varied systematically until we get the appropriate displacement seen in the radio-active study. This is the most likely effective drug concentration which we then use in our further models.

B. The Dorsal Striatum Model for Extra-Pyramidal Symptoms

Figure 5:
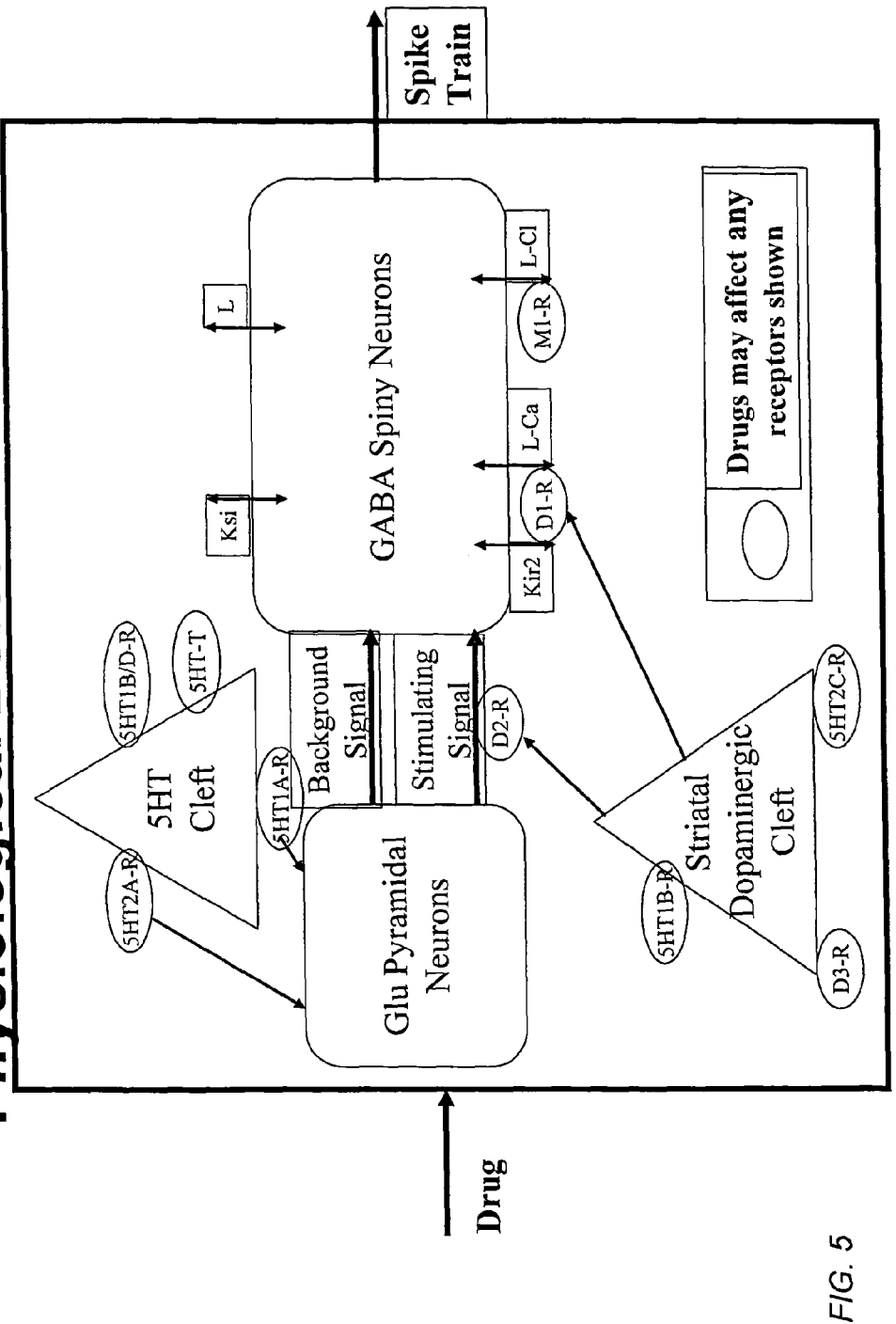
FIG. 5. Shows a diagram illustrating the various processes used in the simulation of the Extra-Pyramidal Symptoms (EPS) Model.

FIG. 5 illustrates the various processes used in the simulation of the Extra-Pyramidal Symptoms Module. The GABA spiny neuron in the dorsal striatum is the key processing unit and is driven by both glutamatergic and dopaminergic (D1) excitatory input. D2-R are presumed to act on glutamatergic synapses, modulating excitatory input into the spiny neuron. D3 and 5HT2C receptor modulate DA kinetics. M1-receptors directly modulate GABAergic neuron excitability (Ksi=slow inward K-channel, Kir2=inward-rectifier K-channel, L-Ca, L-type Ca channel, L-Cl, Chloride channel).

In the normal state, the putamen receives excitatory afferents from the motor and somatosensory cortical areas and communicates with the globus pallidus/substantia nigra pars reticulata ($GP_i/SN_r$) through a direct inhibitory pathway and though a multisynaptic ($GP_e$, STN=subthalamic Nucleus) indirect pathway. Both pathways pass through the ventral lateral thalamus (VL) to close the loop back to the cortex.

The direct output pathway links the striatum to the inhibitory internal segment of the globus pallidus ($GP_i$) and the inhibitory substantia nigra pars reticulate ($SN_r$). Activation of the direct pathway decreases the inhibitory output from the basal ganglia and disinhibits the motor thalamus, such that movement is facilitated.

In contrast, in the indirect output pathway, the medium spiny projection neurons inhibit the external segment of the globus pallidus ($GP_e$), which then sends less inhibition to the subthalamic nucleus. Disinhibiting the STN excites the internal segment of the globus pallidus ($GP_i$), leading to an enhanced inhibitory output from the basal ganglia to the motor thalamus so that movement is disfacilitated.

Dopamine is believed to modulate striatal activity, mainly by inhibiting the indirect and facilitating the direct pathways. The disinhibition hypothesis [23] suggests that in Parkinson's disease like syndromes, dopamine deficiency leads to increased inhibitory activity from the putamen onto the GPe and disinhibition of the STN. In turns, STN hyperactivity by virtue of its glutamatergic action produces excessive excitation of the $GP_i/SN_r$ neurons, which overinhibit the thalamo-cortical and brain stem motor centers. This process is assumed to be the basis of D2-R block mediated Parkinsonian symptoms (24). Blocking the D2-R, the activation of which has been shown to negatively modulate glutamnate release from cortical afferents [4] increases the GABAergic inhibition of the GPe, leading to less inhibition of the subthalamic nucleus in the indirect pathway. This disrupts the regulation of the thalamocortical connection finally leading to less excitatory control from the cerebral cortex to the brain stem and spinal cord centers involved in movement control.

Recent studies [95] have extended this model considerably and have shown that normal activity patterns in the indirect pathway are of an irregular nature. Increased (dorsal) striatal input in the indirect pathway and weakened intrapallidal inhibition drives the $GP_e$-subthalamic regions into a repetitive and rhythmic spiking pattern, the frequency of which is consistent with the movement tremor frequency. In Parkinson's patients treated for deep brain stimulation, subthalamic Nucleus frequency increased from 20 Hz to 70 Hz when patients went on L-dopa therapy and resolved their motor problems [12].

The major computational unit of the striatum (both ventral and dorsal) is the medium spiny GABA-ergic neuron (modified and extended considerably after [40]), in which dopaminergic, glutamatergic and cholinergic input fully characterizes the spike-train readout (FIG. 4).

Ach Effect on Medium Spiny Neuron

In the striatum, expression of muscarinic subtypes is mostly restricted to M1 and M4 subtypes [106], mostly on striatal medium spiny neurons [49]. M4 and D1 receptors often colocalize on spiny neurons in the indirect output pathway [106] and they have opposing actions, suggesting that this interaction might fine-tune the modulatory control of the spiny projection neurons. Muscarinic agonists have been documented to induce an inward current by reducing outward $K^+$ currents, therefore leading to depolarization and increased excitability [86]. Stimulation of the muscarinic receptors by the general agonist muscarine, as in the case of normal cholinergic stimulation, significantly reduces the inhibitory postsynaptic potentials (IPSP) in the GABAergic interneurons [54]. Blocking the muscarinic receptors with atropine restores the IPSP, leading to enhanced negative feedback on the spiny GABAergic neurons. The effect of Ach on the excitability of medium spiny GABA-ergic neurons in the striatum is complex, as two opposite effects are carried respectively by nicotinic and muscarinic receptors [54]. However, as none of the neuroleptics studied is documented to modulate any nicotinic receptor, but some of them are prominent anti-muscarinic receptors antagonist, we focus on the effect of muscarinic receptor activation on the excitability of the medium spiny neuron. This effect is carried probably by M1-R, as pirenzepine blocks this effect of muscarine in the striatum [46]. As a further confirmation, in dementia with Lewy Body disease (DLB), densities of M1-R in the striatum are significantly reduced compared to AD and normal controls and this $^3$H pirenzepine binding is inversely correlated with cortical DLB pathology [74]. Lower M1-R densities reduce the chances of muscarinic stimulation to exacerbate the EPS.

The disinhibitory effect mediated by mAchR activation is translated into a change in $g_{Cl}$ conductance according to the following sigmoid equation.

$$g_{Cl}=4*(1+0.3*M1\_block)$$

Where $g_{Cl}$ is the chloride conductance (maximal value is 4 pS). Maximal effect of muscarinic block is 30% [54], and the M1_block is calculated with the competition model of acetylcholine and neuroleptic at the appropriate concentration.

Role of 5HT2C Receptor in Dopamine Regulation

Many neuroleptics also antagonize the 5HT2C receptor to a variable degree. This receptor subtype is particularly interesting in the striatal homeostasis of dopamine. It has been shown indeed that 5HT2C receptor activation by a specific agonist Ro-60-0175 can actually reduce free DA as measured by microdialysis with a maximal effect of 30%, suggesting that this serotonergic circuit has a negative feedback effect on dopamine release and clearance (di Matteo 2002). The affinity of 5HT for the 5HT2C receptor, at least for GTP-γ-S metabolism is 27 nM (Im et al 2003). Using this value we can simulate the competition between endogenous serotonin and the neuroleptics using their appropriate affinity values. The amount of block at the 5HT2C receptor (5HT2C-block) was determined by simulating the competition at the 5HT2C receptor using the appropriate affinity of the compound and the above mentioned affinity of 5HT for the 5HT2C receptor. Because maximal stimulation of 5HT2C gives rise to a 30% decrease in free DA (Di Matteo 2002), the amount of free DA was then calculated as $$Free\_DA=Basal\_DA(1+0.3*5HT2C\text{-block})$$

Due to the relative affinities of the neuroleptics under consideration in relation to the affinities for 5HT, it turns out that the above formula can be simplified to $$Free\_DA=Basal\_DA\{1+0.3*Conc/(Conc+K_i)\}$$

where $K_i$ is the affinity of the neuroleptic against the 5HT2C receptor.

Activity at the D3-receptor also influences DA [110]. Basically, full D3-R activation increases clearance of dopamine more in the ventral striatum than in the dorsal striatum. This effect is modeled as a linear interpolation with a maximum of 30%.

Figure 6:
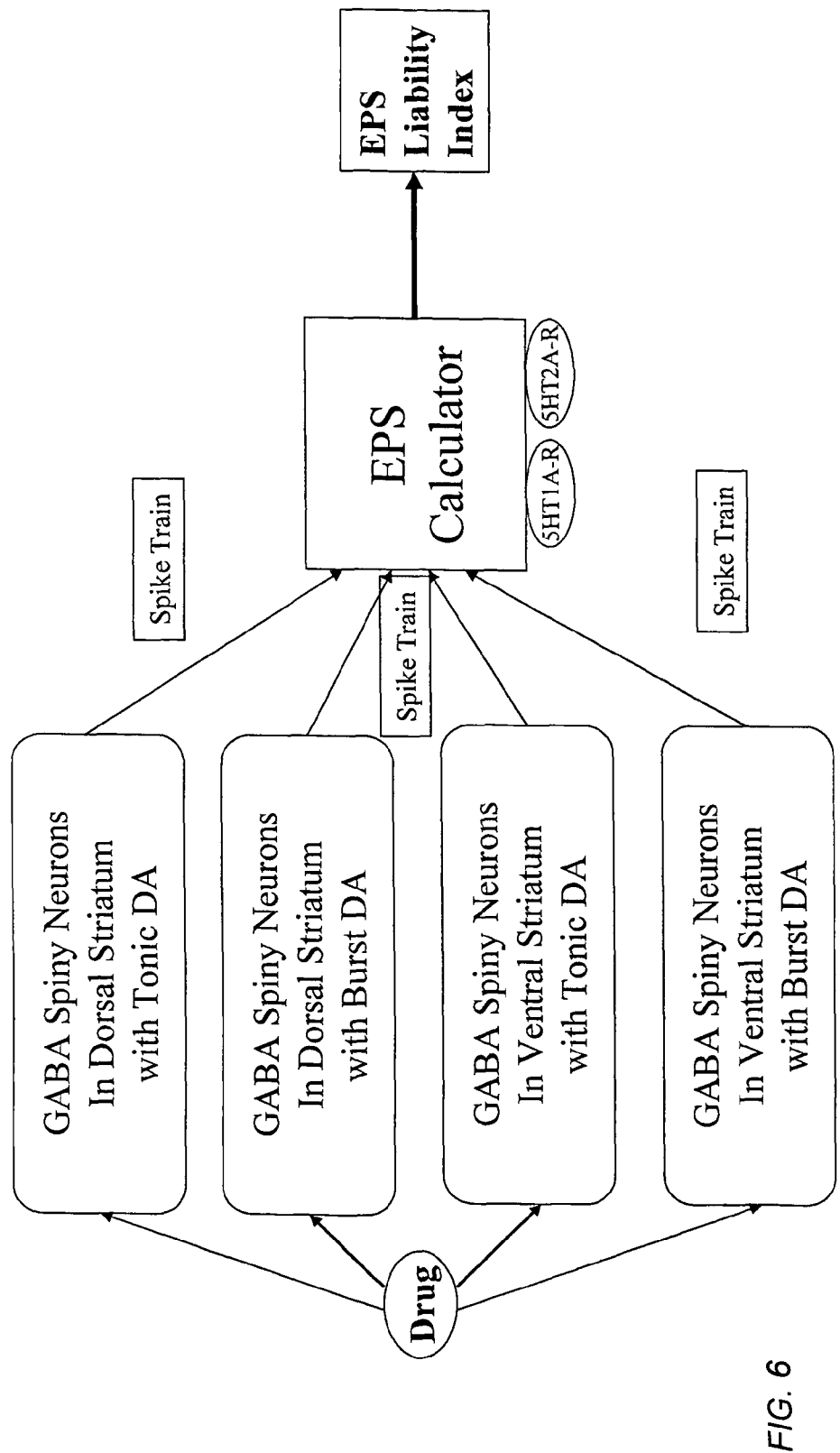
FIG. 6. Shows a flow chart of how the EPS liability index is calculated.

FIG. 6 shows how the EPS liability index is determined. First the effect of drugs on spike train frequencies is calculated in 4 different conditions. A mathematical formula (see below) combines these outcomes together with a convolution based mupno prefrontal serotonin receptor activation to yield the final EPS Liability Index.

The EPS Liability Index (FIG. 5) is finally calculated as the $$EPS\ LI=(\text{dorsal striatum firing})^2 \times (1+PFC\_Thr^2)/ [\text{ventral striatum firing}].$$

Correlation Between Outcome of the Model and Actual Clinical Scales

Figure 7:
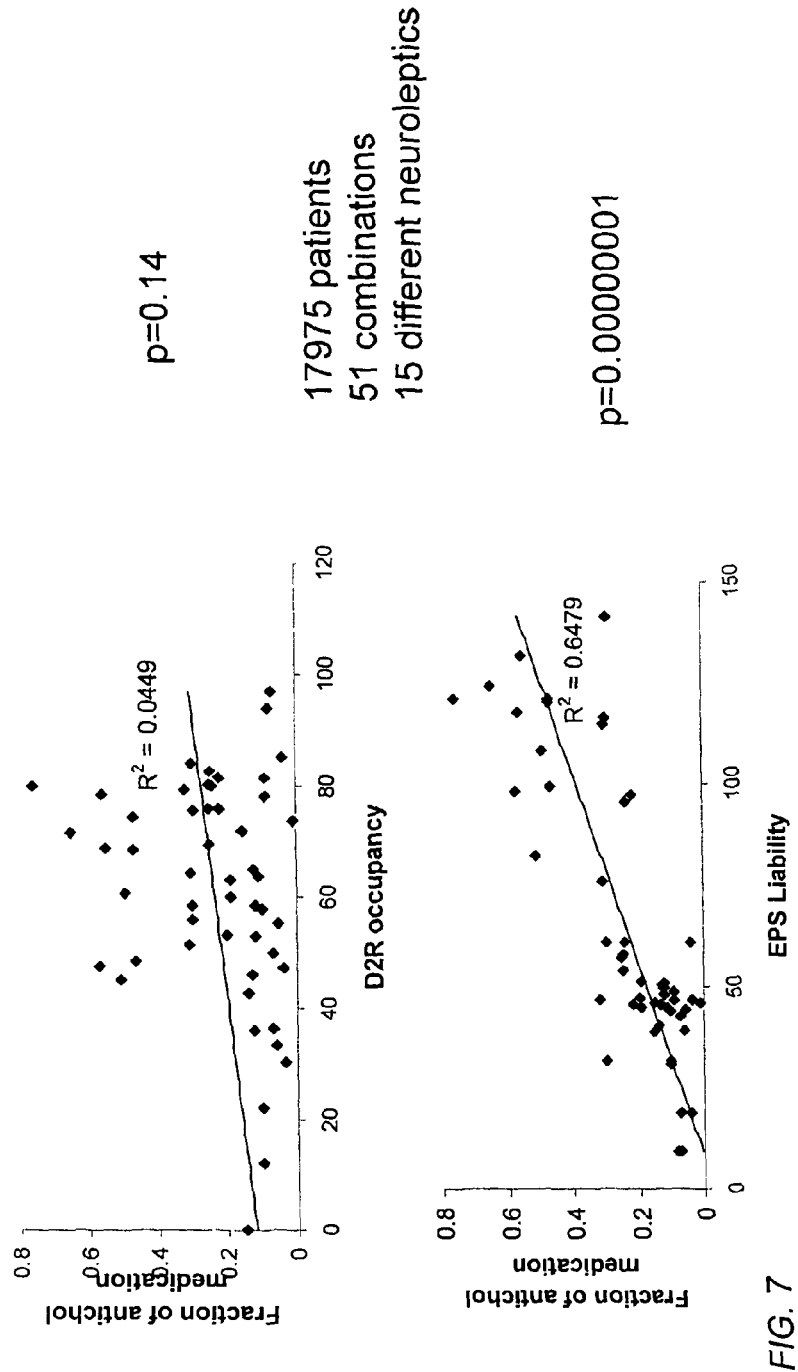
FIG. 7. Shows a graph of the need for anticholinergic medication and D2R occupancy.

We used the clinical database to gather information on various clinical scales related to motor side-effects. For instance, the parameter 'fraction of patients needing anticholinergic medication' was a readout of motor side-effects during clinical trials of schizophrenia (see FIG. 7). We compared the outcome of 51 neuroleptic-dose combinations covering 15 different neuroleptics and showed that the outcome of our EPS module had a correlation $r^2$ of 0.64 (r=0.8) compared to a correlation $r^2$ of 0.045 (r=0.21) for the relation with the simple D2R occupancy, which has been used sofar. This table 3 gives the comparison between the correlations for various other clinical scales related to motor side-effects.

TABLE 3

Performance of the EPS module in predicting the known clinical effects. For each clinical scale, the correlation and p-value is given for the D2R occupancy rule and for the outcome of our simulation modules.

| Scale | D2R corr($r^2$) | D2R p-value | EPS corr($r^2$) | EPS pval |
|---|---|---|---|---|
| Fraction of patients on anticholinergic medication | 0.02 | 0.34 | 0.65 | 0.00001 |
| Change SAS vs baseline | 0.02 | 0.326 | 0.41 | 0.00007 |
| Fraction of patients worsening on SAS | 0.00 | 0.8482 | 0.57 | 0.0014 |
| Anticholin medication (dose) | 0.41 | 0.0209 | 0.14 | 0.2258 |
| EPS syndrome (fraction) | 0.06 | 0.0734 | 0.12 | 0.0130 |
| Hypertonia (fraction) | 0.01 | 0.7393 | 0.00 | 0.8709 |
| dystonia (fraction) | 0.03 | 0.3153 | 0.28 | 0.0023 |
| Tremor (fraction) | 0.00 | 0.9192 | 0.27 | 0.0027 |
| Parkinsonism (fraction) | 0.06 | 0.2917 | 0.06 | 0.2665 |
| Fraction of patients with hypotonia | 0.17 | 0.1240 | 0.53 | 0.0018 |
| Fraction of patients with dyskinesia | 0.00 | 0.9492 | 0.15 | 0.0862 |
| Change on Barnes Akathisa scale | 0.01 | 0.5988 | 0.19 | 0.0144 |
| Fraction of patients with akathisa | 0.01 | 0.5908 | 0.00 | 0.8428 |
| AIMS change from baseline | 0.06 | 0.2668 | 0.14 | 0.0956 |
| AMS Final change | 0.00 | 0.8719 | 0.03 | 0.4128 |
| Change on total ESRS | 0.06 | 0.4758 | 0.09 | 0.3536 |
| Change on ESRS Parkinsonism | 0.20 | 0.1256 | 0.13 | 0.2270 |
| Change in ESRS hyperkinesia | 0.00 | 0.8823 | 0.16 | 0.3207 |
| Change on ESRS dystonia | 0.00 | 0.9523 | 0.01 | 0.8014 |
| Change on ESRS Dyskinesia | 0.19 | 0.2631 | 0.01 | 0.8030 |
| | | # of significant | | # of significant |
| Average | 0.07 | 1 | 0.19 | 6 |

Figure 8:
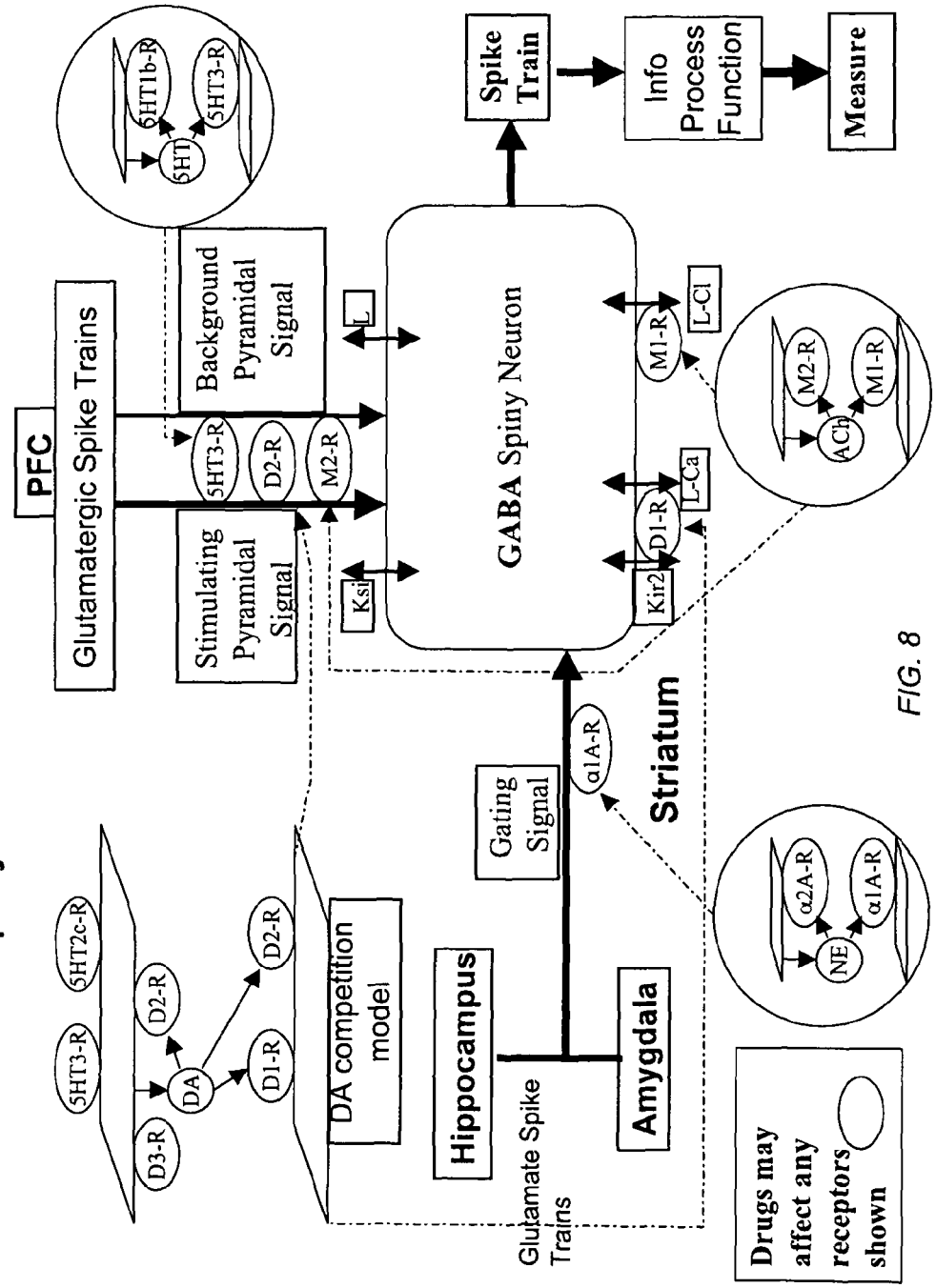
FIG. 8. Shows a flow chart of the computer model of the interactions between and among cortical and sub-cortical brain regions yielding a signal to noise type output as a model for clinical efficacy.

C. The Ventral Striatum, Prefontal Cortex, Hippocampus Model with Output for Predicting Clinical Efficacy of Drugs This model is constructed using a model of the GABAergic spiny neuron, which is the major neuron subtype in both the dorsal and ventral striatum. FIG. 8 shows the major processes contributing to the medium spiny neuron model. The model readout is a function reflecting information content change between incoming and outgoing action potential train. Different receptor subtypes can be modulated by neuroleptics. We implement in a quantitiative fashion the ideas about signal-to-noise changes observed in schizophenic patients and their unaffected siblings [105].

The GABA spiny neuron originates in the striatum and is stimulated in large part due to Glu neurons from the PFC. In this simulation, we allow the following currents to affect the neuron: slowly inactivating potassium (Ksi), inward rectifying potassium (Kir2), L-type calcium (L-Ca), a general passive leak (L) and a specific passive Cl leak (L-Cl). A spike train is generated based on time and the neuron's membrane potential. The Signal is the amount of action potentials coming out of the medium spiny neuron in the pathological state over a period of five seconds with the neuroleptics present at the appropriate concentration. The GABA spiny neuron has many Glu connections, with a baseline synaptic conductance density of 10.5 uS/cm^2. This translates to a maximum conductance of 10.5 pS given the dimensions of our neuron. Due to the great innervation, we allow firing to occur every 3 ms. In order to reach the initial density, we also assume that the decay in signal is 3 ms. In the simulations, the background signal begins 100 ms after the simulation begins to allow the cell to be close to equilibrium before being stimulated.Gating input (originating from various brain regions, such as hippocampus and amygdala) is provided at frequencies of 330 Hz.

Glu Signal

We assume that there are 20 Glu neurons responsible for getting the medium spiny neuron to fire correctly. Under the "noise" condition, we assume that these neurons behave like the ones described above firing at 6 Hz with a strength of 4.8e-6. Under the "signal" condition, we assume that the frequency goes to 30 Hz and they fire simultaneously in two groups. This translates to 60 Hz input, but with a strength of 5*4.8e-6. In addition to the background Glu signal, there is a stimulating Glu signal which tries to make the GABA spiny neuron fire in response. Once again, due to the high Glu innervation, we assume a stimulation every 3 ms with a decay of 3 ms. The critical conductance which changes behavior of the cell is 2.8 pS. Thus, in order to get rich dynamics, we assume a conductance of 3.35 pS. We assume that there is always some noisy input from Glu inputs. We assume that it consists of 40 neurons firing at 6 Hz which means that if they are evenly spread out, we have an input of 240 Hz. The strength of the gating signal is 4.8e-6. In the simulations, the stimulating signal begins at 250 ms to allow the background stimulation to affect the cell. This stimulation then continues to the end (at 5 seconds). The glutamatergic signal input from the PFC is a 50 Hz signal. Activation of postsynaptic D2R on glutamatergic afferents (which decreases glutamatergic activation of the spiny neuron) is modulated by means of the receptor competition model (see above) and is dependent upon the particular concentration of neuroleptics. D2 activation decreases this stimulating Glu signal by reducing the signal's conductance. We assume a simple linear relation which allows ventral spiking in the control case, but not as much in the SZ case. If there is no D2 activation, then the conductance is 3.35 pS. However, if the activity is at the very high percentage of 60%, the conductance drops to 1.85 pS. Activation of postsynaptic D1R on the spiny neuron affects Kir2 and L-Ca currents and modulates the glutamatergic drive such that concomitant stimulation drives the spiny neuron in the upstate, allowing it to fire. Kir2 and L-Ca currents are both multiplied by a dopaminergic factor called u. u is determined by D1 activation for both tonic firing and burst firing. Both patterns repeat at 4 Hz. However, tonic firing is depicted by a relatively slow increase to u_max (rate ~25 ms) and an almost immediate decrease from the max, but once again slowly (rate ~50 ms). Burst firing on the other hand is depicted by a rapid increase to u_max (rate ~1 ms), followed by a long duration at this maximum (~00 ms) finally followed by an even slower decay (rate ~100 ms). In the case of tonic firing, u_max is determined from the average D1 receptor activation for the first firing pattern (@ 4 Hz), third firing pattern (@ 1 Hz) and fourth firing pattern (@ 4 Hz). In the case of burst firing, u_max is determined from the average D_receptor activation for the final firing pattern (@ 80 Hz). u_max is 0.8 plus 0.006 times the D1 receptor activation. (Note: D1 receptor activation is the percentage of D1 receptors bound by DA and as such varies between 0 and 100.) This dopaminergic signal begins 500 ms into the simulation (to allow the signal to establish itself) and stops 500 ms before the end. High D1 activation amplifies strong signals and diminishes weak signals. We assume that the "noise" condition has tonic DA activity while the "signal" condition has burst DA activity.

The Hippocpampus and Amygdala

The gating signal from the hippocampus and amygdala is a high frequency, low strength glutamatergic input. The gating signal from the amygdala is under the influence of adrenergic pharmacology [10], so that alpha1A-R activation tends to strengthen the gating signal. The model allows to flexibly adapting the gating signal input from the hippocampus, so that network simulations similar to the prefrontal cortex network can be developed as front-end input modules to the SN module. It would be envisageble at some point to incorporate concepts related to the SOCRATES (Sequences of Condensed Representations, Autocorrected, Theta Gamma Coded in Context) model [59].

The muscarinic M1R couples to the chloride channel, regulating the membrane potential. The model calculates the timing of action potential, when the membrane potential exceeds a certain membrane threshold. Blocking of the M1 receptor causes a modest increase in the conductance of the Cl⁻ leak current. A maximum block of 100% would cause the conductance to increase by 30%. However, because ACh has such a strong affinity for M1-R, the maximum block would more practically be ~20% which would have a maximum increase on the conductance of ~6%.

The output is captured as an information content parameter (see below). Basically, this parameter describes the quantity of encoded bits in the action potential train, which is proportional to the amount of information a network can handle. Therefore the difference between input and output is a useful readout as it is proportional to the information processing capacity in the ventral striatum, and represents a type of signal to noise readout.

We introduce a schizophrenia pathology as follows. PET imaging studies indicate that certain parameters are changed between the healthy state and the schizophrenia pathology. As an example, using alpha-methyl-para-tyrosine induced acute dopamine depletion, PET imaging with $^{11}C$ raclopride in normal controls and schizophrenia patients indicated that free dopamine in patients was essentially double the value for normals controls [2]. Such experiments also provide us with degrees of variability for the patient population. For a population of already treated schizophrenic patients, the values are

TABLE 4

Parameters used for defining a pathological state of the simulation modules.

| Parameter | Change vs. healthy | Variation | Reference |
|---|---|---|---|
| DA released | +100% | CV = 20% | [2] |
| D1-R | No change | CV = 35% | [1] |
| D1-R high affinity | −20% | N/A | [53] |
| D2-R | +30% | CV = 50% | [85] |
| D3-R | No change | CV = 30% | [42] |
| DAT | −30% | CV = 35% | [57] |
| M1-R | No change | CV = 40% | [82] |
| M2-R | No change | CV = 40% | [82] |
| 5HT2C-R | −20% | CV = 40% | [98] |

In addition, we assume that the Noisy Glu Signal and the Glu Signal are both affected by D2-R activation. In the case of schizophrenia, the signal strength is reduced by 20%.

The model parameters can be adapted so as to improve correlations with specific clinical scales, leading to slightly different models for the different scales (i.e. PANSS positive or PANSS negative). This suggests differential weights to specific neurotransmitter circuits or pathways which are involved with specific clinical scales.

Performance of the Schizophrenia (SN) Module in Correlation Studies

Figure 9:
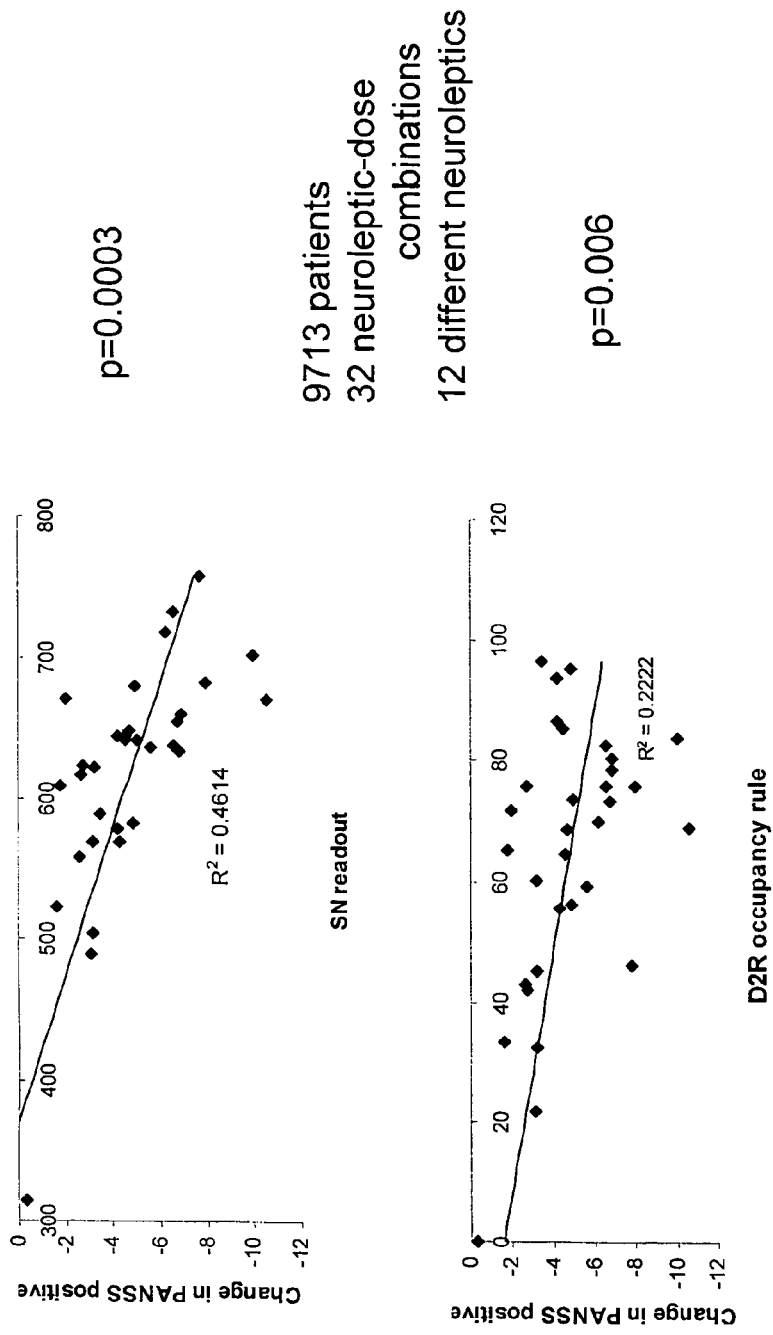
FIG. 9. Shows graphs of output from the Signal to Noise Model and observed changes on the.clinical PANSS positive scale, and the D2R occupancy and observed changes on the.clinical PANSS positive scale.

FIG. 9 illustrates the correlation between the outcome of the computational SN module and the PANSS positive scale for 35 neuroleptic-dose combinations, covering 12 different neuroleptics. In this particular case, correlation with simple D2R occupancy yields a correlation coefficient $r^2$ of 0.22, suggesting a reasonable contribution of DA pharmacology to the clinical outcome. However, the correlation between PANSS positive and the outcome of the SN computer model is 0.46, suggesting that incorporation of additional physiology is able to substantially improve the correlation.

The following table shows the correlations between performance of drugs on clinical scales derived form the clinical database and their outcome either in (i) a D2R occupancy rule and (ii) the S/N module. The seven key clinical scales are denoted with an asterix. On average, the computer model achieves an 80% increase in correlation values, because it takes into account the physiological effects at more than 10 receptors.

TABLE 5

Performance of the SN module in comparison to the D2R occupancy rule. For each clinical scale, the correlations and p-value for both models are given. The average correlation coefficient for the SN module is 0.358 compared to 0.20 for the D2R occupancy rule.

| Change in Clinical Scale | correlation D2R ($r^2$) | p-val | correlation S/N ($r^2$) | p-val |
|---|---|---|---|---|
| *PANSS total | 0.183 | 0.0178 | 0.625 | 0.0000 |
| *PANSS positive | 0.222 | 0.0062 | 0.461 | 0.0000 |
| PANSS negative size effect | 0.429 | 0.0666 | 0.886 | 0.0001 |
| *PANSS negative | 0.190 | 0.0138 | 0.725 | 0.0000 |
| Size effect in PANSS disorg | 0.125 | 0.3818 | 0.023 | 0.7162 |
| PANSS psychopatholgy | 0.188 | 0.0549 | 0.402 | 0.0024 |
| PANSS Anxiety/depression | 0.308 | 0.1114 | 0.480 | 0.0316 |
| *SANS | 0.200 | 0.213 | 0.366 | 0.0011 |
| *BPRS total | 0.375 | 0.0000 | 0.382 | 0.0000 |
| Size effect in BPRS total | 0.089 | 0.2776 | 0.226 | 0.0109 |
| BPRS core items | 0.256 | 0.1549 | 0.629 | 0.0016 |
| *BPRS postive | 0.313 | 0.0078 | 0.474 | 0.0008 |
| *BPRS negative | 0.673 | 0.0023 | 0.802 | 0.0000 |
| BPRS activity | 0.060 | 0.3257 | 0.162 | 0.0868 |
| BPRS anergia | 0.136 | 0.1178 | 0.214 | 0.0371 |

TABLE 5-continued

Performance of the SN module in comparison to the D2R occupancy rule. For each clinical scale, the correlations and p-value for both models are given. The average correlation coefficient for the SN module is 0.358 compared to 0.20 for the D2R occupancy rule.

| | | | | |
|---|---|---|---|---|
| BRPS anxiety/depression | 0.007 | 0.7417 | 0.010 | 0.6923 |
| BPRS hostility | 0.024 | 0.6307 | 0.104 | 0.0773 |
| BPRS Thought disturbance | 0.065 | 0.3784 | 0.182 | 0.1245 |
| CGI-S improvement | 0.061 | 0.1599 | 0.078 | 0.0594 |
| CGI-Global improvement | 0.038 | 0.6681 | 0.164 | 0.0145 |

| Summary | | # of significant | | |
|---|---|---|---|---|
| | 0.20 | 7 | 0.358 | 14 |
| | 0.67 | 2 | 0.864 | 9 |

D. Serotonin-Norepinephrine Interaction

Figure 10:
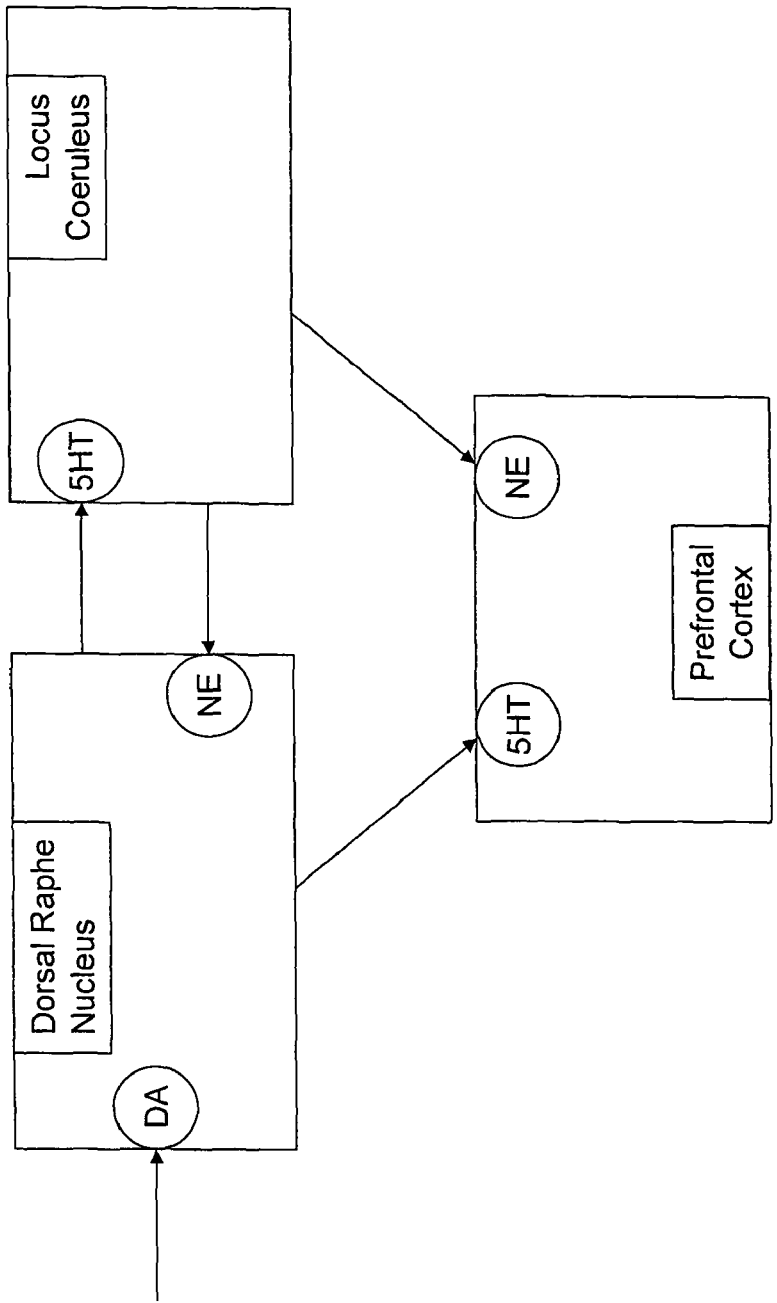
FIG. 10. Shows a flow chart of the interactions between Dorsal Raphe Nucleus; Locus Coeuruleus, and efferent projections to the PFC or hippocampus.

FIG. 10 shows a flow chart of the interactions between Dorsal Raphe Nucleus, source of serotonergic neurons; Locus Coeuruleus, source of noradrenegric neurons and efferent projections to the PFC or hippocampus. The activity of the Dorsal Raphe Nucleus is regulated by afferent DA fibers from VTA (D2R), serotonergic 5Ht1A autoreceptors and alpha1A receptors from Locus Coeruleus. The activity of LC is regulated by afferent 5HT2 receptors from DR and noradrenergic alpha2A autoreceptors. This gives rise to a highly non-linear circuit.

This computer model for serotonin-noepinephrine interaction simulates the effect of neuroleptic drugs on the serotonin and noreprinephrine free level in the prefrontal cortex, based on the interaction between serotonergic neurons in the Dorsal Raphe Nucleus and noradrenergic neurons in the Locus Coeruleus. The pharmacology of drugs is modeled at three synapse levels: a serotonergic synapse onto noradrenergic cell bodies in the LC; an adrenergic synapse onto serotonergic cell bodies in the DR and a serotonergic presynaptic terminal ending in the PFC or hippocampus.

Serotonergic Synapse onto NE Cell Bodies in LC

The serotonergic synapse in the Locus Coeruleus originates in the Dorsal Raphe Nucleus. Serotonin released here activates postsynaptic 5HT2A receptors on the cell bodies of noradrenegric neurons and negatively influences the action potential firing frequency. Notably, full elimination of 5HT innervation by lesioning the Dorsal Raphe increases NE firing frequency from 2.0 to 3.5 Hz, i.e. by 75% [43]. This effect is very likely mediated by 5HT2A receptors [91]. If S(t) is the concentration of serotonin in the cleft at time t, we model the activation A(t) of the 5HT2A receptor by $$A(t) = c\, D\, S(t)/[K_i + S(t)]$$

where $K_i$ (Ki=20 µM), is the concentration of serotonin in which 50% of the 5HT2A receptors are occupied (McAllister 1992), c is a user controlled parameter adjusting the relative amount of 5HT2A receptors being used, (c=1). Furthermore, D is the amount of inhibition (e.g. due to drugs) at the 5HT2A receptor (a value between 0=full inhibition and 1=no inhibition).

We define $t_n$ as the global time at which the $n^{th}$ firing takes place, $T_n$ as the time period of the $n^{th}$ firing of the Locus Coeruleus, and $T_o$ as the base period between firings. Because the normal firing frequency is 2 Hz, $T_o=1000/2=500$ ms. The accumulation of 5HT2A receptor activation during the period of the (n−1) firing, can be defined as $$I_n = \int_{t_{n-1}}^{t_{n-1}+T_{n-1}} A(t)dt$$

$I_o$ is the average accumulation of 5HT2A activity in the case where all neurons are firing monotonically. Having determined, $I_n$ we can calculate the time period for the $n^{th}$ firing as follows:

$$T_n = T_o\left(4 + 6\frac{I_n^s}{I_n^s + I_o^s}\right)\left(\frac{1}{7}\right)$$

where s is the sensitivity to change for the 5HT2A receptor. s ranges between 0 and 1 where 0 means no change and 1 means maximal sensitivity to change. (s=0.5 by default).

When the 5HT2A receptor is fully inhibited (A=0=>$I_n$=0), the firing frequency is increased by 75%. The time period is calculated every time the Dorsal Raphe fires. Future models may take a stochastic approach and rely on a history of 5HT2A activity.

Serotonin can disappear from the cleft through diffusion or its interactions with enzymes and receptors which we do not explicitly include. For simplicity, we assume that the rate of dissipation is proportional to the amount of serotonin in the cleft.

$$\frac{\partial S(t)}{\partial t} = -kS(t)$$

S(t) is the concentration of serotonin in the cleft at time t, whereas k is the rate of exponential decay. Studies on diffusion of DA show that it has a half-life of about 500 ms [26]. We assume the diffusion of 5HT is similar. Thus, we let k=ln(2)/500.

Noradrenergic Synapse into 5HT Cell Bodies in DR

Whenever an action potential arrives at the presynaptic membrane of a Locus Coeruleus neuron synapsing on a serotonergic neuronal cell body in the Dorsal Raphe Nucleus, norepinepherine is released into the noradrenergic cleft.

The concentration N(t) of Norepinephrine in the synaptic cleft at time t is $$N(T)=N(T-dt)+b_N$$

where T is the time an action potential arrives at the Locus Coeruleus, dt is the step size in time and $b_N$ is the concentration of norepinephrine released into the cleft. Although there are no data out for NE release in neuronal cells, we assume that the amount of neurotransmitter released is similar to the amount of released serotonin (see below), i.e. about 5000 molecules.

Given the concentration of norepinephrine in the cleft and the concentration of postsynaptic $\alpha_1$ receptors, we can determine the occupancy $\alpha_1(t)$ of the $\alpha_1$ adrenergic receptors based on the $K_i$ values (the concentration of norepinephrine in which 50% of the $\alpha 1$ receptors are occupied) which describe the affinity of NE for $\alpha_1$. An estimated value of $K_i$ is 4.5 µM [71].

$$\alpha_1(t)=A_1*\{N(t)/[N(t)+K_i]\}$$

$A_1$ is the concentration of $\alpha_1$ receptors. An estimation for this parameter can be deduced from autoradiography data of specific $\alpha_1$ adrenoceptor ligands. Using $[^{125}I]$ HEAT ($[^{125}I]$iodo-2-[beta-(4-hydroxyphenyl)ethylamino methyl]), two sites with different affinities for the alpha 1-adrenoreceptor were found in normal rat brain in vivo: a high-affinity site with $K_d$ (half-saturation constant) of 3.6±0.7 nM, and a low-affinity site with $K_d$ of 668±552 nM. The density ($B_{max}$) of the high-affinity site in different brain regions varied from 2.2±0.8 to 14.6±0.6 pmole/g, while the low-affinity range was 149±44 to 577±30 pmole/g [36]. In a human study using biopsies from epileptic and non-epileptic foci, receptor-binding assays were performed on isolated cortical membranes using [$^3$H]prazosin. Values in nonspiking regions (i.e. non-affected regions) for $B_{max}$, are 218.8±15.6 fmol/mg protein with a corresponding affinity of 0.17±0.04 nM [11]. To go form this value to a density of synaptic receptors, we acknowledge that 10 fM/mg tissue is 6×10$^9$ molecules/mg tissue. Assuming the density of biological material is around 1, 1 mg tissue is 1 mm$^3$ or (1000µ)$^3$. The density of specific labels is then around 6 molecules per µ$^3$.

The extracellular fraction (lambda) [26] is usually low (0.2), so that most of the volume is taken up by brain material. Even when neurons are outnumbered largely by glia and astrocytes, because of their long projections, they take up a substantial fraction of the volume. Suppose they take up 80% of the brain material, this would suggest that neurons contribute to about 64% of total material. Synapses are usually located on synaptic boutons, which is a central unit. If boutons account for 50% of neuronal material, then 32% of total material consists of synapses. The diameter of those boutons range from 0.5 to 3.5µ [50]. Suppose the mean radius is 1µ, then the volume is about 4µ$^3$. If all receptors would be concentrated in bouton material, we get 4×6×3=72 receptors per bouton, and per synapse. A certain fraction of receptors (50%) might be located intracellularly, so we end up with 30-36 receptors/µ$^2$. This is in the range of presynaptic Ca-channel density [50], which is about 45 channels/µ$^2$.

Similarly, if $A_2$ is the concentration of the presynaptic $\alpha_2$ receptors, we can write $$a_2(t)=A_2*\{N(t)/[N(t)+K_i]\}$$

where $K_i$ is the concentration of norepinephrine which occupies 50% of the $\alpha_2$ receptors and $a_2(t)$ is the concentration of $\alpha_2$ receptors bound by norepinephrine at time t. An experimental estimate of $K_i$ for NE at the $\alpha_2$a-R is 996 nM and at the $\alpha_2$d-R is 1031 nM [72]. We take a value of 1 µM.

An estimation for $A_2$ can be deduced as follows. The specific binding of the alpha 2-adrenoceptor agonist [$^3$H]clonidine was measured in the postmortem brain of ethanol intoxicated nonalcoholic subjects and matched controls [62]. In the frontal cortex, the density of binding sites for [$^3$H]clonidine ($B_{max}$=58±7 fmol/mg protein) and [$^3$H]bromoxidine (UK 14304) ($B_{max}$=49±7 fmol/mg protein) in ethanol intoxicated subjects did not differ from those in the control groups ($B_{max}$=68±4 and 56±8 fmol/mg protein for the respective radioligand). We can therefore calculate a $B_{max}$ of 60 fM/mg protein for $\alpha_2$ adrenoceptors. Using a similar argument as outlined above, we can then estimate the density of presynaptic $\alpha_2$ receptors.

The $\alpha_2$ adrenergic receptors at the presynaptic membrane are autoreceptors, which limit the release of subsequent NE. Full stimulation of these receptors (above the basal level by NE) by clonidine (an a2 adrenoceptor agonist)

reduces 5HT firing (and subsequent PFC 5HT release) by 45% [45]. If R is the amount of norepinephrine released, $\alpha_2$ is the α2 activity (a value between 0=no activity and 1=fully active) and b is the maximum amount of norepinephrine released. (b=i.e. 5000 molecules/action potential or 150 uM)

$$R=b(1-p\,a_2)$$

where p is a free parameter chosen so that when there is maximum activity, the release will only decrease up to 45%. (p=0.63)

The $\alpha_2$ adrenergic autoreceptors are G-protein coupled receptors which a negative feedback on the subsequent NE release. Usually, there is a time-delay of about 40 minutes before the full effect becomes available [45]. However, we allow for an immediate effect in our current version of the simulation. Since the effect is continuous, the delay will eventually not matter.

The Norepinephrine Transporter (NET) uptake kinetics usually follows a Michaelis-Menten scheme and is energy- and sodium dependent. In the rat jejunum [90] two NET populations have been found. The high-affinity component (uptake 1) exhibited a Michaelis constant ($K_m$) of 1.72 μM and a maximum velocity ($V_{max}$) of 1.19 nmol.g-1.10 min-1. The low-affinity component (uptake 2) exhibited a $K_m$ of 111.1 μM and a $V_{max}$ of 37.1 nmol.g-1.10 min-1. We use the parameters for the high-affinity uptake component. Furthermore, blocking the NET by venlafaxine, leads to a robust NE increase of 498% in cortex [9]. We let no be the number of working NET present and $n_f$ be a user controlled parameter adjusting the relative amount of NET. ($n_f$=1). The value of was no chosen so that when the alfa-2 receptor was completely blocked, the resulting release would increase by 50% over the normal case. An estimate of the number of NET is given by the observation that in the striatal nucleus of rhesus monkey, the $^3$H-nisoxetine density is between 20 and 35 fM/mg tissue. The estimate for the density $n_o$ is right in the experimentally determined density.

$$\frac{\partial N(t)}{\partial t} = -n_f * n_o * V_{max} N(t)/[N(t) + K_m]$$

Norepinephrine can also disappear from the cleft through diffusion. For simplicity, we assume that the rate of dissipation is proportional to the amount of norepinephrine in the cleft (k is the rate of exponential decay). We use the same value as for serotonin (see above), i.e. k=ln(2)/500.

$$\frac{\partial N(t)}{\partial t} = -kN(t)$$

Presynaptic Serotonergic Terminal in PFC

The Basal Firing rate of serotonergic neurons is 1.3 Hz [29]. However about half of the neurons in the Dorsal Raphe Nucleus display a higher firing frequency of 1.9±0.1 Hz. We let $t_n$ be the global time at which the $n^{th}$ firing takes place, $T_n$ is the time period of the $n^{th}$ firing of the Dorsal Raphe and $T_o$ is the base period between firings. (Because the normal firing frequency is 1.3 Hz, $T_o$=1000/1.3=770 ms). The accumulation of $\alpha_1$ activity can be defined as $$I_n = \int_{t_{n-1}}^{t_{n-1}+T_{n-1}} a_1(t)dt$$

where $a_1(t)$ is the activation of the $\alpha_1$ receptor at time t (a value between 0=no activation and 1=full activation). $I_o$ is the average accumulation of $\alpha_1$ activity in the case where all neurons are firing monotonically. The accumulation of $\alpha_1$ activity is used to detemine the time of the next firing as follows $$T_n = T_o\left(2 - 2\frac{I_n^s}{I_n^s + I_o^s}\right)$$

where s is the sensitivity to change for the $\alpha_1$ receptor. s ranges between 0 and 1 where 0 means no change and 1 means sensitive to change. We take s=0.33 as default. As a consequence, when the al activity is normal, $I_n=I_o$ which causes $T_n=T_o$ and when the $\alpha_1$ activity is completely inhibited, $I_n=0$ which means that $T_n=2\,T_o$. (A doubling of the period means that the frequency is halved.)

A detailed study in serotonergic cultured Retzius cells [16] yields two populations of serotonergic containing vesicles both with a constant serotonin concentration of 270 mM. Amperometric analysis shows that these two types of vesicles (diameter 35 and 78 nm) release their content at once during an action potential. This calculates back to about 5000 and 80,000 molecules respectively [15]. In addition, most boutons release a single quantum at an action potential [76] with only 13-17% exhibiting multiple quanta release. Translated into the space of the small synaptic cleft, this is in the range of 100 μM. Although this has never been measured, it is in the same range as measures for ACh in the case of a cholinergic cleft. Therefore, if S(t) is the concentration of serotonin in the cleft at time t, then $$S(T)=S(T-dt)+b$$

where T is the time the Dorsal Raphe fires, dt is the step size in time, and b is the concentration of serotonin released into the cleft.

Serotonin binds to 5HT1b/d autoreceptors inhibiting subsequent 5HT release. Maximally blocking the 5HT1b/d autoreceptor by isamoltane increases free 5HT by 50%, whereas maximal stimulation by either CP93,129 or CP135, 807 decreases free 5HT by 45% [45]. This allows us to derive the mathematical equation linking free serotonin concentration to activity at the 5HT1b/d receptor. In contrast to the 5HT2 or 5HT3 receptors, receptors of the 5HT 1 class display a high-affinity binding for serotonin, in the range of 15 nM [61]. The functional affinity of serotonin for the 5HT1b/1d receptor is probably in the submicromolar range, as 10 μM fully activates the 5HIT1b/1d receptor in situ [66]. If a is the occupation/activation of the 5HT1b/d receptor by serotonin and S(t) is the concentration of serotonin in the cleft at time t.

$$a=r*D*S(t)/[K_t+S(t)]$$

where $K_t$ is the concentration of serotonin in which 50% of the SHT1b/d receptors are occupied, r is a user controlled parameter adjusting the relative amount of receptors present (r=1) and D is the amount of inhibition (e.g. due to drugs) at the 5HT1b/d receptor (a value between 0=full inhibition and 1=no inhibition). The concentration of serotonin R to be released can then be written:

$$R=b*(1-pa)$$

where b is the maximum amount of serotonin that can be released and p is a free parameter chosen so that when there is maximum activity, the release will only decrease up to 45%. (p=0.65).

The 5HT1b serotonergic autoreceptors are G-protein coupled receptors which exert a negative feedback on the subsequent 5HT release. Usually, there is a time-delay of about 40 minutes before the full effect becomes available [109]. In this version of the model we do not explicitly introduce this time-delay.

Finally, the 5HT transporter uptakes serotonin from the cleft. When it is blocked, the 5HT levels rise within the cleft.

The rise in 5HT causes an increase in the activation of the 5HT1b/d receptor. Maximal inhibition by fluoxetin essentially doubles the amount of free 5HT in the prefrontal cortex (from 4.3 to 8.6 fM/fraction) [6]. The 5HT-Transporter essentially follows Michaelis-Menten kinetics with a $K_m$ of 0.34 µM [80]. Therefore if S(t) is the concentration of serotonin in the cleft at time t, we can write $$\partial S/\partial t = -s_f s_o V_{max} * S(t)/[S(t)+K_i]$$

where $s_f$ is a user controlled parameter adjusting the relative amount of 5HT-T ($s_f$=1) and $s_o$ is the number of working 5HT-T ($s_o$=40). $V_{max}$ is the maximum rate at which serotonin is taken up by 5HT-T ($V_{max}$=2.5). $K_i$ is the concentration of serotonin at which the 5HT-T "pump" works at half its maximal speed ($K_i$=340 nM).

Serotonin can disappear from the cleft through diffusion or its interactions with enzymes and receptors which we do not explicitly include. For simplicity, we assume that the rate of dissipation is proportional to the amount of cleft serotonin.

$$\frac{\partial S(t)}{\partial t} = -kS(t)$$

where k is the rate of exponential decay. We assume a similar value for k (see above), i.e. k=ln 2/500.

The results of this simulation yield activation levels of postsyanypic 5HT1A, 5HT2A, alpha1A receptors in hippocampus and prefrontal cortex, which are then used in the calculations of cortical SMA serotonin effects in the EPS module and serotonergic and noradrenergic effects on working memory performance (see below).

E. Statistical Prediction of the Model Outcome.

Figure 11:
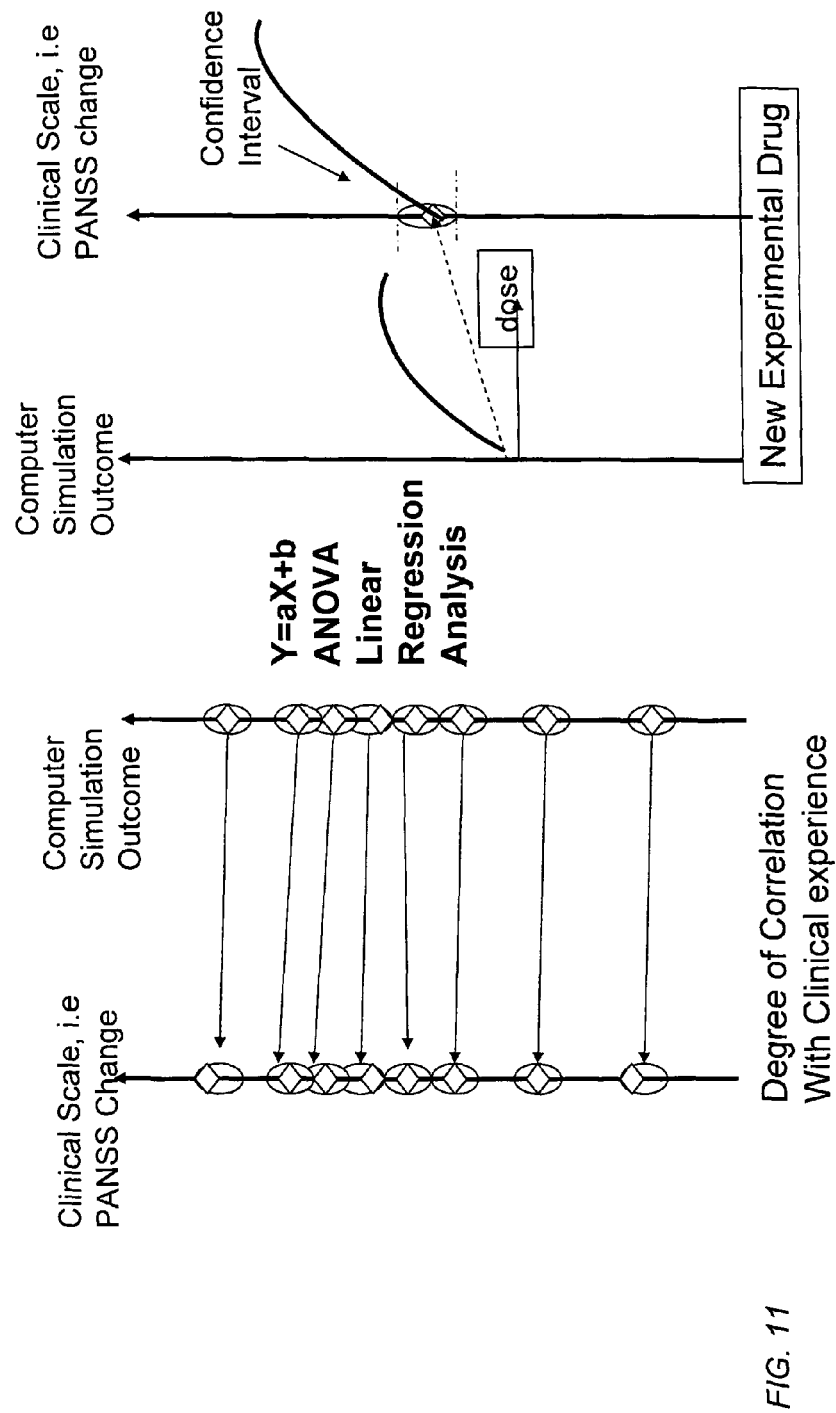
FIG. 11. Shows a schematic of how the mathematical model is validated through clinical correlation.

FIG. 11 presents all of the interacting entities with their geometric relationships used in predicting the performance of a new untested drug or combination on specific clinical scales. The model takes into account both G-protein coupled receptors and neurotransmitter transporters. Based upon the linear regression equation describing the correlation between the outcome of known drugs in the mathematical models and their clinical performance, we determine the values for the slope a and the intercept b. Based upon the pharmacology of the new untested drug, we calculate its outcome in the mathematical models and using the linear equation, determine the anticipated effect size on the clinical scale, together with a 95% confidence interval.

For each neuroleptic-dose combination used in the clinical trials, the outcome of the the EPS or Signal-to-Noise module is correlated with the clinical outcome, yielding the best linear equation Y=aX+b, where Y is the expected clinical outcome, X is the outcome of the simulation and a and b are parameters determined by the correlation analysis. The correlation coefficient indicates how good the fit is, with values close to 1 for better results. In addition, a Student's t-test determines the probability level that the hypothesis "the data are described by a linear relation Y=aX+b" is true.

Suppose the linear correlation yields an intercept a* and a slope b*, then the expected clinical scale outcome y for a new investigational drug with a dose corresponding to a Signal-to-Noise value of x* is (FIG. 1)

$$y = a^* + b^* x^*$$

with a prediction interval Pi, which can be calculated using statistical techniques. As a consequence, 95% of the cases the clinical scale will be between y−Pi and y+Pi, where $$Pi = t(\alpha/2) \times S \times \sqrt{\left(1 + \frac{1}{n} + \frac{(x^* - \langle x \rangle)2}{n \times Sxx}\right)}$$

F. Working Memory Circuit

Figure 12:
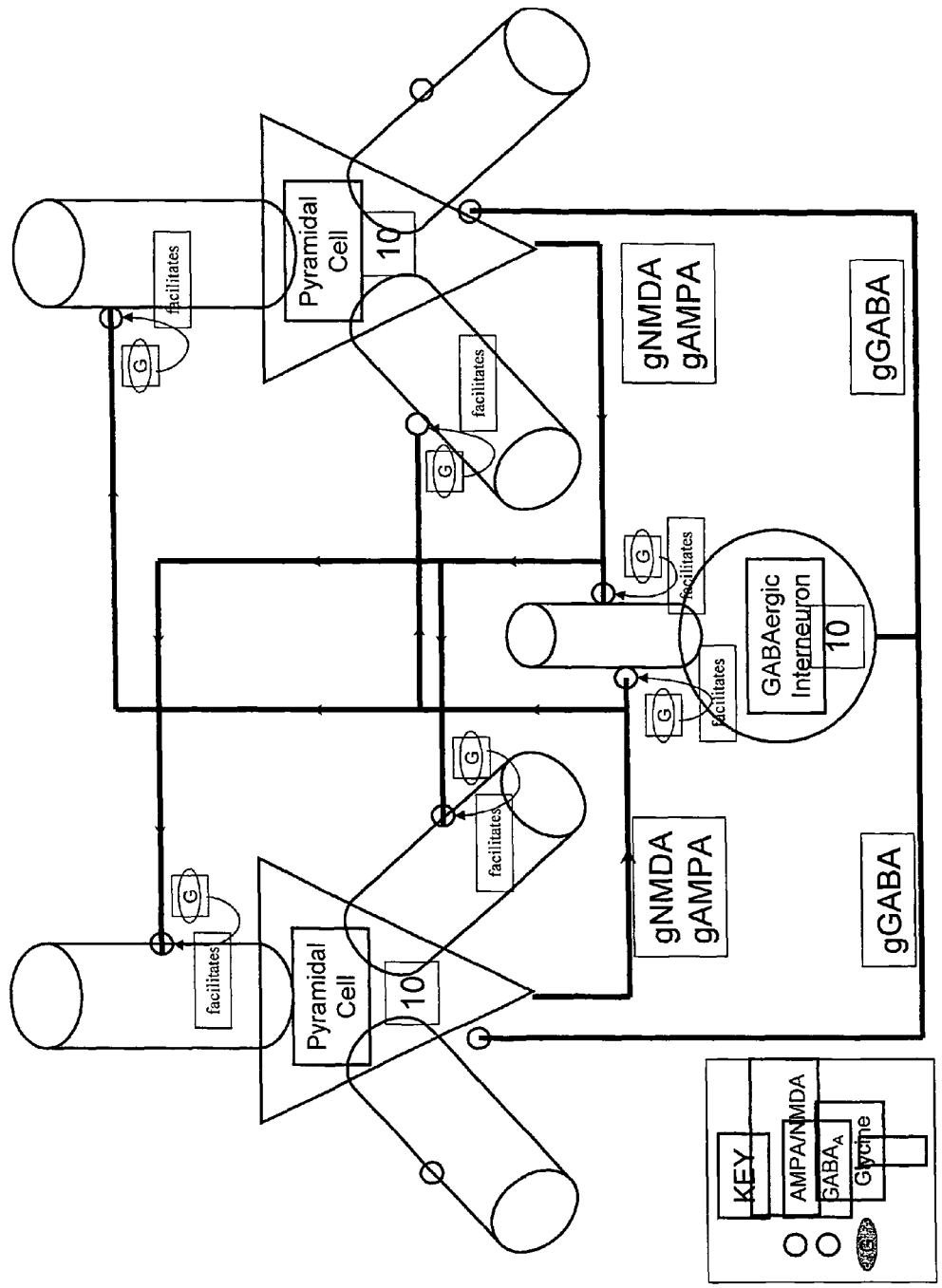
FIG. 12. Shows a schematic of the PFC neuronal network of pyramidal cells and interneurons.

FIG. 12 shows a schematic diagram of the PFC neuronal network of 20 pyramidal cells and 10 interneurons. The pyramidal cells synapse upon each other and drive 50% of the inhibitory network in a random fashion. Ten of the pyramidal cells form the attractor pattern, while the other 10 are part of the distractor pattern. All glutamatergic synapses have NMDA and AMPA receptors, while all GABAerge synapses have GABA-A receptor types. The pyramidal neurons consist of four compartments, the GABAergic neurons of two compartments.

In order to ensure a biophysically realistic model, Hodgin-Huxley type equations are implemented on $Ca^{2+}_{dyn}$ (first order model of calcium dynamics), $H_{va}$ (high voltage activated $Ca^{2+}$ current), iC (fast $Ca^{2+}$/voltage-dependent $K^+$ current), $I_{ks}$ (slowly inactivating $K_+$ channel), $K^+_{dr}$ (delayed rectifier K+ channel), $K^+_{dri}$ (delayed rectifier $K^+$ channel for interneuron), $K^+_{dyn}$ (simple first order model of $K^+$ dynamics), $Na^+_f$ (fast $Na^+$ channel), $Na^+_{int}$ (fast $Na^+$ channel for interneurons), $Na^+_p$ (persistent $Na^+$ channel) and on NMDA, AMPA and GABA-A receptors [30].

This model has been extended considerable to include the effect of pharmacological manipulation (see below). In addition, the original model yielded a proportional relationship between pyramidal cell activity and interneuron activity over the whole range of parameter settings, which is at odds with experimental data. Therefore, the model has been significantly adapted to account for the described asymmetric distribution of pyramidal-pyramidal and pyramidal-interneuron synapse. Rather than assuming a 1:1 ratio, we have allowed our model to have the number of pyramidal-interneuron connections randomly at 50% of the number of pyramidal-pyramidal interactions. This ensured the model to have an inverse relation ship between pyramidal cell firing and inhibitory cell firing.

In addition, more recent data on the difference between NMDA sensitivities between inhibitory and excitatory [5] have been implemented. This allows to refine the predictions.

Figure 13:
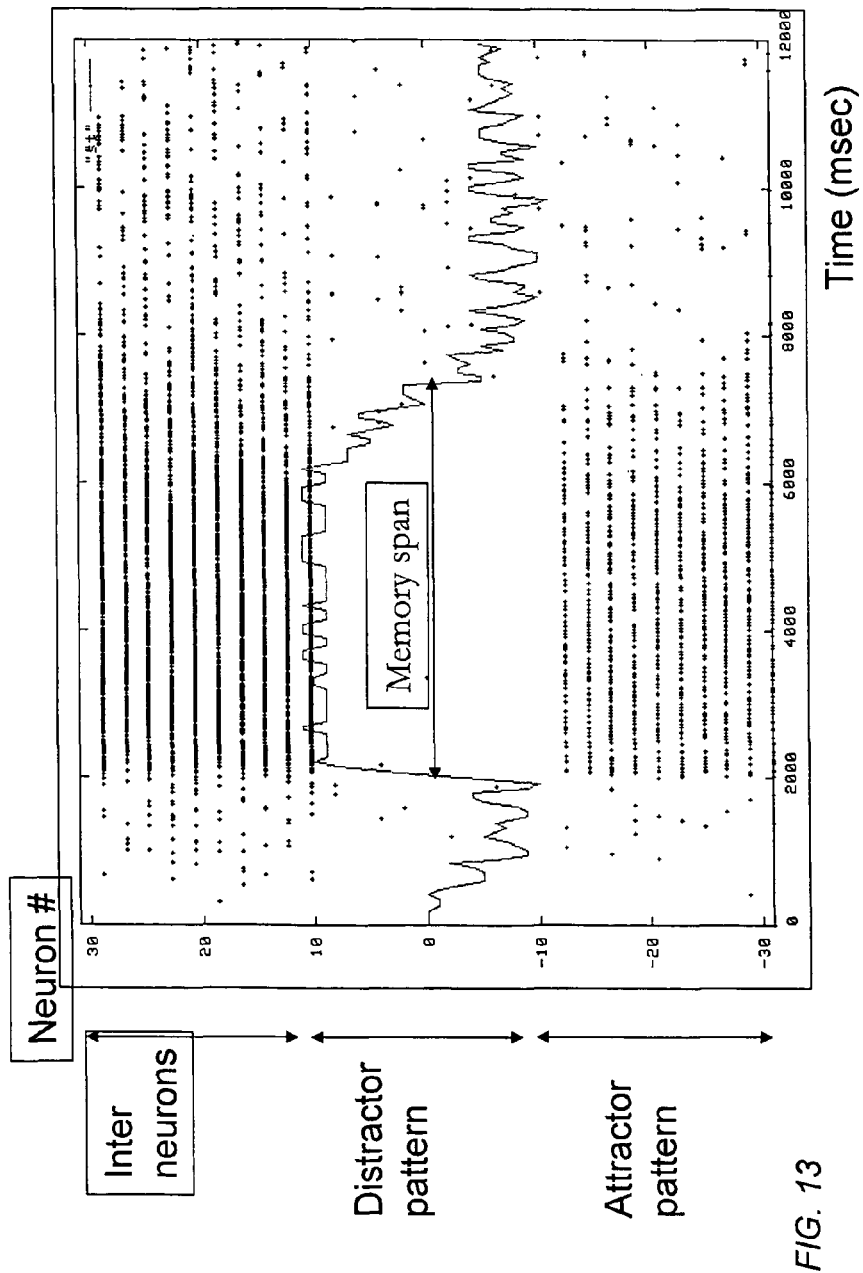
FIG. 13. Shows an illustration of the concept of working memory span.

FIG. 13 shows an illustration of the concept of working memory span. The x-axis is time in msec; every line represents the action potential activity of a single neuron. The first ten are the attractor pattern, cell 11-20 are the distractor pyramidal neurons and cell 21-30 are the GABA interneurons. At 2000 msec, a single current is injected in the attractor pattern, which remains active for a certain period (4-7 sec) without further stimulation.

Working memory in this circuit is simulated by a single injection of a current in the Target pattern which triggers a continuous reverberant synchronous activity for 6-8 seconds without any further stimulation, until the activity in the distractor pattern takes over. The length of this continuous active pattern (see FIG. 13) is the major readout of the model and is anticipated to be proportional to working memory performance. For each experiment, 140 simulations are run with random number seed.

An entropy factor can be calculated to assess quantitatively the 'complexity' and richness of the signal. The information content is derived using the approximate formulas for a finite spike train proposed by Strong [87]. Briefly, the information from the simulation consists of the timing of action potential for each of the 20 pyramidal and the 10 GABAergic neurons. An input module calculates the average firing frequency of pyramidal neurons and the total number of action potentials in the 10 GABAergic neurons. The activity of the 20 pyramidal neurons is then projected upon one time-axis, i.e. the identity of the neuronal cell firing is lost. A burst event is defined as the number of bins where adjacent activity is observed for the time bin (see below).

For the analysis of information content, the full spike train with a certain size is divided into time bins ΔT, where ΔT is 5 msec. A bin with an action potential is given the value 1, otherwise it is 0. In this way, words can be defined with maximal length T/ΔT. T is 4, 8, 12, 16, so that maximal word length spans a time delay of 90 msec.

If $p_i$ is the normalized count of i-th word $p_i$, then a naïve estimate of the entropy is given by $$S_{naive}(T, \Delta T; \text{size}) = -\sum_i p_i \log_2 p_i$$

True entropy is $$S(T,\Delta T) = \lim_{size \to \infty} S_{naive}(T;\Delta T;\text{size})$$

We are interested in the entropy rate $$S(T) = \lim_{T \to \infty} S(T,\Delta T)/T$$

We calculate the values for $S_{naive}(T,\Delta T;$ size'), where size'=total spike train/i, where i=1 . . . 4.

We get a parabolic estimate of S(T,ΔT) by considering $$S_{naive}(T, \Delta T; \text{size}) = S(T, \Delta T) + \frac{S_1(T, \Delta T)}{\text{size}} + \frac{S2(T, \Delta T)}{\text{size}^2}$$

If the correlations in the spike train have finite range then the leading subextensive contribution to the entropy will be $$\frac{S(T, \Delta T)}{T} = S(\Delta T) + \frac{C(\Delta T)}{T}$$

Such that a linear correlation of S(T,ΔT)/T vs 1/T enables one to determine the S(ΔT) as the intercept with the y-axis. This is usually expressed as bits/sec.

Another possible readout is an anticipated size of the fMRI BOLD signal, which is readily measurable in clinical setting. The bold signal reflects the total synaptic activity in the brain (Attwell 2002).

$$b(t) = \int_0^t h(t-t') \times I_{syn}(t')dt'$$

Where $I_{syn}(t)$ is total synaptic activity in the network model and $$h(t) = \frac{\lambda_1^{s_1} \times t^{s_1-1}}{(s_1-1)!} \times e^{-\lambda_1 t} - \frac{\lambda_2^{s_2} \times t^{s_2-1}}{(s_2-1)!} \times e^{-\lambda_2 t}$$

Where $s_1=6$; $s_2=10$; $\lambda_1=1.25$, $\lambda_2=1/8$; r=6 [33] is a hemodynamic response Pharmacology in Working Memory Circuit We introduce the functional effects of receptor modulation using the outcome of our generic receptor competition models and published data on the link between receptor activation, intracellular signaling and phosphihorylation mediated effects on ion-conductances.

Dopamine interacts through direct D1 receptor activation which increases NMDA receptor density [52] reduces AMPA currents [58], reduces $Ca^{2+}$ current [12], facilitates Na current [107] and facilitate GABA currents [111]. D1R activation is modulated at the level of dopaminergic neurons itself by Glutamatergic and serotonergic afferents in the Ventral Tegmentum Area.

Serotonin receptor through 5-HT1A and 5-HT2AR reduces conductances of Na and $Ca^{2+}$ channels in different compartments of pyramidal neuron (distal compartment for 5HT2A, all compartments for 5HT1A). The specific localized distribution of serotonergic and dopaminergic receptors has been documented in rodents and primates [68, 7]. A saturating dose of 5HT (1 μM) decreases the maximum conductance of the fast $Na^+$ channel, the persistent $Na^+$ channel, and the L-type $Ca^{++}$ channel by 20% [19].

Norepinephrine acts through alpha2A-R on GABA interneurons; stimulation of alpha2A-R decreases GABA neuron excitability, relieving inhibition in the network and increasing working memory performance.

Acetylcholine acts through postsynaptic M1R on pyramidal neurons via phasic and tonic effects, while presynaptic M2R modulates free Ach, which in turns activates α7 nAChR on glutamatergic neurons and α4β2 nAChR on GABA interneurons [35].

The 5-HT3 receptor has been shown to enhance GABAergic firing patterns in prefrontal cortex [78] in vivo. The GABA conductance allowing Cl ions to flow into the cells is associated with a hyperpolarization. This leads to a decrease in GABAergic interneuron firing, a decrease in inhibition and subsequently an increase in pyramidal neuron excitability.

In the following table, Act is the level of activation of the specific receptor

TABLE 6

Definitions of parameter values used in subsequent tables.

| Receptor | D1 | 5HT1A | 5HT2A | alfa2A |
|---|---|---|---|---|
| Effect | Activ/100 | 0.3* Act/100 | 0.2* Act/100 | 0.04* Act/100 |
| g-NMDA | g' = g*(1 + 0.4*Effect) | | | |
| g-AMPA- | g' = g*(1 − 0.2*Effect) | | | |
| g-GABA | g' = g*(1 + 0.2*Effect) | | | |

M1-R activation by transient high Ach release inhibit pyramidal neuron excitation (induces hyperpolarization) through IP3-mediated release of intracellular $Ca^{2+}$ and subsequent activation of apamin-sensitive, $Ca^{2+}$-activated $K^+$ conductance [41]. Fast M1R activation by bursts hyperpolarizes −4 mV (makes them less excitable), while M1-R activation by low tonic Ach depolarizes pyramidal neurons by +5 mV and makes them more excitable. If both processes work via the same mechanisms (i.e. effect on same K-conductance), we can calculate the net effect as follows $$\Delta MembPot = -5 \times \left(\frac{M_1^{act} - M_1^{rest}}{M_1^{rest}}\right)_{tonic} + 4 \times \left(\frac{M_1^{act} - M_1^{rest}}{M_1^{rest}}\right)_{phasic}$$

Full antagonism of presynaptic M2R increases free Ach by 251% in a neuromuscular junction [73]. Using the generic receptor competition model, the amount of M2R inhibition can be calculated for a given drug at a certain dose. Using the generic receptor competition model with α4β2nAChR postsynaptic receptors, the effect of such an increase of free Ach on the amount of receptor activation can be calculated as A-α4β2.

Using experimental data between galantamine concentration, nAChR activation and increase in Glu current (Santos 2002, Markus 2003), we arrive at the following relationship $$\Delta Glu_{current} = 0.103 \times \Delta nAChR - 0.00269$$

This allows us to calculate changes in gAMPA, gNMDA. Similarly for GABA mediated IPSC $$\Delta IPSC_{GABA} = 0.798 \times \Delta nAChR + 0.326$$

In the following table, Actrecdrug is the amount of nACHR activation in the presence of drug (possibly downstream of Acetylcholinesterase inhibition or presynaptic M2 blockade) and Actreccon is the activation level in no drug conditions.

TABLE 7

Effect of cholinergic and 5-HT3 receptor modulation on key conductances in the working memory model

| Receptor | M1 | M2 | a4b2nAChR | A7 nACHR | 5-HT3 |
|---|---|---|---|---|---|
| Effect | $\Delta MP = -5*$tonic inh $+ 4*$phasic inh; | $\Delta MP = -5*$tonic inh $+ 4*$phasic inh; | dIPSC = 0.326 + 0.798*(Actrecdrug-Actreccon)/Acrreccon; | d-Glucurr = −0.00269 + 0.103*(Actrecdrug-Actreccon)/Acrreccon; | (100-Act)/2.5 |
| g-NMDA | | | | gNMDA = 0.00346 + 0.181d-Glucurr | |
| g-AMPA- | | | Glucurr; | gAMPA = 0.0058 + 0.6913*d-Glucurr | g' = g*(1 + Effect) |
| g-GABA | | | gGABA = 0.33 + 0.08d-IPSC (interneuron) | | |
| Pyr-gK | = 0.3* D MP | = 0.3* D MP | | | |

Individual changes of all ion-channels in the apical distal compartment of the pyramidal cell are given in the following table

TABLE 8

Effect of dopaminergic, serotonergic and adrenergic G-PCR modulation on key conductances in the pyramidal apical-distal compartment in the working memory circuit.

| Regio | Receptor | Default values | D1 | 5HT1A | 5HT2A | alfa2A |
|---|---|---|---|---|---|---|
| Apical-Distal | gNaf | 0.028 | | Naf' = Naf * * Eff | Naf' = Naf * effect | |
| | gNap | 0 | | Nap' '2 Nap * Effect | Nap' = Nap * Effect | |
| | gHva | 0.00034 | g' = g * (1 − 0.5 * Effect) | gHVa' = gHVa * Effect | | |
| | gKdr | 0.0092 | | | | |
| | gIks | 0.00024 | g' = g * (1 − 0.5 * Effect) | | | |
| | gCa | 0.0022 | | gCa' = gCa * Effect | gCa' = gCa * Effect | |

Individual changes of all ion-channels in the apical proximal compartment of the pyramidal cell are given in the following table:

TABLE 9

Effect of dopaminergic, serotonergic and adrenergic G-PCR modulation on key conductances in the pyramidal apical-proximal compartment in the working memory circuit.

| Regio | Receptor | Default values | D1 | 5HT1A | 5HT2A | alfa2A |
|---|---|---|---|---|---|---|
| Apical-proximal | gNaf | 0.028 | | Naf' = Naf**Eff | | |
| | gNap | 0.001 | | Nap' = Nap*Effect | | |
| | gHva | 0.0007 | g' = g*(1 − 0.5*Effect) | gHVa' = gHVa*Effect | | |
| | gKdr | 0.0092 | | | | |
| | gIks | 0.00024 | g' = g*(1 − 0.5 *Effect) | | | |
| | gCa | 0.0038 | | gCa' = gCa*Effect | | |

Individual changes of all ion-channels in the basal compartment of the pyramidal cell are given in the following table:

TABLE 10

Effect of dopaminergic, serotonergic and adrenergic G-PCR modulation on key conductances in the pyramidal basal-pyramidal compartment in the working memory circuit.

| Regio | Receptor | Default values | D1 | 5HT1A | 5HT2A | alfa2A |
|---|---|---|---|---|---|---|
| Basal-pyramidal | gNaf | 0.028 | | Naf' = Naf**Eff | | |
| | gNap | 0.001 | | Nap' = Nap*Effect | | |

TABLE 10-continued

Effect of dopaminergic, serotonergic and adrenergic G-PCR modulation on key conductances in the pyramidal basal-pyramidal compartment in the working memory circuit.

| Regio | Receptor | Default values | D1 | 5HT1A | 5HT2A | alfa2A |
|---|---|---|---|---|---|---|
|  | gHva | 0.0007 | g' = g*(1 − 0.5*Effect) | gHVa' = gHVa*Effect |  |  |
|  | gKdr | 0.0092 |  |  |  |  |
|  | gIks | 0.00024g' | = g*(1 − 0.5 *Effect) |  |  |  |
|  | gCa | 0.0038 |  | gCa' = gCa*Effect |  |  |
| Basal-pyramidal | gNaf | 0.028 |  | Naf' = Naf**Eff |  |  |

Individual changes of all ion-channels in the soma compartment of the pyramidal cell are given in the following table:

TABLE 11

Effect of dopaminergic, serotonergic and adrenergic G-PCR modulation on key conductances in the pyramidal somatic compartment in the working memory circuit.

| Regio | Receptor | Default values | D1 | 5HT1A | 5HT2A | alfa2A |
|---|---|---|---|---|---|---|
| Soma-pyramidal | gNaf | 0.086 |  | Naf' = Naf**Eff |  |  |
|  | gNap | 0.0022 |  | Nap' = Nap*Effect |  |  |
|  | gHva | 0.00034 | g' = g*(1 − 0.5*Effect) | gHVa' = gHVa*Effect |  |  |
|  | gKdr | 0.0338 |  |  |  |  |
|  | gIks | 0.00014 | g' = g*(1 − 0.5*Effect) |  |  |  |
|  | gCa | 0.0022 |  | gCa' = gCa*Effect |  |  |
|  | gNaf | 0.086 |  | Naf' = Naf**Eff |  |  |

Similarly, conductance changes in the two GABA compartments are given in the following table:

TABLE 12

Effect of dopaminergic, serotonergic and adrenergic G-PCR modulation on key conductances in the two GABAergic compartment in the working memory circuit.

| Regio | Receptor | Default values | D1 | 5HT1A | 5HT2A | alfa2A |
|---|---|---|---|---|---|---|
| GABA dendrite | gCa | 0 |  |  |  |  |
|  | gNa | 0.02 |  |  |  |  |
|  | gK | .0.008 |  |  |  |  |
| GABA soma | gCa | 0 |  |  |  |  |
|  | gNa | 0.1 |  |  |  |  |
|  | gK | 0.04 |  |  |  | gK' = gK (1 − Effect) |
| GABA dendrite | gCa | 0 |  |  |  |  |

Validation of the Working Memory Model

Figure 14:
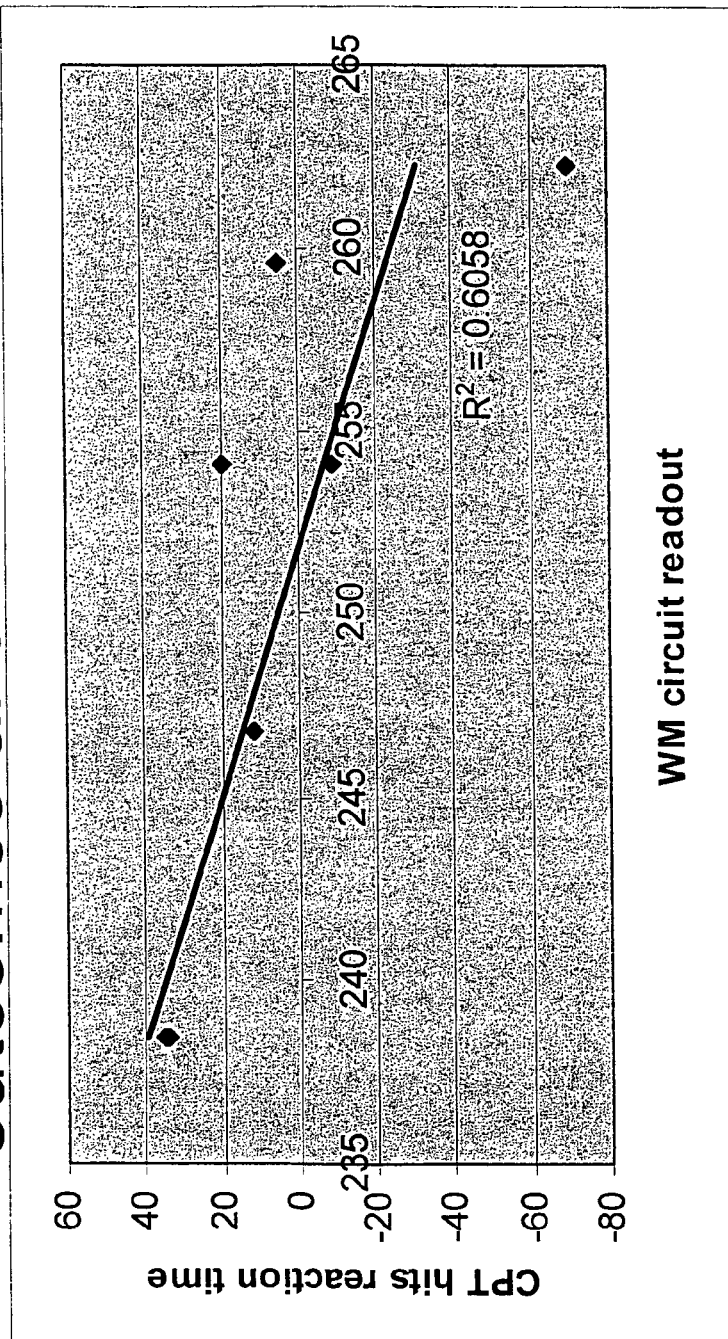
FIG. 14. Shows a graph between clinical outcome on a CPT test and their respective effects on working memory in the Working Memory circuit.

The model is validated using the correlation between the outcome of amisulpride, haldol, olanzapine, guanfacine and risperidone on Continuous Performance Test (CPT) test reaction time and their respective outcomes in the mathematical model of working memory (FIG. 14). AcCorrelation between clinical outcome on a CPT test for four different neuroleptics (7 points) and their respective effects on working memory in the Working Memory circuit is shown. The drugs used are amisulpride, haldol, olanzapine, risperidone and guanfacine. The p-value is 0.027. This shows that a reasonable correlation can be achieved between the outcome of the computer model and the clinical scales.

G. Applications of the Simulations

Target Identification

Figure 15:
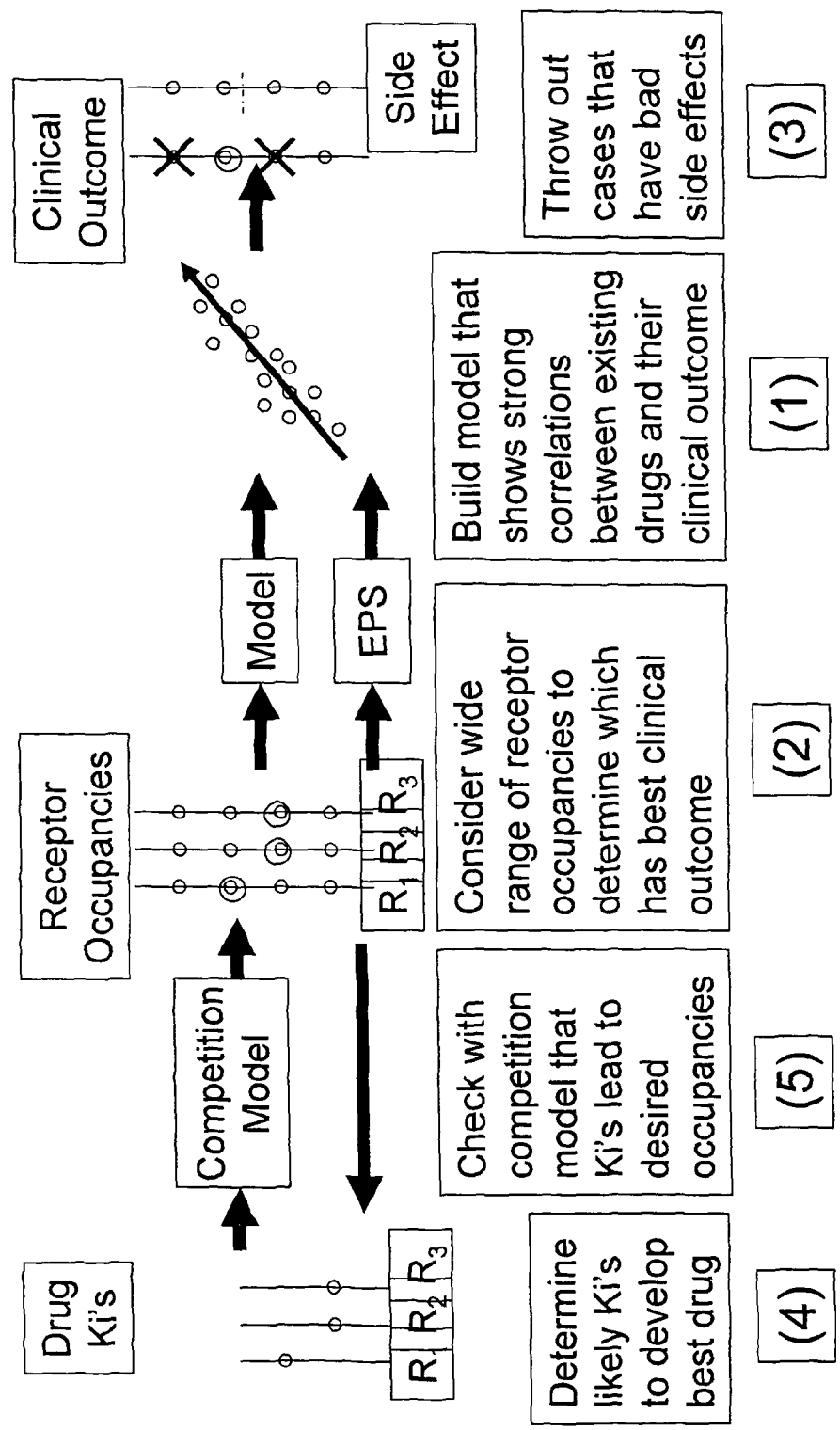
FIG. 15. Shows a flow chart of a model for identifying a pharmacological profile resulting in a substantially better clinical outcome.

FIG. 15 shows the conceptual approach to use the reverse approach in order to identify a pharmacological profile which results in a much better outcome on clinical scales than the state-of-the art current treatment. Reverse application of the model allows for identifying the pharmacological profile resulting in a substantially better clinical outcome than current standard of care. After validating the model by achieving a strong correlation between computer model outcome and clinical scales (1), a systematic search over all dimensions of receptor activations is performed to find the best clinical outcome (2). The profiles are tested against EPS side-effects and are ranked according to their performance (3). Then a search for affinity constants and functional properties reveal the actual profile of the ideal drug (4), which will be confirmed using the generic receptor competition model followed by the different modules (5).

A systematic probing of the parameter space of receptor activation levels enables to rank order putative receptor profiles in order of their impact on anticipated clinical scales. The EPS module is used as a filter to eliminate candidate profiles which are anticipated to show adverse motor-effects. Using this approach we identified four receptors which contribute most to the beneficial effect and which therefore constitute an ideal profile. Such a profile can then be used in Drug discovery efforts to search for small molecules, whose effect on the receptors resembles very closely this ideal profile. Obviously there will be different possibilities and the simulation platform will enable them to rank order them in terms of clinical benefit and possible motor side-effects. This kind of evaluation will be helpful to select the best candidate drug(s) for further development.

Comedication

Another possible application of the simulation platform is the issue of comedications, i.e. what combination of drugs gives the best results. This is helpful in supporting decision aspects of polypharmacy, which can be a public medical health problem. As an example, we studied the possible combination therapy of a glycine-transporter T1 inhibitor with an existing neuroleptic. Briefly, the model then incorporates the pharmacological effects of the combination therapy at all levels, i.e. receptor competition model, EPS, SN module and working memory circuit. The results showed that the best order would be ziprasidone 90 mg>paliperidone 12 mg>risperidone 6 mg>quetiapine 600 mg>olanzapine 15 mg>clozapine 500 mg in terms of additional gains on the PANSS total. With regard to the PANSS negative, the rank order is rsiperidone 6 mg>paliperidone 12 mg>ziprasidone 90 mg>quetiapine 600 mg>olanzapine 15 mg>clozapine 500 mg.

Power Analysis and Virtual Patient Trial

A virtual patient trial can be simulated using the variability of the drug plasma levels, obtained in human volunteers or patients, combined with the inherent variability of the brain configuration as outlined in Table 4. Briefly, a virtual patient is defined from a sample taken from the probability curve of plasma variability (for example the olanzapine PK profile has been described in Callaghan [18]) and independently from the probability functions of all the receptor densities involved in the simulation modules. The effect of a particular antipyschotic is calculated and the combined outcomes for all th virtual patients constitute a database from which using classical statistical analyses, power estimates of the number of patients needed to show an effect of $p<\alpha$ with a power of $\beta$ can be derived. As an example, using the data on the variability of an investigative glycine transporter inhibitor combined with olanzapine, it has been shown that it will take 328 patients to show a difference between olanzapine and the combination treatment with a p-value <0.05 at a power of 0.80.

Effect of Genotype on Clinical Effect

In some cases, the functional effect of a certain genotype is known. An example in point is the Val159Met polymorphism of the human Catechol-O-methyl transferase (COMT) gene, which leads to an twofold increase in stability at body temperature for the Val/Val form compared to the Met/Met isoform (for a review see Weinberger [104]). As this enzyme is implicated in the degradation of catecholamines, notably dopamine and norepineprhine in the prefrontal cortex, but not in the striatum, it has a substantial effect on the half-life or residence time of these neurotransmitters, especially in the working memory circuit. The simulation allows incorporating these effects by changing the half-life of dopamine and norepinephrine in the generic receptor competition model, which leads to a change in postsynaptic receptor activation. As an example we have studied the effect of the COMT Val158/Met polymorphism on the working memory performance of olanzapine. The information content, a measure of the complexity of the signal (see above) and proportional to working memory span, increases from 246.6±8.6 bit/sec (average±SE) in the VV genotype to 260.8±8.9 bit/sec in the MV genotype and to 263.8±8.7 bit/sec in the MM genotype. These results are in line with clinical results phrenia patients [8].

Chronopharmacodynamics

In certain conditions, the circadian rhythms of the properties (such as receptor densities and neurotransmitter dynamics) are known in preclinical models. In such cases, this information can be incorporated into the parameter set of the various simulation modules, to assess the effect of these circadian rhythms on the effect of pharmacological agents. Such information can be used together with the known pharmacokinetic profile of the investigative agent to obtain the best time for drug application and clinical assesment.

Circadian rhythms have been described for the density of striatal D2R which follows a 24 hr cycle and for density of the vesicle Glutamate Transporter 1 (VGLUT), which follows a 12 hr cycle [108]. For the D2R fluctuation, the mRNA is about 30% higher during the wake phase than during the sleep phase [103]. Also, clinical data suggest that patients on a steady Haldol therapy have higher Parkinsonian tremor and EPS when probed in the morning [96], while dyskinesia was worse in the afternoon [47]. In case of the VGLUT, the fluctuation with a maximal change of 25% is dependent upon the clock gene Period2, as the circadian rhythm is profoundly disturbed in a Period2 KO mouse model.

When applying this information to the known pharmacokinetic profile of risperidone, it turns out that the dynamic range of estimated PANSS total clinical scale, is only one point. The best effects in terms of benefit-risk (PANSS-EPS) ratio are seen when the drug is given in the evening and the clinical assessment is done in the late morning. In contrastm, with olanzapine the dynamic range over a 24 hour period is much bigger (4 points on the PANSS total scale).

While the invention has been described and illustrated herein, those of ordinary skill in the art will readily envision a variety of other means and/or structures for performing the functions and/or obtaining the results and/or one or more of the advantages described herein, and each of such variations or modifications is deemed to be within the scope of the present invention. More generally, those skilled in the art will readily appreciate that all parameters, dimensions, materials, and configurations described herein are meant to be exemplary and that the actual parameters, dimensions, materials, and configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and/or claimed. The present invention is directed to each individual feature, system, material and/or method described herein. In addition, any combination of two or more such features, systems, articles, materials and/or methods, if such features, systems, articles, materials and/or methods are not mutually inconsistent, is included within the scope of the present invention.

All definitions as used herein are solely for the purposes of this disclosure. These definitions should not necessarily be imputed to other commonly-owned patents and/or patent applications, whether related or unrelated to this disclosure. The definitions, as used herein, should be understood to control over dictionary definitions, definitions in documents incorporated by reference, and/or ordinary meanings of the defined terms.

REFERENCES

The following references are all incorporated herein by reference.

1. Abi-Dargham A, Mawlawi O. Lombardo I. Gil R. Martinez D, Huane Y. Hwang D R, Keilp J. Kochan L. Van Heertum R. Gorman J M. Laruelle M. Prefrontal dopamine D1 receptors and working memory in schizophrenia. J Neurosci. 2002:22(9):3708-19.
2. Abi-Dargham A, Rodenhiser J, Printz D, Zea-Ponce Y, Gil R, Kegeles L S, Weiss R, Cooper T B, Mann J J, Van Heertum R L, Gorman J M, Laruelle M. Increased baseline occupancy of D2 receptors by dopamine in schizophrenia. Proc Natl Acad Sci USA. 2000; 97(14):8104-9.
3. Blank.
4. Bamford N S, Zhang H, Schmitz Y, et al., Heterosynaptic dopamine neurotransmission selects sets of corticostriatal terminals. Neuron. 2004; 42(4):653-63.
5. Beierlein M, Gibson J R, Connors B W: Two dynamically distinct inhibitory networks in layer 4 of the neocortex, J Neurophysiol 2003, 90:2987-3000
6. Bel N, Artigas F. In vivo effects of the simultaneous blockade of serotonin and norepinephrine transporters on serotonergic function. Microdialysis studies. J Pharmacol Exp Ther September 1996; 278(3):1064-72
7. Berger B., Trotter S., Verney C, Gaspar P and Alvarez C. (1988). Regional and laminar distribution of the dopamine and serotonergic innervation in the macaque cerebral cortex: A radioautographic study. J. Comp. Neurol. 273, 99-119
8. Bertolino A, Caforio G, Blasi G, De Candia M, Latorre V, Petruzzella V, Altamura M, Nappi G, Papa S, Callicott J H, Mattay V S, Bellomo A, Scarabino T, Weinberger D R, Nardini M. Am J Psychiatry. October 2004; 161(10):1798-805 Interaction of COMT (Val(108/158)Met) genotype and olanzapine treatment on prefrontal cortical function in patients with schizophrenia. Am J Psychiatry. 2004; 161 (10):1798-805.
9. Beyer C E, Boikess S, Luo B, Dawson L A. (2002). Comparison of the effects of antidepressants on norepinephrine and serotonin concentrations in the rat frontal cortex: an in-vivo microdialysis study. J Psychopharmacol.;16(4): 297-304.
10. Braga M F, Aroniadou-Anderjaska V, Manion S T, Hough C J, Li H. Stress impairs alpha(1A) adrenoceptor-mediated noradrenergic facilitation of GABAergic transmission in the basolateral amygdala. Neuropsychopharmacology. January 2004; 29(1):45-58.
11. Briere R, Sherwin A L, Robitaille Y, Olivier A, Quesney L F, Reader T A. (1986). Alpha-1 adrenoceptors are decreased in human epileptic foci. Ann Neurol.; 19(l):26-30.
12. Brown A, Schwindt P, Crill W. Voltage-dependence and activation kinetics of pharmacologically defined components of the high threshold calcium current in rat neocortical neurons. J. Neurophysiol 1993; 70: 1530-1543
13. Brown P, Oliviero A, Mazzone P, Insola A, Tonali P, Di Lazzaro V. Dopamine dependency of oscillations between subthalamic nucleus and pallidum in Parkinson's disease. J Neurosci. 2001; 21(3): 1033-8.
14. Brunel N, Wang X J. (2001) Effects of neuromodulation in a cortical network model of object working memory dominated by recurrent inhibition. J Comput Neurosci. 11:63-85.
15. Bruns D, Jahn R. (1995). Real-time measurement of transmitter release from single synaptic vesicles. Nature.; 377(6544):62-5.
16. Bruns D, Riedel D, Klingauf J, Jahn R. (2000). Quantal release of serotonin. Neuron.; 28(1):205-20.
17. Budygin E A, John C E, Mateo Y, Jones S R. Lack of cocaine effect on dopamine clearance in the core and shell of the nucleus accumbens of dopamine transporter knock-out mice. J Neurosci. 2002; 22(10):RC222
18. Callaghan J T, Bergstrom R F, Ptak L R, Beasley C M. Olanzapine. Pharmacokinetic and pharmacodynamic profile. Clin Pharmacokinet. September 1999; 37(3):177-93.
19. Carr D B, Cooper D C, Ulrich S L, Spruston N, Surmeier D J. Serotonin receptor activation inhibits sodium current and dendritic excitability in prefrontal cortex via a protein kinase C-dependent mechanism. *J Neurosci.* (2002) 22:6846-55.
20. Cepeda C, Hurst R S, Altemus K L, Flores-Hemandez J, Calvert C R, Jokel E S, Grandy D K, Low M J, Rubinstein M, Ariano M A, Levine M S. Facilitated glutamatergic transmission in the striatum of D2 dopamine receptor-deficient mice. J Neurophysiol. 2001; 85(2):659-70.
21. Chen E Y. A neural network model of cortical information processing in schizophrenia. I: Interaction between biological and social factors in symptom formation. Can J Psychiatry. October 1994; 39(8):362-7.
22. Cheng G, Iijima Y, Ishibashi Y, Kuppuswamy D, Cooper G. Lithocholylcholine, a bile acid/acetylcholine hybrid, is a muscarinic receptor antagonist. J Pharmacol Exp Ther. October 2002; 303(1):29-35.
23. Chevalier G, Deniau J M (1990). Disinhibition as a basic process in the expression of the striatal function. Trends Neurosci 13:277-280
24. Cooper D C. The significance of action potential bursting in the brain reward circuit. Neurochem Int. 2002; 41(5): 333-40
25. Cragg. Variable dopamine release probability and short-term plasticity between functional domains of the primate striatum, J Neurosci. May 15, 2003; 23(10):4378-85
26. Cragg S J, Nicholson C, Kume-Kick J, Tao L, Rice M E. (2001). Dopamine-mediated volume transmission in midbrain is regulated by distinct extracellular geometry and uptake. J Neurophysiol. April; 85(4):1761-71.
27. Deco G, Rolls E T. (2003) Attention and working memory: a dynamical model of neuronal activity in the prefrontal cortex. Eur J Neurosci. 18:2374-90.
28. Di Matteo V, Cacchio M, Di Giulio C, Di Giovanni G, Esposito E. (2002) Biochemical evidence that the atypical antipsychotic drugs clozapine and risperidone block 5-HT (2C) receptors in vivo. Pharmacol Biochem Behav. 71(4): 607-13
29. Dong J, De Montigny C, Blier P. (1999). Assessment of the serotonin reuptake blocking property of YM992: electrophysiological studies in the rat hippocampus and Dorsal Raphe. Synapse; 34(4):277-89.
30. Durstewitz D, Seamans J K, Sejnowski T J. J Neurophysiol. Dopamine-mediated stabilization of delay-period activity in a network model of prefrontal cortex. 2000; 83(3): 1733-50.
31. Fall C P, Lewis T J, Rinzel J. (2005) Background-activity-dependent properties of a network model for working memory that incorporates cellular bistability. Biol Cybern. 93:109-118.
32. Finkel L H (2000) Neuroengineering models of brain disease. Annu Rev Biomed Eng. 2000; 2:577-606.
33. Freedman S, Patel S, Marwood R, Emms F, Seabrook G, Knowles M, McAllister G. Expression and pharmacological characterization of the human D3 dopamine receptor. J Pharmacol Exp Ther. January 1994; 268(1):417-26.

34. Friston K J, Fletcher P, Josephs O, Holmes A, Rugg M D, Turner R. Event-related fMRI; characterizing differential responses. Neuroimage 2: 45-63 (1998)
35. Gioanni Y, Rougeot C, Clarke P B, Lepouse C, Thierry A M, Vidal C. Nicotinic receptors in the rat prefrontal cortex: increase in glutamate release and facilitation of mediodorsal thalamo-cortical transmission. Eur J Neurosci 1999; 1 (1): 18-30
36. Gjedde A, Dyve S, Yang Y J, McHugh M, Pappius H M. (1991). Bi-affinity alpha 1-adrenoceptor binding in normal rat brain in vivo. Synapse.;9(1):1-6.
37. Goldman-Rakic P S. (1999) The physiological approach: functional architecture of working memory and disordered cognition in schizophrenia. Biol Psychiatry. 46:650-61
38. Goto Y, O'Donnell P. Timing-dependent limbic-motor synaptic integration in the nucleus accumbens. Proc Natl Acad Sci USA. Oct. 1, 2002; 99(20):13189-93.
39. Grace A A. Gating of information flow within the limbic system and the pathophysiology of schizophrenia. Brain Res Brain Res Rev. 2000; 31(2-3):330-41.
40. Gruber A J, Solla S, Surmeier J, Houk J. Modulation of striatal units by expected reward: a spiny neuron model displaying dopamine-induced bistability. J. Neurophysiol 2003; 90: 1095-1114
41. Gulledge A T, Stuart G J Cholinergic inhibition of neocortical pyramidal neurons. J Neurosci. 2005; 25(44): 10308-20.
42. Gurevich E V, Bordelon Y, Shapiro R M, Arnold S E, Gur R E, Joyce J N. Mesolimbic dopamine D3 receptors and use of antipsychotics in patients with schizophrenia. A postmortem study. Arch Gen Psychiatry. 1997; 54(3):225-32
43. Haddjeri N, de Montigny C, Blier P. (1997). Modulation of the firing activity of noradrenergic neurones in the rat locus coeruleus by the 5-hydroxtryptamine system." Br J Pharmacol; 120(5):865-75.
44. Hasselmo M E, Wyble B P. (1997) Free recall and recognition in a network model of the hippocampus: simulating effects of scopolamine on human memory function. Behav Brain Res. 89:1-34
45. Hertel P, Nomikos G G, Svensson T H. (1999). The antipsychotic drug risperidone interacts with auto- and hetero-receptors regulating serotonin output in the rat frontal cortex." Neuropharmacology; 38(8):1175-84.
46. Hsu K, Yang C, Huang C, Gean P. Carbachol induces inward current in neostriatal neurons through M1-like muscarinic receptors. Neuroscience. August 1996; 73(3): 751-60.
47. Hyde T M, Egan M F, Brown R J, Weinberger D R, Kleinman J E. Diurnal variation in tardive dyskinesia. Psychiatry Res. 1995; 56(1):53-7
48. Im W., Chio C, Alberts G, Dinh D. Positive allosteric modulator of the human 5-HT2C receptor. Mol Pharmacol. 2003; 64:78-84
49. Ince E, Ciliax B, Levey A. Differential expression of D1 and D2 dopamine and m4 muscarinic acetylcholine receptor proteins in identified striatonigral neurons. Synapse. December 1997; 27(4):357-66.
50. Jackson M B, Redman S J. Calcium dynamics, buffering, and buffer saturation in the boutons of dentate granule-cell axons in the hilus. J Neurosci. Mar. 1, 2003; 23(5):1612-21.
51. Kimko et al. Prediction of the outcome of a Phase III trial of an antipsyhcotic agent (quietipaine fumarate) by simulation with a population pharmacokinetic and pharmacodynamic model, Clin. Pharmacol. Ther 68, 568, 2000.
52. Kita H, Oda K, Murase K. Effects of dopamine agonists and antagonists on optical responses evoked in rat frontal cortex slices after stimulation of the subcortical white matter. Exp Brain Res. April 1999; 125(3):383-8.
53. Koh P O, Bergson C, Undie A S, Goldman-Rakic P S, Lidow M S. Up-regulation of the D1 dopamine receptor-interacting protein, calcyon, in patients with schizophrenia. Arch Gen Psychiatry. 2003; 60(3):311-9.
54. Koos T, Tepper J M. Dual cholinergic control of fast-spiking interneurons in the neostriatum. J Neurosci. 2002; 22(2):529-35.
55. Kovacs I, Yamamura H, Waite S, Varga E V, Roeske W. Pharmacological comparison of the cloned human and rat M2 muscarinic receptor genes expressed in the murine fibroblast (B82) cell line. J Pharmacol Exp Ther. February 1998; 284(2):500-7.
56. Kroese et al. H1-histamine receptor affinity predicts short-term weight gain for typical and atypical antipsychotic drugs. Neuropsychopharmacology. March 2003; 28(3):519-26.
57. Laakso A, Bergman J, Haaparanta M, Vilkman H, Solin O, Syvalahti E, Hietala J. Decreased striatal dopamine transporter binding in vivo in chronic schizophrenia. Schizophr Res. 2001; 52(1-2):115-20.
58. Law-Tho D, Hirsch J C, Crepel F. Dopamine modulation of synaptic transmission in rat prefrontal cortex: an in vitro electrophysiological study. Neurosci Res. 1994; 21(2):151-60
59. Lisman J E, Othmakova. Storage, recall, and novelty detection of sequences by the hippocampus: elaborating on the SOCRATIC model to account for normal and aberrant effects of dopamine. Hippocampus. 2001; 11 (5):551-68.
60. Macoveanu J, T. N. Klingber, J. Tegner. A Biophysical model of multiple-item working memory: a computational and neuroimaging study. Neuroscience 141; 1611-1618 (2006)
61. McAllister G, Charlesworth A, Snodin C, Beer M S, Noble A J, Middlemiss D N, Iversen L L, Whiting P. (1992). Molecular cloning of a serotonin receptor from human brain (5HT1E): a fifth 5HT1-like subtype." Proc Natl Acad Sci USA; 89(12):5517-21.
62. Meana J J, Gabilondo A M, Barturen F, Garcia-Sevilla J A. (1992). Acute ethanol intoxication may not alter alpha 2-adrenoceptors in the human brain. Psychopharmacology (Berl).; 107(1):132-4.
63. Mei L. Yamamura H, Roeske W. Pharmacologic comparison of selected agonists for the M1 muscarinic receptor in transfected murine fibroblast cells (B82). J Pharmacol Exp Ther. February 1991; 256(2):689-94.
64. Menschik E D, Finkel L H. Cholinergic neuromodulation and Alzheimer's disease: from single cells to network simulations. Prog Brain Res. 1999; 121:19-45.
65. Miles P R, Mundorf M L, Wightman R M. Release and uptake of catecholamines in the bed nucleus of the stria terminalis measured in the mouse brain slice. Synapse. 2002; 44(3): 188-97.
66. Millan M J, Gobert A, Audinot V, Dekeyne A, Newman-Tancredi A. (1999). Inverse agonists and serotonergic transmission: from recombinant, human serotonin (5-HT) 1B receptors to G-protein coupling and function in corticolimbic structures in vivo." Neuropsychopharmacology. 21; (2 Suppl):61S-67S
67. Miller P, Brody C D, Romo R, Wang X J (2003) A recurrent network model of somatosensory parametric working memory in the prefrontal cortex. Cereb Cortex. 13:1208-18.

68. Miner L A, Backstrom J R, Sanders-Bush E, Sesack S R. (2003) Ultrastructural localization of serotonin2A receptors in the middle layers of the rat prelimbic prefrontal cortex. Neuroscience. 116:107-17.
69. Montague P R, Hyman S E, Cohen J D. Computational roles for dopamine in behavioural control. Nature. Oct. 14, 2004a;431(7010):760-7.
70. Montague P R, McClure S M, Baldwin P R, Phillips P E, Budygin E A, Stuber G D, Kilpatrick M R, Wightman R M. Dynamic gain control of dopamine delivery in freely moving animals. J Neurosci. 2004b;24(7):1754-9.
71. Muramatsu I, Taniguchi T, Okada K. Tamsulosin. (1998). alpha1-adrenoceptor subtype-selectivity and comparison with terazosin. Jpn J Pharmacol.;78(3):331-5.
72. Naselsky D P, Ashton D, Ruffolo R R Jr, Hieble J P. (2001). Rabbit alpha2-adrenoceptors: both platelets and adipocytes have alpha2A-pharmacology. J Pharmacol Exp Ther.; 298(1):219-25.
73. Parnas H, Slutsky I, Rashkovan G, Silman I, Wess J, Parnas I. Depolarization initiates phasic acetylcholine release by relief of a tonic block imposed by presynaptic M2 muscarinic receptors. J Neurophysiol. 2005; 93(6): 3257-69
74. Piggott M A, Owens J, O'Brien J, Colloby S, Fenwick J, Wyper D, Jaros E, Johnson M, Perry R H, Perry E K. (2003) Muscarinic receptors in basal ganglia in dementia with Lewy bodies, Parkinson's disease and Alzheimer's disease. J Chem Neuroanat;25(3):161-73
75. Povlock S L, Schenk J O. A multisubstrate kinetic mechanism of dopamine transport in the nucleus accumbens and its inhibition by cocaine. J Neurochem. 1997; 69(3):1093-105.
76. Prange O, Murphy T H. (1999). Analysis of multiquantal transmitter release from single cultured cortical neuron terminals. J Neurophysiol.; 81(4): 1810-7.
77. Prasad S, Semwal P, Deshpande S, Bhatia T, Nimgaonkar V L, Thelma B K. Molecular genetics of schizophrenia: past, present and future. J Biosci. 2002; 27(1 Suppl 1):35-52
78. Puig M V, Santana N, Celada P, Mengod G, Artigas F. In vivo excitation of GABA interneurons in the medial prefrontal cortex through 5-HT3 receptors. Cereb Cortex. 2004; 14(12):1365-75.
79. Radcliffe K A, Fisher J L, Gray R, Dani J A. (1999) Nicotinic modulation of glutamate and GABA synaptic transmission of hippocampal neurons. Ann N Y Acad Sci 1999 868:591-610
80. Ramamoorthy S, Cool D R, Leibach F H, Mahesh V B, Ganapathy V. (1992), Reconstitution of the human placental 5-hydroxytryptamine transporter in a catalytically active form after detergent solubilization. Biochem J. 286 (Pt 1):89-95
81. Richelson E, Souder T. (2000). Binding of antipsychotic drugs to human brain receptors focus on newer generation compounds. Life Sci.; 68(1):29-39.
82. Scarr E., Keriakous D, Crossland N, Dean B. No change in cortical muscarinic M2, M3 receptors or [35S]GTPgammaS binding in schizophrenia. Life Sci. Feb. 9, 2006; 78(11):1231-7.
83. Schultz W, Dayan P, Montague P R. A neural substrate of prediction and reward. Science. Mar. 14, 1997; 275(5306): 1593-9.
84. Seeman P, Kapur S. Anesthetics inhibit high-affinity states of dopamine D2 and other G-linked receptors. Synapse. 2003; 50(1):35-40.
85. Silvestri S, Seeman M V, Negrete J C, Houle S, Shammi C M, Remington G J, Kapur S, Zipursky R B, Wilson A A, Christensen B K, Seeman P. Increased dopamine D2 receptor binding after long-term treatment with antipsychotics in humans: a clinical PET study. Psychopharmacology (Berl). 2000; 152(2): 174-80
86. Smith A J, Becker S, Kapur S. A computational model of the functional role of the ventral-striatal D2 receptor in the expression of previously acquired behaviors. Neural Comput. February 2005; 17(2):361-95.
87. Strong S P, de Ruyter van Steveninck R R, Bialek W, Koberle R. On the application of information theory to neural spike trains. Pac Symp Biocomput. 1998; 621-32
88. Sugita S, Uchimura N, Jiang Z G, North R A (1991). Distinct muscarinic receptors inhibit release of GABA and excitatory amino acids in mammalian brain. PNAS USA 88:2608-2611
89. Sunahara R K, Guan H C, O'Dowd B F, Seeman P, Laurier L G, Ng G, George S R, Torchia J, Van Tol H H, Niznik H B. Cloning of the gene for a human dopamine D5 receptor with higher affinity for dopamine than D1. Nature. 1991; 350(6319):614-9
90. Suvannapura A, Levens N R. (1988). Norepinephrine uptake by rat jejunum: modulation by angiotensin II. Am J Physiol.; 254(2 Pt 1):G135-41.
91. Szabo S T, Blier P. (2002). Effects of serotonin (5-hydroxytryptamine, 5-HT) reuptake inhibition plus 5-HT(2A) receptor antagonism on the firing activity of norepinephrine neurons. J Pharmacol Exp Ther.; 302(3):983-91.
92. Tanaka S. (2006) Dopaminergic control of working memory and its relevance to schizophrenia: a circuit dynamics perspective. Neuroscience. 39:153-71
93. Tauscher J, Kufferle B, Asenbaum S, Tauscher-Wisniewski S, Kasper S. Striatal dopamine-2 receptor occupancy as measured with [123I]iodobenzamide and SPECT predicted the occurrence of EPS in patients treated with atypical antipsychotics and haloperidol. Psychopharmacology (Berl). June 2002; 162(1):42-9.
94. Tauscher J, Jones C, Remington G, Zipursky R B, Kapur S Significant dissociation of brain and plasma kinetics with antipsychotics. Mol Psychiatry. 2002; 7(3):317-21.
95. Terman, D, Rubin J E, Yew A C, Wilson C J. 2002. Activity patterns in a model for the subthalamopallidal network of the basal ganglia. J. Neurosci 22:2963-76
96. Torner C, Herrera-Estrella M, Gutierrez J A, Aguilar-Roblero R. Diurnal variations of extrapyramidal symptoms induced by haloperidol in schizophrenic subjects. Int J Neuropsychopharmacol. 2003; 6(3):243-6.
97. Tort 2006, Progress in Neuro-psychopharmacology & Biol Psych 30, 541-548.
98. Van Oekelen D, Luyten W H, Leysen J E. 5-HT2A and 5-HT2C receptors and their atypical regulation properties. Life Sci. 2003; 72(22):2429-49.
99. Vauquelin et al. Slow antagonist dissociation and long-lasting in vivo receptor protection, Trends in Pharmacological Sciences, 27, 355-358 (2006).
100. Wang X J, Tegner J, Constantinidis C, Goldman-Rakic P S (2004) Division of labor among distinct subtypes of inhibitory neurons in a cortical microcircuit of working memory. Proc Natl Acad Sci USA. 01(5):1368-73
101. Wang X J. (2006) Toward a prefrontal microcircuit model for cognitive deficits in schizophrenia. Pharmacopsychiatry. 39:S80-7.
102. Wayment H K, Schenk J O, Sorg B A. Characterization of extracellular dopamine clearance in the medial prefrontal cortex: role of monoamine uptake and monoamine oxidase inhibition. Neurosci. 2001; 21(1):35-44.

103. Weber M, Lauterburg T, Tobler I, Burgunder J M. Circadian patterns of neurotransmitter related gene expression in motor regions of the rat brain. Neurosci Lett. 2004; 358(1):17-20.

104. Weinberger D R, Egan M F, Bertolino A, Callicott J H, Mattay V S, Lipska B K, Berman K F, Goldberg T E. Prefrontal neurons and the genetics of schizophrenia. Biol Psychiatry. Dec. 1, 2001; 50(11):825-44

105. Winterer G, Coppola R, Goldberg T E, Egan M F, Jones D W, Sanchez C E, Weinberger D R. Prefrontal broadband noise, working memory, and genetic risk for schizophrenia. Am J Psychiatry. 2004; 161(3):490-500.

106. Yan Z, Flores-Hernandez J, Surmeier D J (2001). Coordinated expression of muscarinic receptor messenger RNA in striatal medium spiny neurons. Neuroscience 103:1017-1024

107. Yang C R, Seamans J K. Dopamine D1 receptor actions in layers V-VI rat prefrontal cortex neurons in vitro: modulation of dendritic-somatic signal integration. J Neurosci. 1996; 16(5):1922-35.

108. Yelamanchili S, Pendyala G, Brunk I, Dama M, Albrecht U, Ahnert-Hilger G. Differential sorting of the vesicular glutamnate transporter 1 into a defined vesicular pool is regulkated by light signaling involving the clock gene period2*. Journ of Biol Chem. 2006; 281, 15671-15678

109. Yoshitake T, Yoshitake S, Yamaguchi M, Ogren S O, Kehr J. (2003). Activation of 5-HT(1A) autoreceptors enhances the inhibitory effect of galanin on hippocampal 5-HT release in vivo. Neuropharmacology.; 44(2):206-13

110. Zapata A, Shippenberg T S. D2 receptor ligands modulate extracellular dopamine clearance in the nucleus accumbens. J of Neurochemistry, 2002, 81:1035-1042

111. Zhou F., Hablitz J. Dopamine modulation of membrane and synaptic properties of interneurons in rat cerebral cortex. J. Neurophysiol. 1999; 81:967-976

The invention claimed is:

1. A method for predicting clinical effects of a proposed pharmacological therapy for treating a known neurological disease associated with neuronal circuits within and among cortical and sub-cortical brain regions, comprising the steps:
simulating a plurality of interconnected neuronal circuits within and among different regions of
a human brain afflicted with said neurological disease, each of the simulated circuits being separately modeled with the use of actual data about the neurological disease, wherein said different regions include the cortex, and at least one of the striatum, hippocampus, amygdala, ventral tegmentum area, locus coeruleus, dorsal raphe and substantia nigra, and
the simulated circuits include
simulated interactions within and among said different brain regions through neuronal projections, and
simulated synaptic transmissions incorporating action potentials and their effect on receptors of at least one of the following types: dopaminergic, serotonergic, noradrenergic, cholinergic, glutamatergic and GABA-ergic;
simulating the functional effects of each of a plurality of known pharmacological therapies on the receptors in said simulated circuits to thereby produce corresponding simulated biological effects on the interconnected neuronal circuits;
deriving a regression equation quantitatively correlating said simulated biological effects of said known therapies with the known clinical effects of said therapies on a clinical scale related to said neurological disease;
adjusting at least some parameters associated with said simulated circuits in order to develop modified simulated circuits resulting in a regression equation output having increased confidence measures of correlation between said simulated biological effects and said known clinical effects;
simulating the functional effects of a proposed pharmacological therapy on the receptors in said modified simulated circuits to thereby produce corresponding simulated biological effects on the interconnected neuronal circuits and inputting said simulated biological effects of said proposed pharmacological therapy into said regression equation; and
outputting from the regression equation a predicted quantitative clinical effect of the proposed pharmacological therapy on said clinical scale, together with a corresponding confidence measure for said predicted quantitative clinical effect, wherein the steps are performed in a programmed computer.

2. The method of claim 1, further comprising the step of using the simulated biological effects of said known therapies from the modified simulated circuits and the known clinical effects of said known therapies to derive a revised regression equation.

3. The method of claim 1, wherein said neurological disease is selected from the group consisting of Alzheimer's disease, Parkinson's disease, stroke, vascular dementia, Huntington's disease, epilepsy and Down syndrome.

4. The method of claim 1, wherein the proposed pharmacological therapy is selected from a plurality of cerebroactive therapeutic agents.

5. The method of claim 1, wherein the proposed pharmacological therapy includes a combination of different pharmacological agents each having a respective proposed dose.

6. The method of claim 1, wherein the proposed pharmacological therapy includes a proposed dose of least one pharmacological agent having unknown clinical effects on said clinical scale.

7. The method of claim 1, wherein the proposed pharmacological therapy includes a proposed dose of at least one known pharmacological agent.

8. The method of claim 1, wherein at least some of the actual data used to model the simulated neuronal circuits includes known circadian profiles of physiological parameters to thereby vary at least some of the simulated biological effects over the course of a 24 hour day.

9. The method of claim 1, wherein at least some of the actual data used to model the parameters of the simulated neuronal circuits is specific to one or more genotypes, whereby the predicted clinical effects will be applicable to those specific genotypes.

10. The method of claim 1, wherein at least some of the actual data used to model functional effects of pharmacological therapies on the receptors in the simulated neuronal circuits reflects drug plasma levels.

11. The method of claim 10, wherein at least some of the actual data used to model functional effects of pharmacological therapies on the receptors in the simulated neuronal circuits reflects distribution of receptor densities.

12. The method of claim 11, further comprising the steps: defining a sample of virtual patients each having a respective plasma and receptor density profile; and for each virtual patient in the sample, predicting a respective quantitative clinical effect of the proposed pharmacological therapy.

13. The method of claim 1, wherein the predicted quantitative clinical effect is measured on more than one clinical scale.

14. The method of claim 13, wherein the predicted quantitative clinical effect includes clinical efficacy.

15. The method of claim 13, wherein the predicted quantitative clinical effect includes side-effect liability.

16. The method of claim 13, wherein the predicted quantitative clinical effect includes both clinical efficacy and side-effect liability.

17. The method of claim 1, further comprising the steps: separately predicting a respective quantitative clinical effect on the same clinical scale for each of several proposed pharmacological therapies; and using those predicted clinical effects to rank the proposed pharmacological therapies.

18. The method of claim 1, further comprising the steps: varying receptor activation states in simulated neuronal synapses; selecting receptor activation states which result in a predicted clinical effect above a predetermined threshold; deriving a desired pharmacological target profile from the selected receptor activation states; and outputting a predicted clinical effect for a pharmacological therapy having the desired pharmacological target profile.

* * * * *